United States Patent
Ling

(10) Patent No.: US 10,369,199 B2
(45) Date of Patent: Aug. 6, 2019

(54) METHODS OF USING VARIANTS OF FGF19 POLYPEPTIDES FOR THE TREATMENT OF CANCER

(71) Applicant: NGM Biopharmaceuticals, Inc., South San Francisco, CA (US)

(72) Inventor: Lei Ling, Foster City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 73 days.

(21) Appl. No.: 15/032,605

(22) PCT Filed: Oct. 27, 2014

(86) PCT No.: PCT/US2014/062378
§ 371 (c)(1),
(2) Date: Jul. 25, 2016

(87) PCT Pub. No.: WO2015/065897
PCT Pub. Date: May 7, 2015

(65) Prior Publication Data
US 2016/0252497 A1    Sep. 1, 2016

Related U.S. Application Data

(60) Provisional application No. 61/896,473, filed on Oct. 28, 2013, provisional application No. 61/922,586, filed on Dec. 31, 2013, provisional application No. 62/067,273, filed on Oct. 22, 2014.

(51) Int. Cl.
*A61K 38/18* (2006.01)
*G01N 33/74* (2006.01)
*A01K 67/027* (2006.01)
*G01N 33/50* (2006.01)

(52) U.S. Cl.
CPC ...... *A61K 38/1825* (2013.01); *A01K 67/0275* (2013.01); *A01K 2227/105* (2013.01); *A01K 2267/0331* (2013.01); *G01N 33/5088* (2013.01); *G01N 33/74* (2013.01); *G01N 2800/04* (2013.01); *G01N 2800/042* (2013.01); *G01N 2800/7028* (2013.01); *G01N 2800/7066* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos | |
| 4,501,728 A | 2/1985 | Geho | |
| 4,837,028 A | 6/1989 | Allen | |
| 6,635,468 B2 | 10/2003 | Ashkenazi | |
| 6,716,626 B1 | 4/2004 | Itoh | |
| 6,806,352 B2 | 10/2004 | Desnoyers | |
| 6,812,339 B1 | 11/2004 | Venter | |
| 6,987,121 B2 | 1/2006 | Kliewer | |
| 7,115,415 B2 | 10/2006 | Goddard | |
| 7,129,072 B1 | 10/2006 | Schlessinger | |
| 7,208,312 B1 | 4/2007 | Desnoyers | |
| 7,259,248 B2 | 8/2007 | Itoh | |
| 7,288,406 B2 | 10/2007 | Bogin | |
| 7,390,879 B2 | 6/2008 | Ashkenazi | |
| 7,459,540 B1 | 12/2008 | Thomason | |
| 7,491,697 B2 | 2/2009 | Beals | |
| 7,576,190 B2 | 8/2009 | Glaesner | |
| 7,582,607 B2 | 9/2009 | Frye | |
| 7,622,445 B2 | 11/2009 | Frye | |
| 7,655,627 B2 | 2/2010 | Frye | |
| 7,667,008 B2 | 2/2010 | Thomason | |
| 7,705,195 B2 | 4/2010 | French | |
| 7,723,297 B2 | 5/2010 | Itoh | |
| 7,947,866 B2 | 5/2011 | Sparks | |
| 8,012,931 B2 | 9/2011 | Cujec | |
| 8,034,770 B2 | 10/2011 | Belouski | |
| 8,188,040 B2 | 5/2012 | Belouski | |
| 8,324,160 B2 | 12/2012 | Li | |
| 8,361,963 B2 | 1/2013 | Belouski | |
| 8,363,365 B2 | 2/2013 | Cujec | |
| 8,410,051 B2 | 4/2013 | Belouski | |
| 8,420,088 B2 | 4/2013 | Glass | |
| 8,481,031 B2 | 7/2013 | Glass | |
| 8,535,912 B2 | 9/2013 | Sonoda | |
| 8,541,369 B2 | 9/2013 | Dickinson | |
| 8,580,936 B2 | 11/2013 | Williams | |
| 8,618,053 B2 | 12/2013 | Belouski | |
| 8,642,546 B2 | 2/2014 | Belouski | |
| 8,673,860 B2 | 3/2014 | Schellenberger | |
| 8,741,841 B2 | 6/2014 | Darling | |
| 8,795,985 B2 | 8/2014 | Belouski | |

(Continued)

FOREIGN PATENT DOCUMENTS

| CN | 101591653 A | 12/2009 |
|---|---|---|
| CN | 102656266 A | 9/2012 |

(Continued)

OTHER PUBLICATIONS

Aranha et al., "Bile acid levels are increased in the liver of patients with steatohepatitis," Eur. J. Gastroenterol. Hepatol. 20(6): 519-525 (2008).
Beuers et al., "Medical treatment of primary selerosing cholagitis: a role for novel bile acids and other (post-) transcriptional modulators?", Clin. Rev. Allergy Immunol., 36(1):52-61 (2009).
Chazouilleres, "Primary sclerosing cholangitis and bile acids," Clinics and Research in Hepatology and Gastroenterology 36:S21-S25 (2012).

(Continued)

*Primary Examiner* — Christine J Saoud
(74) *Attorney, Agent, or Firm* — Jones Day

(57) ABSTRACT

Provided are methods of antagonizing the oncogenic activity of FGF19 in a subject. Also provided are methods of treating a FGF19-dependent cancer or tumor, or a symptom thereof in a subject.

25 Claims, 24 Drawing Sheets
Specification includes a Sequence Listing.

(56) References Cited

U.S. PATENT DOCUMENTS

| | | |
|---|---|---|
| 8,802,697 B2 | 8/2014 | Bifulco |
| 8,809,499 B2 | 8/2014 | Fan |
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,089,525 B1 | 7/2015 | Ling |
| 9,273,107 B2 | 3/2016 | Ling |
| 9,290,557 B2 | 3/2016 | Ling |
| 9,580,483 B2 | 2/2017 | Ling |
| 9,670,260 B2 | 6/2017 | Ling |
| 9,751,924 B2 | 9/2017 | Ling |
| 9,878,008 B2 | 1/2018 | Ling |
| 9,878,009 B2 | 1/2018 | Ling |
| 9,889,177 B2 | 2/2018 | Ling |
| 9,889,178 B2 | 2/2018 | Ling |
| 9,895,416 B2 | 2/2018 | Ling |
| 9,925,242 B2 | 3/2018 | Ling |
| 9,963,494 B2 | 5/2018 | Ling |
| 9,974,833 B2 | 5/2018 | Ling |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2005/0250684 A1 | 11/2005 | Heuer |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0215657 A1 | 8/2010 | Glass |
| 2010/0239554 A1 | 9/2010 | Schellenberger |
| 2010/0240587 A1 | 9/2010 | Schlein |
| 2010/0323954 A1 | 12/2010 | Li |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Baurin |
| 2011/0195077 A1 | 8/2011 | Glass |
| 2011/0195895 A1 | 8/2011 | Walker |
| 2011/0207912 A1 | 8/2011 | Botstein |
| 2011/0268794 A1 | 11/2011 | Camilleri |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2012/0151496 A1 | 6/2012 | Tebbs |
| 2012/0157397 A1 | 6/2012 | Hazen |
| 2013/0004492 A1 | 1/2013 | Marshall |
| 2013/0023474 A1 | 1/2013 | Ling |
| 2013/0116171 A1 | 5/2013 | Jonker |
| 2013/0122004 A1 | 5/2013 | Glass |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194352 A1 | 7/2014 | Ling |
| 2014/0243260 A1 | 8/2014 | Mohammadi |
| 2014/0243266 A1 | 8/2014 | Ling |
| 2015/0079065 A1 | 3/2015 | Wolf |
| 2015/0111821 A1 | 4/2015 | Suh |
| 2015/0132309 A1 | 5/2015 | Desnoyers |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |
| 2017/0182122 A1 | 6/2017 | Ling |
| 2017/0182123 A1 | 6/2017 | Ling |
| 2017/0232067 A1 | 8/2017 | Lindhout |
| 2017/0327551 A1 | 11/2017 | Ling |
| 2018/0110834 A1 | 4/2018 | DePaoli |
| 2018/0177846 A1 | 6/2018 | Ling |
| 2018/0318390 A1 | 11/2018 | Ling |

FOREIGN PATENT DOCUMENTS

| | | |
|---|---|---|
| CN | 103127503 A | 6/2013 |
| DE | 10100588 | 7/2002 |
| DE | 10100587 | 11/2002 |
| EA | 201001204 A1 | 2/2011 |
| EP | 2163626 | 3/2010 |
| JP | 2002112772 | 4/2002 |
| JP | 2009039117 | 2/2009 |
| JP | 2012530493 | 12/2012 |
| JP | 2013194049 | 9/2013 |
| NZ | 602702 | 3/2014 |
| WO | WO 2000/060085 | 10/2000 |
| WO | WO 2001/018209 | 3/2001 |
| WO | WO 2001/049740 | 7/2001 |
| WO | WO 2001/049849 | 7/2001 |
| WO | WO 2001/061007 | 8/2001 |

(56) References Cited

FOREIGN PATENT DOCUMENTS

| | | |
|---|---|---|
| WO | WO 2002/036732 | 5/2002 |
| WO | WO 2002/041911 | 5/2002 |
| WO | WO 2002/055693 | 7/2002 |
| WO | WO 2003/080803 | 10/2003 |
| WO | WO 2004/026228 | 4/2004 |
| WO | WO 2004/063355 | 7/2004 |
| WO | WO 2006/004076 | 1/2006 |
| WO | WO 2006/048291 | 5/2006 |
| WO | WO 2006/049854 | 5/2006 |
| WO | WO 2008/021196 | 2/2008 |
| WO | WO 2008/030273 | 3/2008 |
| WO | WO 2009/076478 | 6/2009 |
| WO | WO 2009/090553 | 7/2009 |
| WO | WO 2009/095372 | 8/2009 |
| WO | WO 2009/116861 | 9/2009 |
| WO | WO 2010/004204 | 1/2010 |
| WO | WO 2010/006214 | 1/2010 |
| WO | WO 2010/042747 | 4/2010 |
| WO | WO 2010/065439 | 6/2010 |
| WO | WO 2010/080976 | 7/2010 |
| WO | WO 2010/083051 | 7/2010 |
| WO | WO 2010/129600 | 11/2010 |
| WO | WO 2010/139741 | 12/2010 |
| WO | WO 2010/142665 | 12/2010 |
| WO | WO 2010/148142 | 12/2010 |
| WO | WO 2011/047267 | 4/2011 |
| WO | WO 2011/071783 | 6/2011 |
| WO | WO 2011/084808 | 7/2011 |
| WO | WO 2011/089203 | 7/2011 |
| WO | WO 2011/092234 | 8/2011 |
| WO | WO 2011/130417 | 10/2011 |
| WO | WO 2011/130729 | 10/2011 |
| WO | WO 2011/154349 | 12/2011 |
| WO | WO 2012/010553 | 1/2012 |
| WO | WO 2012/031603 | 3/2012 |
| WO | WO 2012/062078 | 5/2012 |
| WO | WO 2012/066075 | 5/2012 |
| WO | WO 2012/086809 | 6/2012 |
| WO | WO 2012/125812 | 9/2012 |
| WO | WO 2012/138919 | 10/2012 |
| WO | WO 2012/140650 | 10/2012 |
| WO | WO 2012/154263 | 11/2012 |
| WO | WO 2012/158704 | 11/2012 |
| WO | WO 2012/170438 | 12/2012 |
| WO | WO 2012/170704 | 12/2012 |
| WO | WO 2012/177481 | 12/2012 |
| WO | WO 2013/006486 | 1/2013 |
| WO | WO 2013/010780 | 1/2013 |
| WO | WO 2013/027191 | 2/2013 |
| WO | WO 2013033452 | 3/2013 |
| WO | WO 2013/049234 | 4/2013 |
| WO | WO 2013/109856 | 7/2013 |
| WO | WO 2013/131091 | 9/2013 |
| WO | WO 2013/151671 | 10/2013 |
| WO | WO 2013/173158 | 11/2013 |
| WO | WO 2013/184958 | 12/2013 |
| WO | WO 2013/184960 | 12/2013 |
| WO | WO 2013/184962 | 12/2013 |
| WO | WO 2013/188182 | 12/2013 |
| WO | WO 2014/031420 | 2/2014 |
| WO | WO 2014/037373 | 3/2014 |
| WO | WO 2014/085365 | 6/2014 |
| WO | WO 2014/105939 | 7/2014 |
| WO | WO 2014/130659 | 8/2014 |
| WO | WO 2014/149699 | 9/2014 |
| WO | WO 2014/152089 | 9/2014 |
| WO | WO 2014/152090 | 9/2014 |
| WO | WO 2015/065897 | 5/2015 |
| WO | WO 2015/112886 | 7/2015 |
| WO | WO 2015/183890 | 12/2015 |
| WO | WO 2015/195509 | 12/2015 |
| WO | WO 2016/048995 | 3/2016 |
| WO | WO/2016/065106 | 4/2016 |
| WO | WO/2016/073855 | 5/2016 |
| WO | WO 2017/083276 | 5/2017 |
| WO | WO 2018/039557 | 3/2018 |
| WO | WO 2018/044778 | 3/2018 |

OTHER PUBLICATIONS

Lindor, "Ursodeoxycholic acid for the treatment of primary biliary cirrhosis," New Engl J Med, 11(357; 15) 1524-1529 (2007).
Pusl et al., "Intrahepatic cholestasis of pregnancy," Orphanet Journal of Rare Diseases 2:26 (2007).
Walters et al., "Managing bile acid diarrhoea," Ther. Adv. Gastroenterol. 3(6): 349-357 (2010).
Zhou et al.. "Separating Tumorigenicity from Bile Acid Regulatory Activity for Endocrine Hormone FGF19," Cancer Research, 74 (12): 3306-3316 (2014).
Zhou et al., "Engineered fibroblast growth factor 19 reduces liver injury and resolves sclerosing cholangitis in Mdr2-deficient mice," Hepatology, 63 (3): 914-929 (2016).
Beenken et al, "The FGF family: biology, pathophysiology and therapy," Nat. Rev. Drug Discov., 8:235-253 (2009).
Bromberg et al., "Stat3 as an oncogene," Cell, 98:295-303 (1999).
Calvisi et al., "Ubiquitous activation of Ras and Jak/Stat pathways in human HCC," Gastroenterol., 130:1117-1128 (2006).
Camilleri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandom Mass Spectrometry," Neurogastroenterol Motil. 21(7):734-e43 (2009).
Chen et al., "Soluble FGFR4 extracellular domain inhibits FGF19-induced activation of FGFR4 signaling and prevents nonalcoholic fatty liver disease," Biochem. Biophys. Res. Comm. 409:651-656 (2011).
Chen et al., "Sorafenib overcomes TRAIL resistance of hepatocellular carcinoma cells through the inhibition of STAT3," Clin. Cancer Res,16:5189-5199 (2010).
Claudel et al., "Role of Nuclear Receptors for Ble Acid Metabolism, Bile Secretion, Cholestasis, and Gallstone Disease," Biochim. Biophys. Acta 1812:867-878 (2011).
Desnoyers et al., "Targeting FGF19 inhibits tumor growth in colon cancer xenograft and FGF19 transgenic hepatocellular carcinoma models," Oncogene 27:85-97 (2008).
Ďurovcová et al., "Plasma Concentration of Fibroblast Growth Factors 21 and 19 in Patients with Cushing's Syndrome," Physiol. Res. 59:415-422 (2010).
Foltz et al., "Treating Diabetes and Obesity with an FGF21-Mimetic Antibody Activating the βKlotho/FGFR1c Receptor Complex," Sci. Transl. Med. 4:162ra153; pp. 1-10 (2012).
Foltz et al., "Supplementary Materials for: Treating Diabetes and Obesity with an FGF21-Mimetic Antibody Activating the βKlotho/FGFR1c Receptor Complex," Sci. Transl. Med. 4:162ra153; pp. 1-13 (2012).
French et al., "Targeting FGFR4 Inhibits Hepatocellular Carcinoma in Preclinical Mouse Models," PLoS One 7(5):e36713 (2012).
Ge et al., "Characterization of a FGF19 Variant with Altered Receptor Specificity Revealed a Central Role for FGFR1c in the Regulation of Glucose Metabolism," PLoS One 7(3):e33603 (2012).
Harmer et al., "The Crystal Structure of Fibroblast Growth Factor (FGF) 19 Reveals Novel Features of the FGF Family and Offers a Structural Basis for Its Unusual Receptor Affinity," Biochemistry 43:629-640 (2004).
Hasegawa, "The expansion of PROMININ-1-positive epithelial-mesenchymal cells within periportal fibrosis of rotavirusinduced biliary atresia," Hepatol. 58:802A (2013).
He et al., "NF-κB and STAT3—key players in liver inflammation and cancer," Cell Res., 21:159-168 (2011).
He et al., "Hepatocyte IKKbeta/NF-kappaB inhibits tumor promotion and progression by preventing oxidative stress-driven STAT3 activation," Cancer Cell, 17: 286-297 (2010).
He et al., "Identification of liver cancer progenitors whose malignant progression depends on autocrine IL-6 signaling," Cell, 155:384-396 (2013).

(56) References Cited

OTHER PUBLICATIONS

Hofmann et al., "Chronic diarrhea due to excessive bile acid synthesis and not defective ileal transport: a new syndrome of defective FGF19 release," Clin Gastroenterol Hepatol. 7(11): 1151-1154 (2009).
Holt et al., "Definition of a novel growth factor-dependent signal cascade for the suppression of bile acid biosynthesis," Genes Dev., 17:1581-1591 (2003).
Ikeda et al., "Leptin receptor somatic mutations are frequent in HCV-infected cirrhotic liver and associated with hepatocellular carcinoma," Gastroenterol., 146:222-232 (2014).
Inagaki et al., "Fibroblast Growth Factor 15 Functions as an Enterohepatic Signal to Regulate Bile Acid Homeostasis," Cell Metabolism 2:217-225 (2005).
Kakumu et al., "Interleukin 6 production by peripheral blood mononuclear cells in patients with chronic hepatitis B virus infection and primary biliary cirrhosis," Gastroenterologia Japonica, 28:18-24 (1993).
Karras et al., "STAT3 regulates the growth and immunoglobulin production of BCL(1) B cell lymphoma through control of cell cycle progression," Cellular immunol., 202:124-135 (2000).
Kenakin et al., "Signalling bias in new drug discovery: detection, quantification and therapeutic impact," Nat. Rev. Drug Discov., 12:205-521 (2013).
Kir et al., "Roles of FGF19 in Liver Metabolism," Cold Spring Harb. Symp. Quant. Biol. 76:139-144 (2011).
Kurosu et al., "Tissue-specific Expression fo βKlotho and Fibroblast Growth Factor (FGF) Receptor Isoforms Determines Metabolic Activity of FGF19 and FGF21," J. Biol. Chem. 282(37):26687-26695 (2007).
Kurosu et al., "Supplemental Data for: Tissue-specific Expression fo βKlotho and Fibroblast Growth Factor (FGF) Receptor Isoforms Determines Metabolic Activity of FGF19 and FGF21," J. Biol. Chem. (2007) (available at: http://www.jbc.org/content/suppl/2007/07/11/M704165200.DC1/Kurosu_Suppl_Data.pdf (last visited Jul. 23, 2014).
Lin et al., "The STAT3 inhibitor NSC 74859 is effective in hepatocellular cancers with disrupted TGF-beta signaling," Oncogene, 28:961-972 (2009).
Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.
Ling et al., NGM Biopharmaceuticals, Identification of Gut Factors that Mimic the Metabolic Benefits of Gastric Bypass Surgery, p. 1, Jun. 8-12 (2012) Abstract.
Luo et al., "A nontumorigenic variant of FGF19 treats cholestatic liver diseases," Sci Transl Med 6, 247ra100 (2014).
Micanovic et al., "Different roles of N- and C-termini in the functional activity of FGF21," J. Cell. Physiol. 219:227-234 (2009).
Miyata et al., "Involvement of Multiple Elements in FXR-mediated Transcriptional Activation of FGF19," J. Steroid Biochm. Mol. Biol. 132:41-47 (2012).
Nicholes et al., "A Mouse Model of Hepatocellular Carcinoma: Ectopic Expression of Fibroblast Growth Factor in Skeletal Muscle of Transgenic Mice," Amer. J. Pathol., 160: 2295-2307 (2002).
Noguchi et al., "PDX-1 protein containing its own antennapedia-like protein transduction domain can transduce pancreatic duct and islet cells," Diabetes 52(7):1732-1737 (2003).
Ogawa et al., "BetaKlotho is Required for Metabolic Activity of Fibroblast Growth Factor 21," Proc. Natl. Acad. Sci. USA. 104:7432-7437 (2007).
Pai et al., "Antibody-Mediated Inhibition of Fibroblast Growth Factor 19 Results in Increased Bile Acids Synthesis and Ileal Malabsorption of Bile Acids in Cynomolgus Monkeys," Toxicological Sciences. 3:E18 (2012).
Pattni et al., "Fibroblast Growth Factor 19 and 7α-Hydroxy-4-Cholesten-3-one in the Diagnosis of Patients With Possible Bile Acid Diarrhea," Clinical and Translational Gastroenterology. 26:312-324 (2012).

Potthoff et al., "Endocrine Fibroblast Growth Factors 15/19 and 21: From Feast to Famine," Genes Dev. 26:312-324 (2012).
Rivera et al., "Long-term regulated expression of growth hormone in mice after intramuscular gene transfer," PNAS, 96:8657-8662 (1999).
Rose et al., "Molecular Control of Systemic Bile Acid Homeostasis by the Liver Glucocorticoid Receptor," Cell Metabolism 14:123-130 (2011).
Ryan et al., "FXR is a Molecular Target for the Effects of Vertical Sleeve Gastroectomy," Nature 509(7499):183-188 (2014); epub ahead of print Mar. 26, 2014.
Sawey et al., "Identification of a Therapeutic Strategy Targeting Amplified FGF19 in Liver Cancer by Oncogenomic Screening," Oncogene 27, 85-97 (2011).
Schaap et al., "High expression of the bile salt-homeostatic hormone fibroblast growth factor 19 in the liver of patients with extrahepatic cholestasis," Hepatol., 49:1228-1235 (2009).
Schaap, "Role of Fibroblast Growth Factor 19 in the Control of Glucose Homeostasis," Curr. Opin. Clin. Nutr. Metab. Care 15(4):386-391 (2012).
Storer et al., "An industry perspective on the utility of short-term carcinogenicity testing in transgenic mice in pharmaceutical development," Toxicologic Pathol., 38:51-61 (2010).
Tartaglia et al., "Identification and expression cloning of a leptin receptor, OB-R," Cell, 83:1263-1271 (1995).
Tomlinson et al., "Transgenic Mice Expressing Human Fibroblast Growth Factor-19 Display Increased Metabolic Rate and Decreased Adiposity," Endocrinology 143(5):1741-47 (2002).
Trehin et al., "Cellular uptake but low permeation of human calcitonin-derived cell penetrating peptides and Tat(47-57) through well-differentiated epithelial models," Pharm. Research, 21:1248-1256 (2004).
Walters, "A variant of FGF19 for treatment of disorders of cholestasis and bile acid metabolism," Ann. Transl. Med. 3(S1):S7 (2015).
Wang et al., "Leptin in hepatocellular carcinoma," World J. Gastroenterol., 16:5801-5809 (2010).
Wu et al., "C-terminal Tail of FGF19 Determines Its Specificity toward Klotho C-receptors," J. Biol. Chem. 283(48):33304-33309 (2008).
Wu et al., "Role of FGF19 Induced FGFR4 Activation in the Regulation of Glucose Homeostasis," Aging 1(12):1023-1027 (2009).
Wu et al., "Selective Activation of FGFR4 by an FGF19 Variant Does Not Improve Glucose Metabolism in ob/ob Mice," Proc. Natl. Acad. Sci. USA 106(34):14379-14384 (2009).
Wu et al., "FGF19-induced Hepatocyte Proliferation is Mediated Through FGFR4 Activation," J. Biol. Chem. 285(8):5165-5170 (2010).
Wu et al., "Separating Mitogenic and Metabolic Activities of Fibroblast Growth Factor 19 (FGF19)," Proc. Natl. Acad. Sci. USA 107(32):14158-14163 (2010).
Wu et al., "Therapeutic Utilities of Fibroblast Growth Factor 19," Expert Opin. Ther. Targets 15(11):1307-1316 (2011).
Wu et al., "FGF19 Regulates Cell Proliferation, Glucose and Bile Acid Metabolism via FGFR4-Dependent and Independent Pathways," PLoS One 6(3):e17868 (2011).
Xie et al., "FGF-19, A Novel Fibroblast Growth Factor with Unique Specificity for FGFR4," Cytokine 11(10):729-735 (1999).
Zaiss et al., "Differential activation of innate immune responses by adenovirus and adeno-associated virus vectors," J. Virol., 76:4580-4590 (2002).
Zender et al., "VP22-mediated intercellular transport of p53 in hepatoma cells in vitro and in vivo ," Cancer Gene Ther., 9(6):489-496 (2002).
Zhang et al., "Adenovirus-adeno-associated virus hybrid for large-scale recombinant adeno-associated virus production," Hum. Gene Ther., 20:922-929 (2009).
Zincarelli et al., "Analysis of AAV serotypes 1-9 mediated gene expression and tropism in mice after systemic injection," Mol. Ther., 16:1073-1080 (2008).
Angulo et al., "Liver Fibrosis, but No Other Histologic Features, Is Associated With Long-term Outcomes of Patients With Nonalcoholic Fatty Liver Disease," *Gastroenterology*, 149:389-397 (2015).

(56) References Cited

OTHER PUBLICATIONS

Camilleri et al., "Effect of increased bile acid synthesis or fecal excretion in irritable bowel syndrome-diarrhea," *Am. J. Gastroenterol.*, 109:1621-1630 (2014).

Dichenko et al., "Sat-374: Steroid 7 Alpha-Hydroxylases: Neurosteroids Activation and Cholesterol Catabolism," The Endocrine Society's 95th Annual Meeting and Expo, San Francisco, Abstract, Jun. 15-18, 2013.

Kaushik et al., "Why is Trehalose an Exceptional Protein Stabilizer?," *J. Biol. Chem.*, 278(29):26458-26465 (2003).

Le et al., "Management of non-alcoholic fatty liver disease and steatohepatitis," *J. Clin. Exp. Hepatol.*, 2:156-173 (2012).

Lin et al., "Adiponectin mediates the metabolic effects of FGF21 on glucose homeostasis and insulin sensitivity in mice," *Cell. Metab.*, 17:779-789 (2013).

Mudaliar et al., "Efficacy and safety of the farnesoid X receptor agonist obeticholic acid in patients with type 2 diabetes and non-alcoholic fatty liver disease," *Gastroenterology*, 145:574-582 (2013).

Nguyen et al., "Purification of cholesterol 7 alpha-hydroxylase from human and rat liver and production of inhibiting polyclonal antibodies," *J. Biol. Chem.*, 265:4541-4546 (1990).

Oduyebi et al., "Effects of NGM282, an FGF19 variant, on colonic transit and bowel function in functional constipation: a randomized phase 2 trial," *Am. J. Gastoenterol.*, 113:725-734 (2018).

Rossi et al., "P1313 Ngm282, a Novel Specific Inhibitor of Cyp7a1-Mediated Bile Acid Synthesis, is Safe and Well Tolerated with Predictable Pharmacokinetics in Healthy Human Subjects," *J. Hepatology*, 60(1):S533 (2014).

"TaqMan SNP Genotyping Assays," Life Technologies Corporation (2012).

Tokuriki et al., "Stability effects of mutations and protein evolvability," *Curr. Opin. Struct. Biol.*, 19(5):596-604 (2009).

Walters, "Bile acid diarrhoea and FGF19: new views on diagnosis, pathogenesis and therapy," *Nat. Rev. Gastroenterol. Hepatol.*, 11(7):426-434 (2014).

Wender et al., "The design, synthesis, and evaluation of molecules that enable or enhance cellular uptake: peptoid molecular transporters," *Proc. Natl. Acad. Sci. USA*, 97:13003-13008 (2000).

Wong et al, "Pharmacogenetics of the effects of colesevelam on colonic transit in irritable bowel syndrome with diarrhea," *Dig. Dis. Sci.*, 57(5):1222-1226 (2012).

Zhou et al., "Serum tumor markers for detection of hepatocellular carcinoma," *World J. Gastroenterol.*, 12(8):1175-1181 (2006).

FGF19 (SEQ ID NO:42):

RPLAFSDAGPHVHYGWGDPIRLRHLYTSGPHGLSSCFLRIRADGVV
DCARGQSAHSLLEIKAVALRTVAIKGVHSVRYLCMGADGKMQGLL
QYSEEDCAFEEEIRPDGYNVYRSEKHRLPVSLSSAKQRQLYKNRGFL
PLSHFLPMLPMVPEEPEDLRGHLESDMFSSPLETDSMDPFGLVTGLE
AVRSPSFEKDYKDDDDK

FIG.1

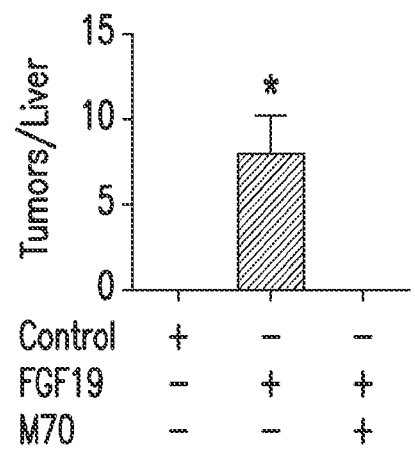
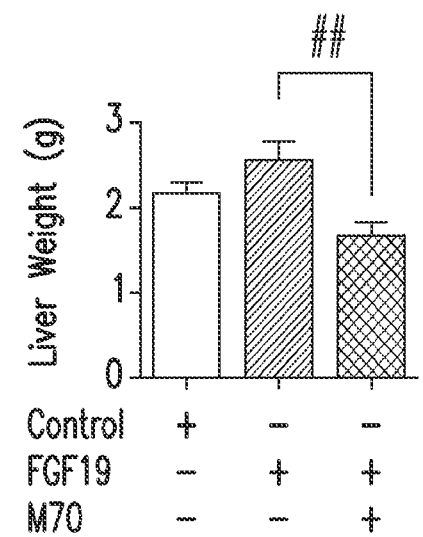
FIG.11A    FIG.11B
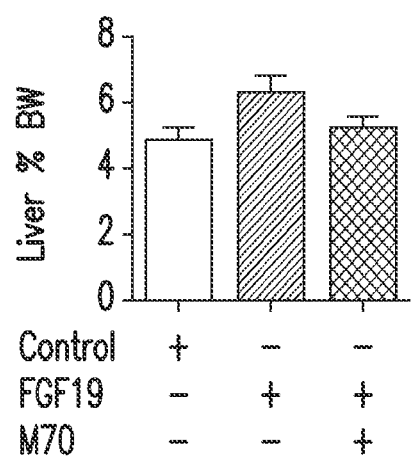
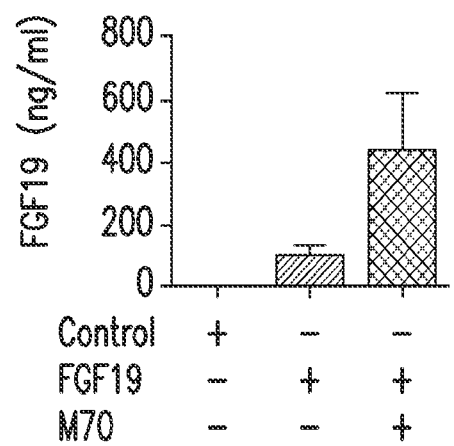
FIG.11C    FIG.11D

METHODS OF USING VARIANTS OF FGF19 POLYPEPTIDES FOR THE TREATMENT OF CANCER

CROSS-REFERENCE TO RELATED APPLICATIONS

This application is a 371 national stage application of international application Serial No. PCT/US2014/062378 filed Oct. 27, 2014, which claims the benefit of U.S. Ser. No. 61/896,473 filed Oct. 28, 2013; U.S. Ser. No. 61/922,586 filed Dec. 31, 2013; and U.S. Ser. No. 62/067,273 filed Oct. 22, 2014, each of which is incorporated herein by reference in its entirety.

FIELD

The invention relates to, among other things, models useful in determining whether polypeptide variants of a fibroblast growth factor having glucose-lowering activity also exhibit favorable oncology-related profiles, and methods and uses involving the foregoing. Also provided are methods of antagonizing the oncogenic activity of FGF19 in a subject and, in certain embodiments, methods of preventing or treating a disease, disorder or condition, such as a FGF19-dependent disease, disorder or condition, or a symptom thereof.

BACKGROUND

Diabetes mellitus is a debilitating metabolic disease caused by the absence of insulin production (type 1), or insulin resistance or insufficient insulin production (type 2) from pancreatic $\beta$-cells, endocrine cells that manufacture and store insulin for release following a meal. High blood glucose levels stimulate the secretion of insulin by pancreatic $\beta$-cells. Insulin, in turn, stimulates the entry of glucose into muscles and adipose cells, leading to the storage of glycogen and triglycerides and to the synthesis of proteins. Activation of insulin receptors on various cell types diminishes circulating glucose levels by increasing glucose uptake and utilization, and by reducing hepatic glucose output. Disruptions within this regulatory network can result in diabetes and associated pathologic conditions.

An individual having a glucose metabolism disorder can suffer from hyperglycemia, hyperinsulinemia, and/or glucose intolerance, along with a host of related disorders. For example, insulin resistance, a disorder often associated with aberrant levels of glucose and/or insulin, is characterized by hepatic, fat, and muscle cells losing their ability to respond to normal blood insulin levels. Such glucose metabolism disorders adversely affect a large and growing number of individuals throughout the world.

Obesity, which is most commonly caused by excessive food intake coupled with limited energy expenditure and/or lack of physical exercise, often accompanies various glucose metabolism disorders. Obesity increases the likelihood of an individual developing various diseases, such as diabetes mellitus, hypertension, atherosclerosis, coronary artery disease, gout, rheumatism and arthritis. Moreover, mortality risk directly correlates with obesity, such that, for example, a body-mass index in excess of 40 results in an average decreased life expectancy of more than 10 years.

Certain pharmacological treatment modalities have demonstrated, to varying degrees, both glucose homeostatic and anti-obesity activity. Unfortunately, such modalities are frequently associated with serious and often debilitating adverse effects.

In view of the prevalence and severity of diabetes, obesity, and associated metabolic and non-metabolic disorders, along with the shortcomings of current treatment options, alternative treatment modalities are needed.

SUMMARY

Bariatric surgery has been proposed as an alternative, non-pharmacological treatment for diabetes. It has been postulated that changes in gut hormone secretion following surgery are responsible for the resolution of diabetic conditions. Serum levels of Fibroblast Growth Factor 19 (FGF19) in humans are elevated following gastric bypass surgery. FGF19 is highly expressed in the distal small intestine, and transgenic over-expression of FGF19 improves glucose homeostasis (Tomlinson, E. (2002) Endocrinology 143(5): 1741-47). Augmented expression and secretion of FGF19 could at least partially explain the remission of diabetes observed following surgery.

Despite the desirable metabolic effects attributable to FGF19 (e.g., blood glucose lowering), treatments that increase FGF19 levels (through, for example, enhancement of FGF19 expression or administration of exogenous FGF19) are associated with induction of hepatocellular carcinoma (HCC). Thus, there is an on-going effort to identify agents that possess the favorable characteristics of FGF19 without inducing cancerous conditions like HCC. The present disclosure is based, in part, on animal models and associated methods to assist in the accurate and efficient determination of whether a candidate agent possesses such attributes and whether a subject is a viable candidate for such treatment.

In further embodiments, a use or method of treatment of a subject is intended to or results in reduced glucose levels, increased insulin sensitivity, reduced insulin resistance, reduced glucagon, an improvement in glucose tolerance, or glucose metabolism or homeostasis, improved pancreatic function, or reduced triglyceride, cholesterol, intermediate density lipoproteins (IDL), low density lipoproteins (LDL) or very low density lipoproteins (VLDL) levels, or a decrease in blood pressure, a decrease in intimal thickening of the blood vessel, or a decrease in body mass or weight gain.

In one embodiment, the present disclosure contemplates a method for determining whether a test subject having a metabolic disorder is a candidate for treatment with a FGF19 variant, the method comprising a) co-administering FGF19 or a FGF19 surrogate, and a FGF19 variant to the test subject having a metabolic disorder, wherein the amount of the FGF19 or the FGF19 surrogate administered to the test subject is sufficient to induce a cancerous condition in a reference population, and b) determining whether an indicia of a cancerous condition is observed in the test subject; wherein the absence of an indicia of a cancerous condition indicates that the test subject is a candidate for treatment with a FGF19 variant.

As used herein, the term "FGF19 surrogate" is meant to include any molecule (e.g., a polypeptide) capable of eliciting a same or a comparable effect as FGF19, wherein the effect is generally cancer-related (e.g., the induction of tumor formation or any other indicia of a cancerous condition). An FGF19 surrogate is frequently a variant of FGF19, including active fragments, having at least about 75%, at least about 80%, at least about 85%, at least about 90%, at least about 93%, at least about 95%, at least about 96%, at least about 97%, at least about 98%, or at least about 99%, amino acid sequence identity to a contiguous stretch of from about 150 amino acids to about 160 amino acids, from about 160 amino acids to about 170 amino acids, from about 170 amino acids to about 180 amino acids, from about 180 amino acids to about 190 amino acids, or about 194 amino acids or more, of one of the amino acid sequences described herein.

In the present disclosure, the phrase "an indicia of a cancerous condition" broadly refers to any indication that a cancerous disease, disorder or condition has formed, is forming or is likely to form. Most cancers are initially recognized either because of the appearance of signs or symptoms or through screening. Definitive diagnoses generally require, among other means, one or more of pathological examination of a tissue sample, blood tests, x-rays, CT scans and endoscopy. Cancerous conditions refer to any type or classification of cancer, including carcinomas, sarcomas, lymphomas and leukemias, and blastomas.

Cancer symptoms are usually caused by the effect of a cancer on the part of the body where it is forming (e.g., unusual lumps on the breasts or changes in moles on the skin), although cancerous diseases, disorders and/or conditions may cause more general symptoms such as weight loss or fatigue. In the methods and models described herein, an indicia of a cancerous condition (or disorder or disease) is frequently a tumor (e.g., a colon tumor or a hepatic tumor). Observations and measurements of a reduction in tumor number, tumor size, or tumor weight frequently indicate that a treatment modality is having a positive effect.

In particular embodiments, the indicia of a cancerous condition is/are associated with hepatocellular carcinoma (HCC, also referred to as malignant hepatoma), the most common type of liver cancer. HCC may present with jaundice, bloating from ascites, easy bruising from blood clotting abnormalities, loss of appetite, weight loss, abdominal pain, nausea, emesis or fatigue. HCC is discussed further hereafter.

In another embodiment, the present disclosure contemplates a method for determining whether a test subject having a metabolic disorder is a candidate for treatment with a FGF19 variant, the method comprising a) providing a test subject having an indicia of a cancerous condition, the subject having a metabolic disorder, b) co-administering FGF19 or a FGF19 surrogate, and a FGF19 variant to the test subject, wherein the amount of the FGF19 or the FGF19 surrogate administered to the test subject is sufficient to induce a cancerous condition in a reference population, and c) determining whether an indicia of a cancerous condition is enhanced in the test subject; wherein the absence of enhancement of an indicia of a cancerous condition indicates that the test subject is a candidate for treatment with a FGF19 variant.

In a further embodiment, the present disclosure contemplates a method for determining whether a test subject having a metabolic disorder is a candidate for treatment with a FGF19 variant, the method comprising a) providing a test subject having an indicia of a cancerous condition, the test subject having a metabolic disorder, b) and co-administering FGF19 or a FGF19 surrogate, and a FGF19 variant to the test subject, wherein the amount of the FGF19 or the FGF19 surrogate is administered to the test subject is sufficient to induce a cancerous condition in a reference population, and c) determining whether an indicia of a cancerous condition is reduced in the test subject; wherein the reduction of an indicia of a cancerous condition indicates that the test subject is a candidate for treatment with a FGF19 variant.

The present disclosure also contemplates a method for determining whether a FGF19 variant is a candidate for treating a test subject having a metabolic disorder, the method comprising co-administering FGF19 or a FGF19 surrogate, and the FGF19 variant to the test subject having a metabolic disorder, wherein the amount of the FGF19 or the FGF19 surrogate administered to the test subject is sufficient to induce a cancerous condition in a reference population, and determining whether an indicia of a cancerous condition is observed in the test subject; wherein the absence of an indicia of a cancerous condition indicates that the FGF19 variant is a candidate for treatment of the test subject.

Other embodiments contemplated herein are drawn to a method for determining whether a FGF19 variant is a candidate for treating a test subject having a metabolic disorder, the method comprising providing a test subject having a metabolic disorder, the test subject having an indicia of a cancerous condition, ω-administering FGF19 or a FGF19 surrogate, and a FGF19 variant to the test subject, wherein the amount of the FGF19 or the FGF19 surrogate is administered to the test subject is sufficient to exacerbate a cancerous condition in a reference population, and determining whether an indicia of a cancerous condition is enhanced in the test subject; wherein the absence of exacerbation of an indicia of a cancerous condition indicates that the FGF19 variant is a candidate for treatment of the test subject. In particular embodiments, one or more indicia of a cancerous condition are reduced in the test subject.

In still further embodiments, the present disclosure contemplates a method of treating (or preventing, in certain circumstances) a subject having a metabolic disorder, the method comprising providing a subject having a metabolic disorder, wherein the subject exhibits an indicia of a FGF19-induced cancerous condition, and administering to the subject a therapeutically effective amount of a FGF19 variant identified from a pool of candidate FGF19 variant polypeptides as described herein; wherein there is an improvement in the metabolic disorder in the subject.

As alluded to above, the present disclosure also contemplates various models. One embodiment is directed to a model for determining whether a FGF19 variant is a candidate for preventing a cancerous disease, disorder or condition in a subject having a metabolic disorder, the model comprising a subject that i) does not exhibit an indicia of a cancerous condition prior to the administration of an effective amount of a FGF19 or FGF19 surrogate, and ii) exhibits an indicia of a cancerous condition after the administration of FGF19 or FGF19 surrogate; and wherein an indicia of a cancerous condition improves upon administration of an effective amount of a polypeptide comprising an amino acid sequence set forth in SEQ ID NO:1. In certain embodiments, the polypeptide consists of an amino acid sequence set forth in SEQ ID NO:1.

The present disclosure also contemplates a model for determining whether a FGF19 variant is a candidate for treating a cancerous disease, disorder or condition in a subject having a metabolic disorder, the model comprising a subject having at least one indicia of cancer resulting from administration of FGF19 or FGF19 surrogate, wherein the indicia of cancer improves upon administration of an effective amount of a polypeptide comprising an amino acid sequence set forth in SEQ ID NO:1. In certain embodiments, the polypeptide consists of an amino acid sequence set forth in SEQ ID NO:1.

Though not limiting, in certain embodiments, the FGF19 variant is M70 (SEQ ID NO:1) in the methods and models of the present disclosure. An FGF19 variant can be identified from a pool of candidate FGF19 variant polypeptides, wherein an identified FGF19 variant improves at least one condition of, for example, a hyperglycemic condition (e.g., diabetes), insulin resistance, hyperinsulinemia, glucose intolerance, metabolic syndrome, obesity or an undesirable body mass. Additional examples of metabolic disorders, diseases and conditions are described hereafter.

In certain embodiments of the methods and models described herein, the subject (e.g., a test subject) is an animal (e.g., a rodent, or monkey), such as a mouse (e.g., a db/db mouse). Depending on the context in which the term is used, a subject can also be a human. In some embodiments, the subject has an increased level of mature FGF19 compared to the level of mature FGF19 in a sample population, wherein the sample population can be any group of members useful as a baseline, reference, etc. In some embodiments, the increased level of mature FGF19 is due to over-expression.

In some embodiments, the FGF19, a FGF19 surrogate, and/or FGF19 variant is labeled, for example, to facilitate detection, purification and the like. In certain embodiments, the FGF19, a FGF19 surrogate, and/or FGF19 variant is labeled through a covalent bond. The skilled artisan is familiar with different types of labels and uses thereof. Labeling is most frequently effected at the N-terminus and/or C-terminus of a polypeptide, but it can also occur within the polypeptide. The present disclosure contemplates the use of any direct and indirect labeling techniques, which can be carried out in vivo, in vitro, etc.

In the methods and models of the present disclosure, the steps associated with determining an indicia of a cancerous condition, disorder or disease, can be performed at any time that can allow the cancerous condition, disorder or disease to manifest itself and thus be detected. By way of example, the determination can occur more than 3 months, more than 20 weeks, more than 6 months, more than 9 months, or more than 12 months after the aforementioned co-administration steps. In particular embodiments, FGF19 is co-administered with the FGF19 variant.

The present disclosure also contemplates a method of antagonizing the oncogenic activity of FGF19. In certain embodiments, provided herein is a method of antagonizing the oncogenic activity of FGF19 in a subject, comprising administering to the subject a therapeutically effective amount of a FGF19 variant, thereby antagonizing the oncogenic activity of FGF19 in the subject. In certain embodiments, the subject has a metabolic disorder and/or an indicia of a cancerous condition.

The present disclosure further contemplates a method of preventing or treating a FGF19-dependent disease, disorder or condition, or a symptom thereof, in a subject, comprising administering to the subject a therapeutically effective amount of a FGF19 variant, wherein the disease, disorder or condition thereof in the subject. is prevented or treated. In certain embodiments, there is an improvement in the disease, disorder, condition or symptom thereof in the subject. In certain embodiments, the subject has a metabolic disorder and/or an indicia of a cancerous condition. In a specific embodiment, the FGF19-dependent disease, disorder or condition is a cancer or tumor. In some embodiments, the cancer or tumor is a liver cancer or tumor. In certain embodiments, the cancer or tumor is a colon cancer or tumor. In other embodiments, the cancer or tumor is a prostate cancer or tumor. In yet other embodiments, the cancer or tumor is a lung cancer or tumor. In certain embodiments, the subject is a subject in need of prevention or treatment thereof. In a specific embodiment, the FGF19 variant is a polypeptide comprising or consisting of an amino acid sequence set forth in SEQ ID NO:1 (M70).

BRIEF DESCRIPTION OF THE DRAWINGS

FIG. 1 depicts the amino acid sequences of mature human FGF19. The amino acid residues corresponding to the flag epitope are underlined.

hematoxylin and eosin (H & E) staining of liver tissue sections; immunohistochemical detection of Ki-67 and glutamine synthetase. Tumors (T) are outlined by dotted lines. Scale bars, 100 µm. (H) Serum levels of liver enzymes (ALKP: alkaline phosphatase; ALT, alanine aminotransferase; AST, aspartate aminotransferase; n=5 per group) were measured prior to termination of the study. All values represent mean±SEM. *p<0.05, p<0.01, *p<0.001 denotes significant differences vs. control group by one-way ANOVA followed by Dunnett's post test. See also Tables 3 and 4.

FIGS. 8A-8G depict no liver tumor formation in rasH2 mice treated with M70 for 52 weeks. (A)-(E) Growth curve (A), number of tumors per liver (B), liver weight (C), liver-to-body weight ratios (D), and serum levels of M70 or FGF19 (E) of rasH2 mice expressing FGF19 or M70 transgenes (n=9 per group) for 52 weeks. (F) Livers were collected 52 weeks after AAV administration and stained with H & E or anti-glutamine synthetase, a marker for FGF19-induced liver tumors. The sections stained for glutamine synthetase were taken from an area near the paired section stained with H & E and showed the same portal (p) and central (c) veins. Tumors (T) are outlined by dotted lines. Scale bars, 100 µm. (G) qRT-PCR analysis of Ki-67 and AFP expression in the liver. mRNA abundance was normalized to GAPDH expression. All values represent mean±SEM. *p<0.05, p<0.01, *p<0.001 denotes significant differences vs. control group by one-way ANOVA followed by Dunnett's post test.

FIGS. 9A-9G depicts M70 binding and activation of FGFR4 in vitro. (A) Biacore SPR assay of the interaction between FGF19 and FGFR4-Fc chimeric proteins immobilized on flow cells. Left column shows binding curves obtained over a range of FGF19 concentrations (15.62-2000 nM at 2 fold dilutions), while right column shows the steady state fits of the data for obtaining $K_D$ values. (B) Binding of M70 to FGFR4 by Biacore. Similar procedures to (A) were used. (C) Solid phase binding of M70 or FGF19 to FGFR4-KLB receptor complex. The bound ligands were detected using a biotinylated FGF19-specific polyclonal antibody. (D) Relative luciferase activity after stimulation with M70 or FGF19 in L6 cells transiently transfected with FGFR4 in the presence or absence of KLB. (E) M70 induces ERK phosphorylation in Hep3B cells. (F) M70 repressed Cyp7a1 expression in primary hepatocytes of mouse, rat, and human origin. Relative expression of Cyp7a1 mRNA in hepatocytes were determined by qRT-PCR and normalized to 18S RNA (mouse and rat) or actin (human) mRNA levels. (G) Repression of hepatic Cyp7a1 expression by M70 in mice. 12-week-old db/db mice were injected intraperitoneally with recombinant M70 or FGF19 protein. Mice were euthanized 4 hours after dosing and hepatic Cyp7a1 expression was evaluated by qRT-PCR and normalized to 18S RNA expression. Dose response curves of Cyp7a1 repression in mice were shown. All values represent mean±SEM.

Figure 10A:
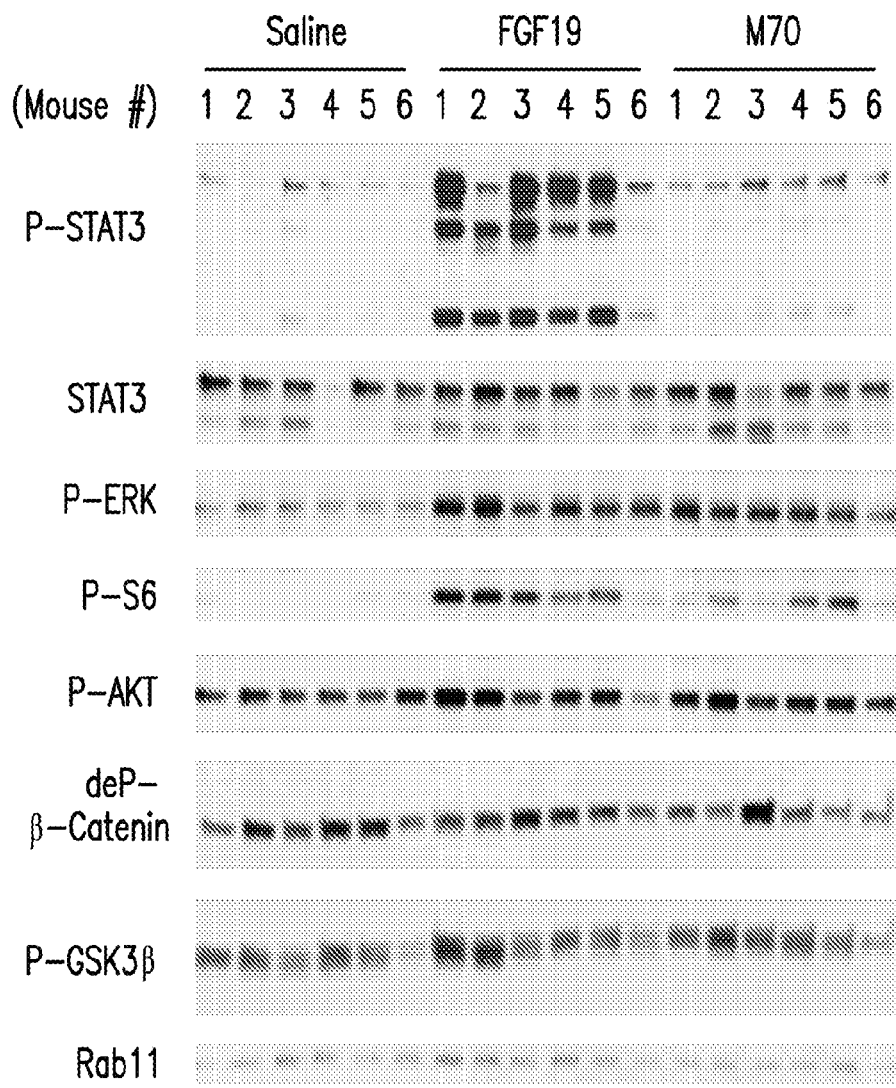
Figure 10B:
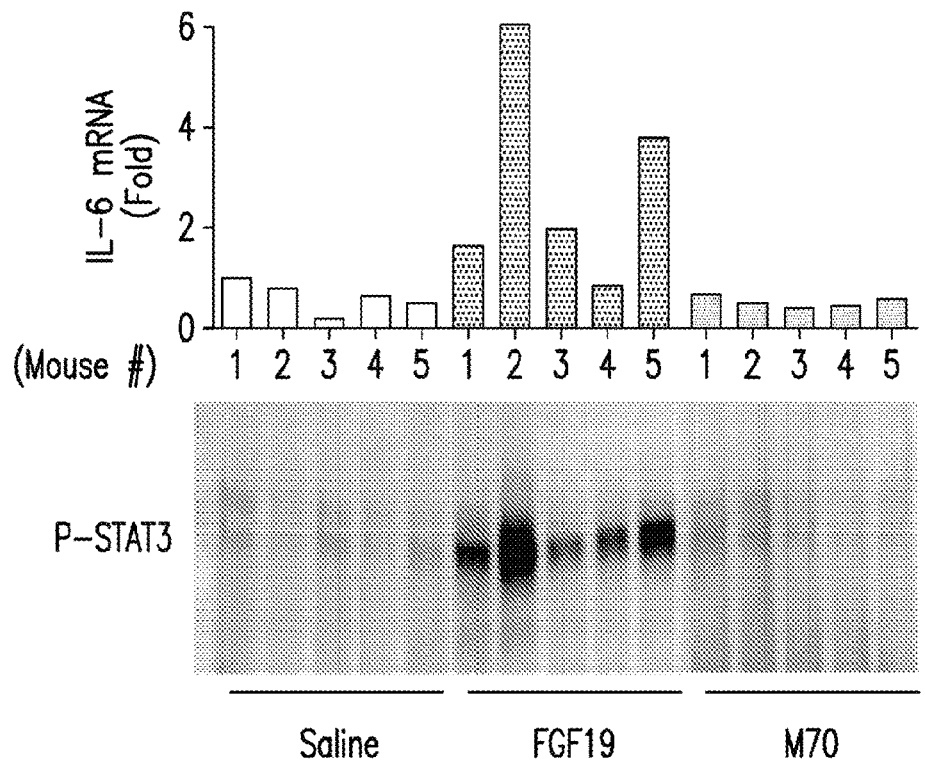
Figure 10C:
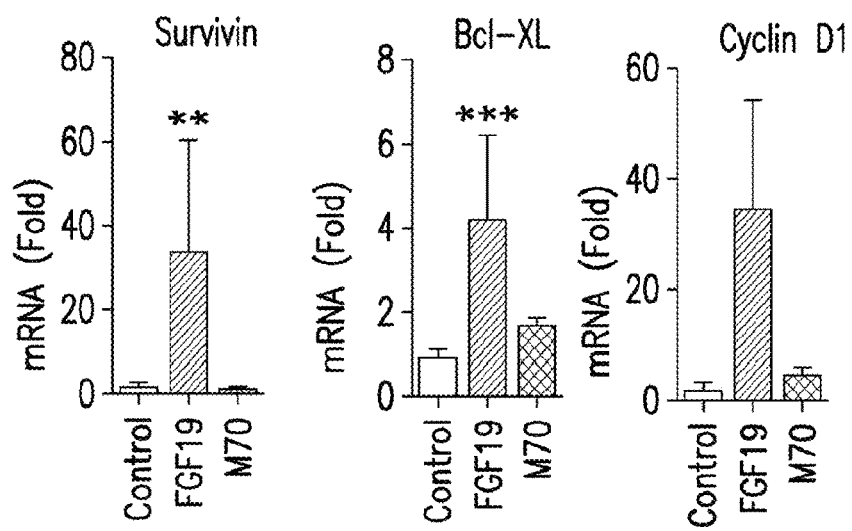

FIGS. 10A-10C depict the differential activation of cell signaling pathways by M70 and FGF19 in vivo. (A) Livers were harvested from db/db mice (n=6 per group) injected intraperitoneally with saline, 1 mg/kg FGF19 or 1 mg/kg M70 proteins 2 hours post injection. Liver lysates were examined by western blot for expression and phosphorylation of the indicated proteins. Each lane represents an individual mouse. Rab11 serves as a loading control. Note that hepatic STAT3 is activated by FGF19, not M70. (B) Mice treated with FGF19 exhibited elevated expression of IL-6 (a STAT3 inducer). Livers were harvested from db/db mice as in (A). IL-6 mRNA amounts in livers were measured by qRT-PCR and normalized to GAPDH expression. Results are represented as fold expression relative to saline-treated animals. Shown are the results for 5 separate mice per condition. STAT3 phosphorylation status by immunoblotting the liver lysates from the same animals is shown in the lower panel. (C) qPCR showing expression of mRNAs for STAT3 target genes (survivin, Bcl-$X_L$, and cyclin D1) in rasH2 mice 52 weeks following administration of AAV vectors expressing FGF19 or M70 transgenes. All values represent mean±SEM. p<0.01, *p<0.001 denotes significant differences vs. control group by one-way ANOVA followed by Dunnett's post test.

FIGS. 11A-11J depicts M70 inhibits FGF19-induced tumor growth in db/db mice and in xenograft models. (A)-(D) 11 week old db/db mice were injected with AAV-FGF19 ($3 \times 10^{10}$ genome copies) in the absence or presence of M70 ($3 \times 10^{11}$ genome copies). Liver tumor score (A), liver weight (B), ratio of liver to body weight (C) and serum levels of transgene expression (D) were determined 24 weeks later. *p<0.05 denotes significant differences vs. control group by one-way ANOVA followed by Dunnett's post test; ##p<0.01 denotes significant differences by two-tailed t test. (E) Histology of livers of mice expressing FGF19 or co-treated with M70. Liver sections were stained with H & E or anti-glutamine synthetase, a marker for FGF19-induced liver tumors. Tumors (T) are outlined by dotted lines. Scale bars, 100 µm. (F) FGF19 is produced and secreted by human cancer cell lines. FGF19 levels in culture supernatant are determined by ELISA. (G-J) M70 inhibits human cancer xenograft tumor growth in vivo. 8 week old athymic nu/nu mice were subcutaneously implanted with $5 \times 10^6$ Huh-7 (n=10) (G) or HCT-116 (n=5) (H-J) cells. Mice bearing established tumors of equivalent volumes (~100 mm³) were randomized into groups and treated with M70 via AAV-mediated gene delivery. A control virus (GFP) was also included in the study. Tumor growth was measured over the course of a 15-day treatment period. The image shows HCT-116 solid tumors dissected at end of the 15-day treatment period (I). Body weight gain of mice bearing HCT-116 tumor xenografts (J) were also determined. ***p<0.001 denotes significant differences vs. control group by two-way ANOVA followed by Bonferroni's post test. All values represent mean±SEM.

Figures 12A, 12B:
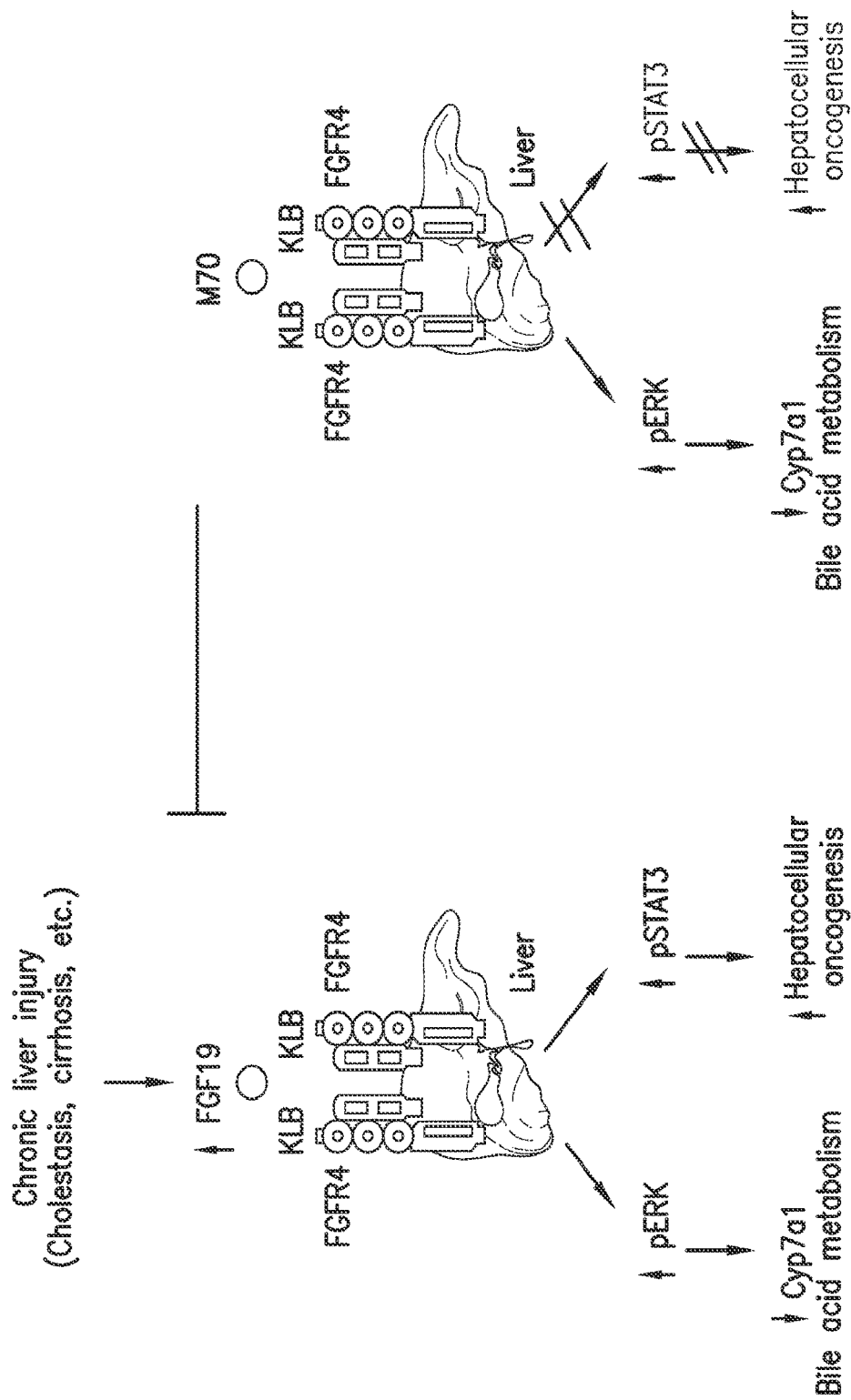

FIGS. 12A-12B depict a model of developing a FGF19 variant for treating FGF19-dependent tumors. (A) Chronic liver injury (cholestasis, cirrhosis, etc.) leads to FGF19 accumulation in the liver. While important for regulating bile acid synthesis, FGF19 also activates STAT3, a key transcription factor in promoting hepatocarcinogenesis. This contributes to tumor initiation, promotion, and progression into HCC. (B) M70 is an engineered variant of FGF19. As a selective modulator, M70 exhibits bias toward certain FGFR4 signaling pathways (i.e. pERK and Cyp7a1) to the relative exclusion of others (i.e., tumor). Moreover, M70 can inhibit the growth of tumors that are dependent on FGF19.

Figure 13A:
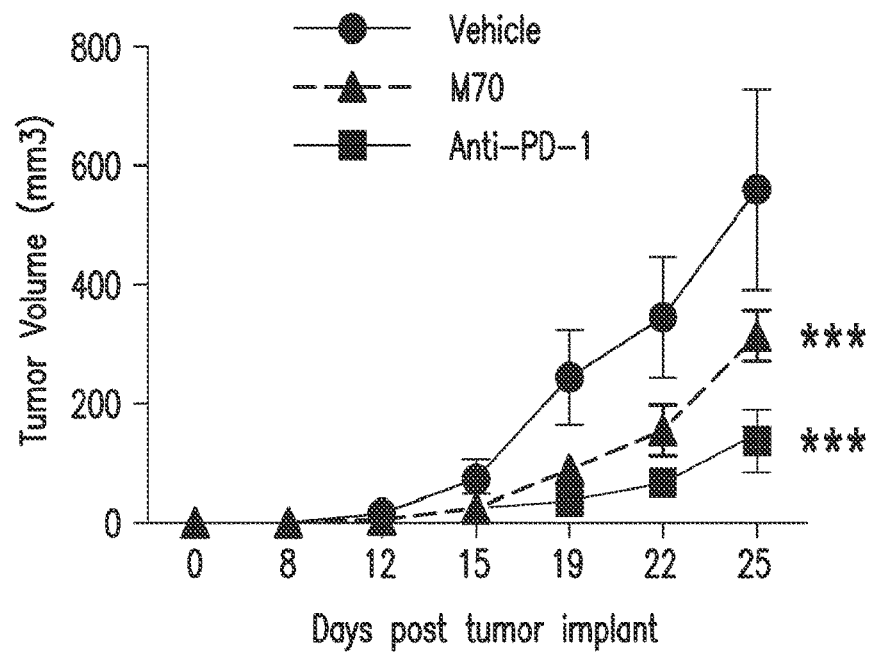
Figure 13B:
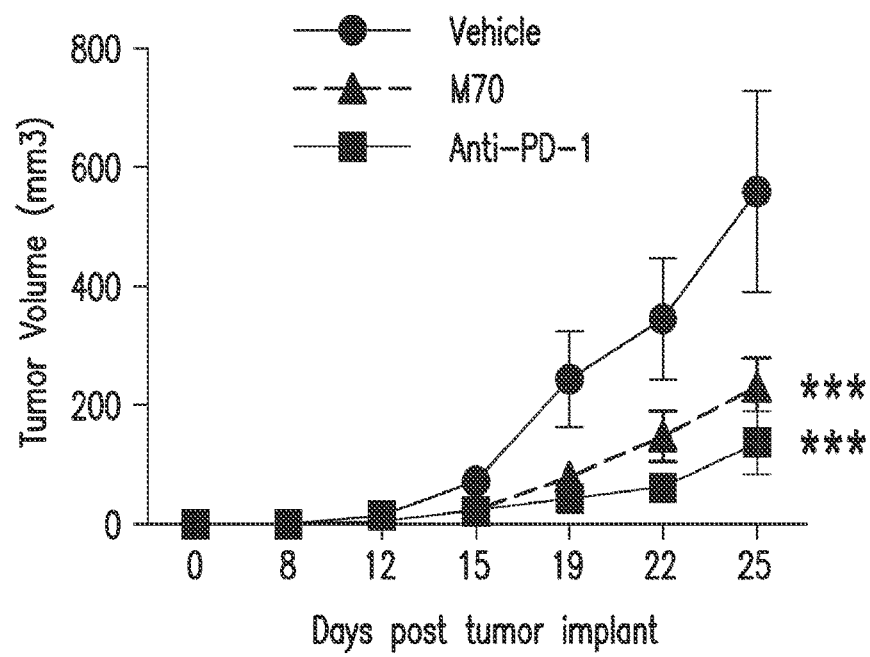

FIGS. 13A-13B depicts M70 delays tumor growth in a CT26 colon cancer syngenic mouse model. (A) M70 delays CT26 tumor growth following administration of 10 mg/kg doses. (B) M70 delays CT26 tumor growth following administration of 3 mg/kg doses. The p-values were determined by two-way ANOVA vs. vehicle-treated mice. *p<0.001; p<0.01.

Figure 14A:
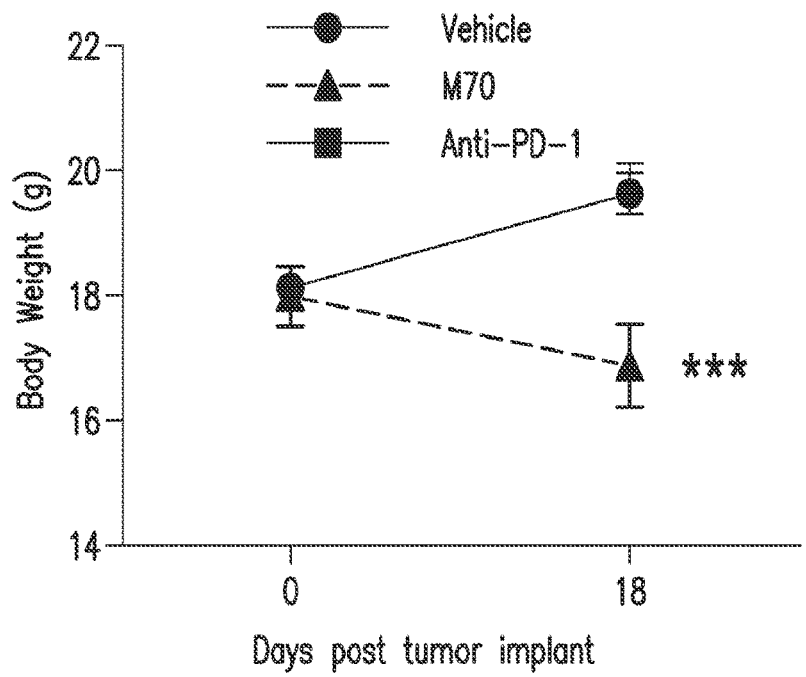
Figure 14B:
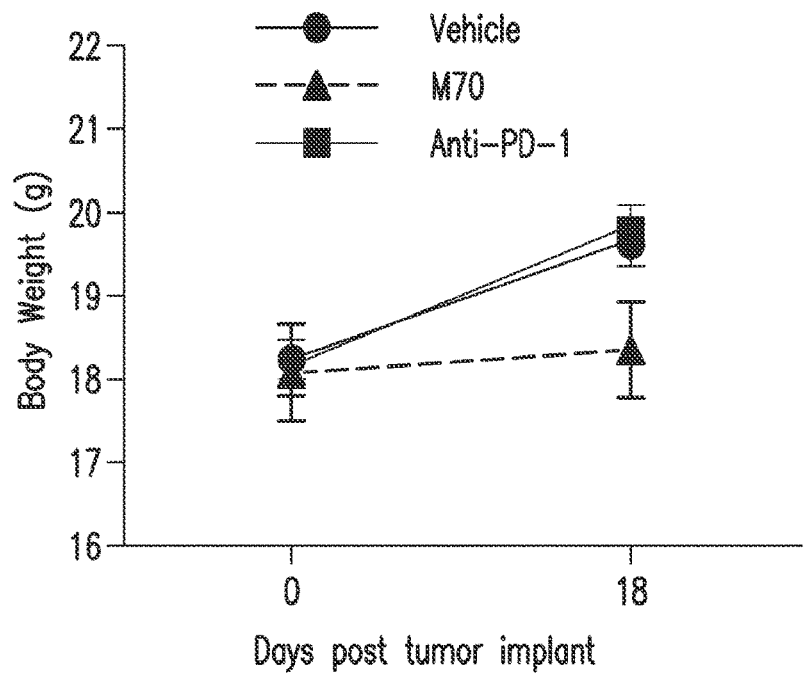

FIGS. 14A-14B depicts M70 reduces body weight in a CT26 colon cancer syngenic mouse model. (A) M70 reduces body weight following administration of 10 mg/kg doses. (B) M70 reduces body weight following administration of 3 mg/kg doses. The p-values were determined by two-way ANOVA vs. vehicle-treated mice. *p<0.001; p<0.01.

DETAILED DESCRIPTION

Before the present disclosure is further described, it is to be understood that the disclosure is not limited to the particular embodiments set forth herein, and it is also to be understood that the terminology used herein is for the purpose of describing particular embodiments only, and is not intended to be limiting.

Overview

The present disclosure contemplates the identification of agents, and compositions thereof, using the models and methods described herein. The models and associated methods provide an accurate, efficient methodology for the identification of agents that do not induce cancerous conditions (e.g., hepatocellular carcinoma). In certain embodiments, the models and methods provided herein are useful in identifying agents that antagonize the oncogenic activity of FGF19. In certain embodiments, such agents have therapeutic utility in the treatment and/or prevention of various diseases, disorders and conditions, and/or the symptoms thereof, pertaining to, for example, glucose metabolism disorders and/or body weight disorders. By way of example, but not limitation, the agents, and compositions thereof, can be used for the treatment and/or prevention of type 2 diabetes, insulin resistance and diseases, disorders and conditions characterized by insulin resistance, decreased insulin production, hyperglycemia, metabolic syndrome, or obesity. Such agents are also useful in the prevention or treatment a FGF19-dependent disease, disorder or condition, or a symptom thereof.

The models and associated methods described herein are useful in identifying agents (e.g., polypeptides and antibodies) that neither induce nor exacerbate the cancer-related effects of FGF19 (e.g., HCC). As described in detail hereafter, particular embodiments contemplate the use of the models and methods to determine whether a FGF19 variant polypeptide having favorable metabolic characteristics will also possess a desirable "cancer-related" profile. Also provided are methods of antagonizing the oncogenic activity of FGF19 in a subject and, in certain embodiments, methods of preventing or treating a FGF19-dependent disease, disorder or condition, or a symptom thereof. In certain embodiments, the FGF19 dependent disease, disorder or condition is a cancer or tumor, such as a liver, colon, prostate or lung cancer or tumor.

Definitions

The terms "patient" or "subject" are used interchangeably to refer to a human or a non-human animal (e.g., a mammal).

The terms "treat", "treating", treatment" and the like refer to a course of action (such as administering a polypeptide or a pharmaceutical composition comprising a polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms association therewith) an active disease (e.g., so as to decrease the level of insulin and/or glucose in the bloodstream, to increase glucose tolerance so as to minimize fluctuation of glucose levels, and/or so as to protect against diseases caused by disruption of glucose homeostasis).

The term "in need of treatment" as used herein refers to a judgment made by a physician or other medical professional that a subject requires or will benefit from treatment.

The terms "prevent", "preventing", "prevention" and the like refer to a course of action (such as administering a polypeptide or a pharmaceutical composition comprising a polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other medical professional that a subject requires or will benefit from preventative care.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. In the case of a hyperglycemic condition, a lowering or reduction of blood glucose or an improvement in glucose tolerance test can be used to determine whether the amount of an agent is effective to treat the hyperglycemic condition. For example, a therapeutically effective amount is an amount sufficient to reduce or decrease any level (e.g., a baseline level) of fasting plasma glucose (FPG), wherein, for example, the amount is sufficient to reduce a FPG level greater than 200 mg/dl to less than 200 mg/dl, wherein the amount is sufficient to reduce a FPG level between 175 mg/dl and 200 mg/dl to less than the starting level, wherein the amount is sufficient to reduce a FPG level between 150 mg/dl and 175 mg/dl to less than the starting level, wherein the amount is sufficient to reduce a FPG level between 125 mg/dl and 150 mg/dl to less than the starting level, and so on (e.g., reducing FPG levels to less than 125 mg/dl, to less than 120 mg/dl, to less than 115 mg/dl, to less than 110 mg/dl, etc.). Moreover, in the case of HbAlc levels, the effective amount is an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbAlc levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is contemplated by the present disclosure. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of glucose or insulin) or subjective parameter (e.g., a subject's feeling of well-being).

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

Broadly speaking, the terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, can progress to diabetes. The presence of these conditions can be determined using, for example, either the fasting plasma glucose (FPG) test or the oral glucose tolerance test (OGTT). Both usually require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dl, a subject with "pre-diabetes" would generally have a FPG concentration between about 100 and about 125 mg/dl, and a subject with "diabetes" would generally have a FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dl, a murine subject with "pre-diabetes" would generally have a FPG concentration between about 175 and about 250 mg/dl and a murine subject with "diabetes" would generally have a FPG concentration above about 250 mg/dl.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" refers to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of type 2 diabetes and/or other disorders (e.g., atherosclerosis).

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin can be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, other metabolic disorders (such as metabolic syndrome, which is also referred to as syndrome X), and obesity, among others. The polypeptides of the present disclosure, and compositions thereof, can be used, for example, to achieve and/or maintain glucose homeostasis, e.g., to reduce glucose level in the bloodstream and/or to reduce insulin level to a range found in a healthy subject.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia, such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 µU/mL.

As used herein, the phrase "body weight disorder" refers to conditions associated with excessive body weight and/or enhanced appetite. Various parameters are used to determine whether a subject is overweight compared to a reference healthy individual, including the subject's age, height, sex and health status. For example, a subject can be considered overweight or obese by assessment of the subject's Body Mass Index (BMI), which is calculated by dividing a subject's weight in kilograms by the subject's height in meters squared. An adult having a BMI in the range of ~18.5 to ~24.9 $kg/m^2$ is considered to have a normal weight; an adult having a BMI between ~25 and ~29.9 $kg/m^2$ can be considered overweight (pre-obese); and an adult having a BMI of ~30 $kg/m^2$ or higher can be considered obese. Enhanced appetite frequently contributes to excessive body weight. There are several conditions associated with enhanced appetite, including, for example, night eating syndrome, which is characterized by morning anorexia and evening polyphagia often associated with insomnia, but which can be related to injury to the hypothalamus.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like. It will be appreciated that throughout this disclosure reference is made to amino acids according to the single letter or three letter codes.

As used herein, the term "variant" encompasses naturally-occurring variants (e.g., homologs and allelic variants) and non-naturally-occurring variants (e.g., muteins). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced, e.g., the change is generated in the laboratory or other facility by human intervention ("hand of man").

The term "native", in reference to FGF19, refers to biologically active, naturally-occurring FGF19, including biologically active, naturally-occurring FGF19 variants. The term includes the 194 amino acid human FGF19 mature sequence.

The terms "label", "labeling" and the like, when use in the context of a polypeptide or nucleic acid (or antibody, as appropriate) of the present disclosure are meant to refer broadly to any means useful in, for example, polypeptide purification, identification, isolation and synthesis. Labels are generally covalently bound to the polypeptide of interest and can be introduced in any manner known in the art, including attachment to a mature polypeptide (generally at the N- or C-terminus), incorporation during solid-phase peptide synthesis, or through recombinant means. Examples include, but are not limited to, fluorescence, biotinylation, and radioactive isotopes. Polypeptide and nucleic acid molecules can be labeled by both in vitro and in vivo methods. Labeling reagents and kits can be obtained from a number of commercial sources (e.g., Thermo Fischer Scientific, Rockford, Ill.; and Molecular Probes/Life Technologies; Grand Island, N.Y.).

As used herein, the terms "FLAG-tag", "FLAG octapeptide", and the like refer to an eight amino acid (DYKDDDDK) (SEQ ID NO:2) peptide tag (label) that can be added to a polypeptide using recombinant DNA techniques. Antibodies to the FLAG component of the polypeptide can be used for, for example, affinity chromatography and cellular localization studies by immunofluorescence or detection by SDS PAGE protein electrophoresis. A FLAG-tag can be used in conjunction with other affinity tags (e.g., a polyhistidine tag (His-tag) or myc-tag), and it can be fused to the C-terminus or the N-terminus of a polypeptide.

The term "muteins" as used herein refers broadly to mutated recombinant proteins, i.e., a polypeptide comprising an artificially introduced change in amino acid sequence, e.g., a change in amino acid sequence generated in the laboratory or other facility by human intervention ("hand of man"). These proteins usually carry single or multiple amino acid substitutions and are frequently derived from cloned genes that have been subjected to site-directed or random mutagenesis, or from completely synthetic genes.

As used herein in reference to native human FGF19 or a FGF19 mutein, the terms "modified", "modification" and the like refer to one or more changes that enhance a desired property of human FGF19, a naturally-occurring FGF19 variant, or a FGF19 mutein, wherein the change(s) does not alter the primary amino acid sequence of the FGF19. Such desired properties include, for example, enhancing solubility, prolonging the circulation half-life, increasing the stability, reducing the clearance, altering the immunogenicity or allergenicity, improving aspects of manufacturability (e.g., cost and efficiency), and enabling the raising of particular antibodies (e.g., by introduction of unique epitopes) for use in detection assays. Changes to human FGF19, a naturally-occurring FGF19 variant, or a FGF19 mutein that can be carried out include, but are not limited to, pegylation (covalent attachment of one or more molecules of polyethylene glycol (PEG), or derivatives thereof); glycosylation (e.g., N-glycosylation), polysialylation and hesylation; albumin fusion; albumin binding through, for example, a conjugated fatty acid chain (acylation); Fc-fusion; and fusion with a PEG mimetic. Some particular embodiments entail modifications involving polyethylene glycol, other particular embodiments entail modifications involving albumin, and still other particular modifications entail modifications involving glycosylation.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

The term "probe" refers to a fragment of DNA or RNA corresponding to a gene or sequence of interest, wherein the fragment has been labeled radioactively (e.g., by incorporating $^{32}P$ or $^{35}S$) or with some other detectable molecule, such as biotin, digoxygen or fluorescein. As stretches of DNA or RNA with complementary sequences will hybridize, a probe can be used, for example, to label viral plaques, bacterial colonies or bands on a gel that contain the gene of interest. A probe can be cloned DNA or it can be a synthetic DNA strand; the latter can be used to obtain a cDNA or genomic clone from an isolated protein by, for example, microsequencing a portion of the protein, deducing the nucleic acid sequence encoding the protein, synthesizing an oligonucleotide carrying that sequence, radiolabeling the sequence and using it as a probe to screen a cDNA library or a genomic library.

The term "heterologous" refers to two components that are defined by structures derived from different sources. For example, in the context of a polypeptide, a "heterologous" polypeptide can include operably linked amino acid sequences that are derived from different polypeptides. Similarly, in the context of a polynucleotide encoding a chimeric polypeptide, a "heterologous" polynucleotide can include operably linked nucleic acid sequences that can be derived from different genes. Exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which can be of different genetic origin than the promoter, the coding sequence or both). In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) can be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" a FGF19 polypeptide), is meant to indicate that the polypeptide or nucleic acid has a sequence that is based on that of a reference polypeptide or nucleic acid (e.g., a naturally occurring FGF19 polypeptide or a FGF19-encoding nucleic acid), and is not meant to be limiting as to the source or method in which the protein or nucleic acid is made. By way of example, the term "derived from" includes homologues or variants of reference amino acid or DNA sequences.

In the context of a polypeptide, the term "isolated" refers to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates the polypeptide has been separated from an environment in which it was made by either synthetic or recombinant means.

"Enriched" means that a sample is non-naturally manipulated (e.g., by a scientist or a clinician) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "assaying" and "measuring" and grammatical variations thereof are used interchangeably herein and refer to either qualitative or quantitative determinations, or both qualitative and quantitative determinations. When the terms are used in reference to detection, any means of assessing the relative amount is contemplated, including the various methods set forth herein and known in the art. For example, gene expression can be assayed or measured by a Northern blot, Western blot, immunoprecipitation assay, or by measuring activity, function or amount of the expressed protein.

The terms "antibodies" (Abs) and "immunoglobulins" (Igs) refer to glycoproteins having the same structural characteristics. While antibodies exhibit binding specificity to a specific antigen, immunoglobulins include both antibodies and other antibody-like molecules which lack antigen specificity.

The term "monoclonal antibody" refers to an antibody obtained from a population of substantially homogeneous antibodies, that is, the individual antibodies comprising the population are identical except for possible naturally occurring mutations that can be present in minor amounts. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen.

In the context of an antibody, the term "isolated" refers to an antibody that has been separated and/or recovered from contaminant components of its natural environment; such contaminant components include materials which might interfere with diagnostic or therapeutic uses for the antibody, and can include enzymes, hormones, and other proteinaceous or nonproteinaceous solutes.

As used herein, the term "FGF19-dependent" and similar terms, as used in the context of a disease, disorder or condition, refers to a disease, disorder or other condition that is caused all, or in part, by the expression of FGF19. In certain embodiments, the expression of FGF19 is amplified as compared to a control. In some embodiments, the expression of FGF19 is amplified 5%, 10%, 15%, 20%, 25%, 30%, 35%, 40%, 45%, 50%, 55%, 60%, 65%, 70%, 75%, 80%, 85%, 90%, 95% or more, or any numerical range thereof. In some embodiments, the amplified expression of FGF19 directly results in the disease, disorder or condition, or a symptom thereof. In other embodiments, the amplified expression of FGF19 indirectly results in the disease disorder or condition, or a symptom thereof.

Fibroblast Growth Factor 19 (FGF19)

Fibroblast growth factors (FGFs) are a family of growth factors that play key roles in cellular proliferation and differentiation. Twenty-two members of the FGF family have been identified in humans, all of which are structurally-related signaling molecules. The FGF19 subfamily of FGFs consists of human FGF21, FGF23 and FGF19 and mouse FGF15.

The physiological effects of FGF family members are the result of heparin-dependent binding to one or more members of the FGF receptor tyrosine kinase (FGFR) family, which includes four members (FGFR1, FGFR2, FGFR3 and FGFR4), each having a tyrosine kinase domain. In addition, each of FGFR1, FGFR2 and FGFR3 also has two splice variants designated as "b" and "c" variants (i.e., FGFR1b, FGFR2b, FGFR3b, FGFR1c, FGFR2c and FGFR3c).

FGF19 targets and has effects on both adipocytes and hepatocytes. Mice treated with recombinant human FGF19, despite being on a high-fat diet, show increased metabolic rates, increased lipid oxidation, a lower respiratory quotient, and weight loss. The metabolic effects of FGF19 occur via its binding to the FGFR1c, FGFR2c and FGFR3c receptors, of which the binding to FGFR1c and FGFR2c are the most significant. FGF19 binding to these receptors requires the co-receptor Klotho-β (KLB).

FGF19 has also been shown to regulate bile production by the liver. Thus, FGF19-like agents can play an important role in bile acid homeostasis. Results suggest that FGF19-regulated liver bile acid metabolism could be independent of its glucose-lowering effect.

As alluded to elsewhere herein, use of gastric bypass surgery for the treatment of diabetes has been shown to completely and persistently cure type II diabetes in most patients. This "bariatric effect" is evident only days after surgery and long before significant weight loss is achieved. FGF19 levels increase after bariatric surgery, and it can be responsible for the bariatric effect.

FGF19 is expressed as a 216 amino acid polypeptide comprising a 22 residue signal peptide (GenBank: AAQ88669.1). Mature human FGF19 (wild-type) is a 194 amino acid polypeptide comprising the following amino acid sequence:

(SEQ ID NO: 3)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK.

FGF19 and Hepatocellular Carcinoma.

As described herein, FGF19 is associated with the induction of cancer, particularly HCC, the most common type of liver cancer. In accordance with certain aspects, there are provided methods and models of identifying a polypeptide, or a subsequence, variant or modified form thereof, as set forth herein, having a desired metabolic activity (e.g., glucose lowering activity) but lacking or without substantial HCC activity. Various metabolic disorders and associated methods (e.g., methods of measuring glucose levels), along with methods of detecting cancers, are described elsewhere herein and are known in the art.

Various methodologies can be used in the screening and diagnosis of HCC and are well known to the skilled artisan. Indicators for HCC include, but are not limited to, detection of a tumor maker, such as elevated alpha-fetoprotein (AFP) or des-gamma carboxyprothrombin (DCP) levels. A number of different scanning and imaging techniques are also available, including ultrasound, CT scans and MRI. In relation to certain embodiments of the methods and models provided herein, evaluation of whether a polypeptide (e.g., a candidate polypeptide) exhibits evidence of inducing HCC is determined in vivo by, for example, quantifying HCC nodule formation in an animal model (e.g., a db/db mouse model) administered a polypeptide, compared to HCC nodule formation induced by wild-type FGF19. Macroscopically, HCC can be nodular, whereas the tumor nodules (which are frequently round-to-oval, grey or green, well circumscribed but not encapsulated) appear as either one large mass or multiple smaller masses. Alternatively, HCC can be present as an infiltrative tumor which is diffuse and poorly circumscribed and frequently infiltrates the portal veins. Risk factors for HCC include type 2 diabetes (often exacerbated by obesity). The risk of HCC in type 2 diabetics is greater (from ~2.5 to ~7 times the non-diabetic risk) depending on the duration of diabetes and treatment protocol.

Pathological assessment of hepatic tissue samples is generally performed after the results of one or more of the aforementioned methodologies indicate the likely presence of HCC. Thus, certain embodiments of the methods provided herein further include assessing a hepatic tissue sample from an in vivo animal model useful in HCC studies in order to determine whether a polypeptide sequence exhibits evidence of inducing HCC. In certain embodiments, the in vivo animal model is a db/db mouse model. By microscopic assessment, a pathologist can determine whether one of the four general architectural and cytological types (patterns) of HCC are present (i.e., fibrolamellar, pseudoglandular (adenoid), pleomorphic (giant cell) and clear cell).

Methods and Models for Identifying FGF19 Variant Polypeptides Having Desired Characteristics.

FGF19 variant polypeptides and other agents that mimic, at least in some respects, the activity of FGF19 are described in both the scientific and patent literature. See, e.g., Wu et al., PLos One, 6:e17868 (Mar. 11, 2001); U.S. Pat. No. 8,324,160; and US Publ. Nos. 2011/0195895; 2011/0207912 and 2011/0104152. Though not intended to be limiting in any way, candidate FGF19 variant sequences include polypeptides having a WGDPI (SEQ ID NO:4) sequence motif corresponding to the WGDPI sequence of amino acids 16-20 of FGF19 (SEQ ID NO:3). A particular polypeptide contemplated herein has the following amino acid sequence:

(M70, SEQ ID NO: 1)
MRDSSPLVHYGWGDPIRLRHLYTSGPHGLSSCFLRIRADGVVDCARGQSA

HSLLEIKAVALRTVAIKGVHSVRYLCMGADGKMQGLLQYSEEDCAFEEEI

RPDGYNVYRSEKHRLPVSLSSAKQRQLYKNRGFLPLSHFLPMLPMVPEEP

EDLRGHLESDMFSSPLETDSMDPFGLVTGLEAVRSPSFEK.

In other embodiments, a FGF19 variant comprises or consists of an amino acid sequence set forth as:

(M5, SEQ ID NO: 5)
RHPIPDSSPLLQFGGQVRLRHLYTSGPHGLSSCFLRIRADGVVDCARGQ

SAHSLLEIKAVALRTVAIKGVHSVRYLCMGADGKMQGLLQYSEEDCAFE

EEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK;

(M6, SEQ ID NO: 6)
RDSSPLLQFGGQVRLRHLYTSGPHGLSSCFLRIRADGVVDCARGQSAHS

LLEIKAVALRTVAIKGVHSVRYLCMGADGKMQGLLQYSEEDCAFEEEIR

PDGYNVYRSEKHRLPVSLSSAKQRQLYKNRGFLPLSHFLPMLPMVPEEP

EDLRGHLESDMFSSPLETDSMDPFGLVTGLEAVRSPSFEK;

(M7, SEQ ID NO: 7)
RPLAFSDSSPLLQFGGQVRLRHLYTSGPHGLSSCFLRIRADGVVDCARG

QSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPM

VPEEPEDLRGHLESDMFSSPLETDSMDPFGLVTGLEAVRSPSFEK;

(M14, SEQ ID NO: 8)
RHPIPDSSPHVHYGGQVRLRHLYTSGPHGLSSCFLRIRADGVVDCARGQ

SAHSLLEIKAVALRTVAIKGVHSVRYLCMGADGKMQGLLQYSEEDCAFE

EEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK;

(M15, SEQ ID NO: 9)
RPLAFSDAGPHVHYGGQVRLRHLYTSGPHGLSSCFLRIRADGVVDCARG

QSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPM

VPEEPEDLRGHLESDMFSSPLETDSMDPFGLVTGLEAVRSPSFEK;

-continued (M32, SEQ ID NO:10)
RHPIPDSSPLLQFGDQVRLRHLYTSGPHGLSSCFLRIRADGVVDCARGQ
SAHSLLEIKAVALRTVAIKGVHSVRYLCMGADGKMQGLLQYSEEDCAFE
EEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK;

(M36, SEQ ID NO: 11)
RHPIPDSSPLLQFGGNVRLRHLYTSGPHGLSSCFLRIRADGVVDCARGQ
SAHSLLEIKAVALRTVAIKGVHSVRYLCMGADGKMQGLLQYSEEDCAFE
EEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK;

(M43, SEQ ID NO: 12)
RPLAFSDAGPHVHYGGDIRLRHLYTSGPHGLSSCFLRIRADGVVDCARG
QSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPM
VPEEPEDLRGHLESDMFSSPLETDSMDPFGLVTGLEAVRSPSFEK;

(M50, SEQ ID NO: 13)
RHPIPDSSPLLQFGDQVRLRHLYTSGPHGLSSCFLRIRADGVVDCARGQ
SAHSLLEIKAVALRTVAIKGVHSVRYLCMGADGKMQGLLQYSEEDCAFE
EEILEDGYNVYRSEKHRLPVSLSSAKQRQLYKNRGFLPLSHFLPMLPMV
PEEPEDLRGHLESDMFSSPLETDSMDPFGLVTGLEAVRSPSFEK;

(M52, SEQ ID NO: 14)
RDSSPLLQWGDPIRLRHLYTSGPHGLSSCFLRIRADGVVDCARGQSAHS
LLEIKAVALRTVAIKGVHSVRYLCMGADGKMQGLLQYSEEDCAFEEEIR
PDGYNVYRSEKHRLPVSLSSAKQRQLYKNRGFLPLSHFLPMLPMVPEEP
EDLRGHLESDMFSSPLETDSMDPFGLVTGLEAVRSPSFEK;

(M53, SEQ ID NO: 15)
MDSSPLLQWGDPIRLRHLYTSGPHGLSSCFLRIRADGVVDCARGQSAHS
LLEIKAVALRTVAIKGVHSVRYLCMGADGKMQGLLQYSEEDCAFEEEIR
PDGYNVYRSEKHRLPVSLSSAKQRQLYKNRGFLPLSHFLPMLPMVPEEP
EDLRGHLESDMFSSPLETDSMDPFGLVTGLEAVRSPSFEK;

(M67, SEQ ID NO: 16)
RPLAFSDAGPHVWGDPIRLRHLYTSGPHGLSSCFLRIRADGVVDCARGQ
SAHSLLEIKAVALRTVAIKGVHSVRYLCMGADGKMQGLLQYSEEDCAFE
EEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK;

(M68, SEQ ID NO: 17)
RPLAFSDAGPHVHYWGDPIRLRHLYTSGPHGLSSCFLRIRADGVVDCAR
GQSAHSLLEIKAVALRTVAIKGVHSVRYLCMGADGKMQGLLQYSEEDCA
FEEEIRPDGYNVYRSEKHRLPVSLSSAKQRQLYKNRGFLPLSHFLPMLP
MVPEEPEDLRGHLESDMFSSPLETDSMDPFGLVTGLEAVRSPSFEK;

(M69, SEQ ID NO: 18)
RDSSPLVHYGWGDPIRLRHLYTSGPHGLSSCFLRIRADGVVDCARGQSA
HSLLEIKAVALRTVAIKGVHSVRYLCMGADGKMQGLLQYSEEDCAFEEE
IRPDGYNVYRSEKHRLPVSLSSAKQRQLYKNRGFLPLSHFLPMLPMVPE
EPEDLRGHLESDMFSSPLETDSMDPFGLVTGLEAVRSPSFEK;

(M70, SEQ ID NO: 1 or 19)
MRDSSPLVHYGWGDPIRLRHLYTSGPHGLSSCFLRIRADGVVDCARGQS
AHSLLEIKAVALRTVAIKGVHSVRYLCMGADGKMQGLLQYSEEDCAFEE
EIRPDGYNVYRSEKHRLPVSLSSAKQRQLYKNRGFLPLSHFLPMLPMVP
EEPEDLRGHLESDMFSSPLETDSMDPFGLVTGLEAVRSPSFEK;

(M75, SEQ ID NO: 20)
RVHYGWGDPIRLRHLYTSGPHGLSSCFLRIRADGVVDCARGQSAHSLLE
IKAVALRTVAIKGVHSVRYLCMGADGKMQGLLQYSEEDCAFEEEIRPDG
YNVYRSEKHRLPVSLSSAKQRQLYKNRGFLPLSHFLPMLPMVPEEPEDL
RGHLESDMFSSPLETDSMDPFGLVTGLEAVRSPSFEK;

(M76, SEQ ID NO: 21)
RGDPIRLRHLYTSGPHGLSSCFLRIRADGVVDCARGQSAHSLLEIKAVA
LRTVAIKGVHSVRYLCMGADGKMQGLLQYSEEDCAFEEEIRPDGYNVYR
SEKHRLPVSLSSAKQRQLYKNRGFLPLSHFLPMLPMVPEEPEDLRGHLE
SDMFSSPLETDSMDPFGLVTGLEAVRSPSFEK;

(M77, SEQ ID NO: 22)
RRLRHLYTSGPHGLSSCFLRIRADGVVDCARGQSAHSLLEIKAVALRTV
AIKGVHSVRYLCMGADGKMQGLLQYSEEDCAFEEEIRPDGYNVYRSEKH
RLPVSLSSAKQRQLYKNRGFLPLSHFLPMLPMVPEEPEDLRGHLESDMF
SSPLETDSMDPFGLVTGLEAVRSPSFEK;

(M83, SEQ ID NO: 23)
RPLAFSDAAPHVHYGWGDPIRLRHLYTSGPHGLSSCFLRIRADGVVDCA
RGQSAHSLLEIKAVALRTVAIKGVHSVRYLCMGADGKMQGLLQYSEEDC
AFEEEIRPDGYNVYRSEKHRLPVSLSSAKQRQLYKNRGFLPLSHFLPML
PMVPEEPEDLRGHLESDMFSSPLETDSMDPFGLVTGLEAVRSPSFEK;

(M84, SEQ ID NO: 24)
RPLAFSDAGAHVHYGWGDPIRLRHLYTSGPHGLSSCFLRIRADGVVDCA
RGQSAHSLLEIKAVALRTVAIKGVHSVRYLCMGADGKMQGLLQYSEEDC
AFEEEIRPDGYNVYRSEKHRLPVSLSSAKQRQLYKNRGFLPLSHFLPML
PMVPEEPEDLRGHLESDMFSSPLETDSMDPFGLVTGLEAVRSPSFEK;

(M140, SEQ ID NO: 25)
RPLAFSDAGPHVHYGWGDPIRLRHLYTSGPHGLSSCFLRIRADGVVDCA
RGQSAHSLLEIKAVALRTVAIKGVHSVRYLCMGADGKMQGLLQYSEEDC
AFEEEIREDGYNVYRSEKHRLPVSLSSAKQRQLYKNRGFLPLSHFLPML
PMVPEEPEDLRGHLESDMFSSPLETDSMDPFGLVTGLEAVRSPSFEK;

(M144 (M5-R), SEQ ID NO: 26)
HPIPDSSPLLQFGGQVRLRHLYTSGPHGLSSCFLRIRADGVVDCARGQS
AHSLLEIKAVALRTVAIKGVHSVRYLCMGADGKMQGLLQYSEEDCAFEE
EIRPDGYNVYRSEKHRLPVSLSSAKQRQLYKNRGFLPLSHFLPMLPMVP
EEPEDLRGHLESDMFSSPLETDSMDPFGLVTGLEAVRSPSFEK;

(M145 (M6-R), SEQ ID NO: 27)
DSSPLLQFGGQVRLRHLYTSGPHGLSSCFLRIRADGVVDCARGQSAHSL
LEIKAVALRTVAIKGVHSVRYLCMGADGKMQGLLQYSEEDCAFEEEIRP
DGYNVYRSEKHRLPVSLSSAKQRQLYKNRGFLPLSHFLPMLPMVPEEPE
DLRGHLESDMFSSPLETDSMDPFGLVTGLEAVRSPSFEK;

-continued (M146 (M50-R), SEQ ID NO: 28)
HPIPDSSPLLQFGDQVRLRHLYTSGPHGLSSCFLRIRADGVVDCARGQS

AHSLLEIKAVALRTVAIKGVHSVRYLCMGADGKMQGLLQYSEEDCAFEE

EILEDGYNVYRSEKHRLPVSLSSAKQRQLYKNRGFLPLSHFLPMLPMVP

EEPEDLRGHLESDMFSSPLETDSMDPFGLVTGLEAVRSPSFEK;

(M160, SEQ ID NO: 29)
RPLAFSDAGPHVHYGWGDPIRQRHLYTSGPHGLSSCFLRIRADGVVDCA

RGQSAHSLLEIKAVALRTVAIKGVHSVRYLCMGADGKMQGLLQYSEEDC

AFEEEILEDGYNVYRSEKHRLPVSLSSAKQRQLYKNRGFLPLSHFLPML

PMVPEEPEDLRGHLESDMFSSPLETDSMDPFGLVTGLEAVRSPSFEK;

or a subsequence or fragment thereof of any of the foregoing peptide sequences. In certain embodiments of any of the foregoing peptide sequences, the N-terminal R residue is deleted.

As previously described, one aspect of the present disclosure contemplates a method for determining whether a test subject having a metabolic disorder is a candidate for treatment with a FGF19 variant, the method comprising: (a) providing a test subject having an indicia of a cancerous condition, the subject having a metabolic disorder, (b) co-administering FGF19 or a FGF19 surrogate, and a FGF19 variant to the test subject, wherein the amount of the FGF19 or the FGF19 surrogate administered to the test subject is sufficient to induce a cancerous condition in a reference population, and (c) determining whether an indicia of a cancerous condition is enhanced in the test subject; wherein the absence of enhancement of an indicia of a cancerous condition indicates that the test subject is a candidate for treatment with a FGF19 variant.

Another aspect of the present disclosure contemplates a method for determining whether a test subject having a metabolic disorder is a candidate for treatment with a FGF19 variant, the method comprising: (a) providing a test subject having an indicia of a cancerous condition, the test subject having a metabolic disorder, (b) co-administering FGF19 or a FGF19 surrogate, and a FGF19 variant to the test subject, wherein the amount of the FGF19 or the FGF19 surrogate is administered to the test subject is sufficient to induce a cancerous condition in a reference population, and (c) determining whether an indicia of a cancerous condition is reduced in the test subject; wherein the reduction of an indicia of a cancerous condition indicates that the test subject is a candidate for treatment with a FGF19 variant.

The present disclosure also contemplates a method for determining whether a FGF19 variant is a candidate for treating a test subject having a metabolic disorder, the method comprising: (a) co-administering FGF19 or a FGF19 surrogate, and the FGF19 variant to the test subject having a metabolic disorder, wherein the amount of the FGF19 or the FGF19 surrogate administered to the test subject is sufficient to induce a cancerous condition in a reference population, and (b) determining whether an indicia of a cancerous condition is observed in the test subject; wherein the absence of an indicia of a cancerous condition indicates that the FGF19 variant is a candidate for treatment of the test subject.

A further embodiment contemplated herein is drawn to a method for determining whether a FGF19 variant is a candidate for treating a test subject having a metabolic disorder, the method comprising: (a) providing a test subject having a metabolic disorder, the test subject having an indicia of a cancerous condition, (b) co-administering FGF19 or a FGF19 surrogate, and a FGF19 variant to the test subject, wherein the amount of the FGF19 or the FGF19 surrogate is administered to the test subject is sufficient to exacerbate a cancerous condition in a reference population, and (c) determining whether an indicia of a cancerous condition is enhanced in the test subject; wherein the absence of exacerbation of an indicia of a cancerous condition indicates that the FGF19 variant is a candidate for treatment of the test subject. In particular embodiments, one or more indicia of a cancerous condition are reduced in the test subject.

In certain embodiments of the methods provided herein, the FGF19 variant is selected from the group consisting of M5, M6, M7, M14, M15, M32, M36, M43, M52, M53, M67, M68, M69, M70, M75, M76, M77, M83, M84, M140, M144, M145, M146 and M160. In one embodiment, the FGF19 variant is M5. In another embodiment, the FGF19 variant is M6. In some embodiments, the FGF19 variant is M7. In one embodiment, the FGF19 variant is M14. In another embodiment, the FGF19 variant is M15. In other embodiments, the FGF19 variant is M32. In one embodiment, the FGF19 variant is M36. In another embodiment, the FGF19 variant is M43. In other embodiments, the FGF19 variant is M52. In yet other embodiment, the FGF19 variant is M53. In some embodiments, the FGF19 variant is M67. In one embodiment, the FGF19 variant is M68. In another embodiment, the FGF19 variant is M69. In some embodiments, the FGF19 variant is M70. In one embodiment, the FGF19 variant is M75. In another embodiment, the FGF19 variant is M76. In other embodiments, the FGF19 variant is M77. In yet other embodiments, the FGF19 variant is M83. In one embodiment, the FGF19 variant is M84. In another embodiment, the FGF19 variant is M140. In other embodiments, the FGF19 variant is M144. In yet other embodiments, the FGF19 variant is M145. In one embodiment, the FGF19 variant is M146. In some embodiments, the FGF19 variant is M160. In other embodiments, any combination of two or more of the foregoing FGF19 variants is also contemplated.

In some embodiments of the methods provided herein, the FGF19 variant comprises an amino acid sequence set forth in any one of SEQ ID NOS:5-29; or a subsequence or fragment thereof. In certain embodiments, the N-terminal R residue is deleted. In some embodiments, the FGF19 variant comprises SEQ ID NO:5. In other embodiments, the FGF19 variant comprises SEQ ID NO:6. In one embodiment, the FGF19 variant comprises SEQ ID NO:7. In other embodiments, the FGF19 variant comprises SEQ ID NO:8. In another embodiment, the FGF19 variant comprises SEQ ID NO:9. In some embodiments, the FGF19 variant comprises SEQ ID NO:10. In other embodiments, the FGF19 variant comprises SEQ ID NO:11. In another embodiment, the FGF19 variant comprises SEQ ID NO:12. In some embodiments, the FGF19 variant comprises SEQ ID NO:13. In other embodiments, the FGF19 variant comprises SEQ ID NO:14. In one embodiment, the FGF19 variant comprises SEQ ID NO:15. In another embodiment, the FGF19 variant comprises SEQ ID NO:16. In some embodiments, the FGF19 variant comprises SEQ ID NO:17. In other embodiments, the FGF19 variant comprises SEQ ID NO:18. In yet other embodiments, the FGF19 variant comprises SEQ ID NO:19. In some embodiments, the FGF19 variant comprises SEQ ID NO:20. In one embodiment, the FGF19 variant comprises SEQ ID NO:21. In some embodiments, the FGF19 variant comprises SEQ ID NO:22. In other embodiments, the FGF19 variant comprises SEQ ID NO:23. In another embodiment, the FGF19 variant comprises SEQ ID NO:24. In some embodiments, the FGF19 variant comprises SEQ ID NO:25. In other embodiments, the FGF19 variant comprises SEQ ID NO:26. In yet other embodiments, the FGF19 variant comprises SEQ ID NO:27. In some embodiments, the FGF19 variant comprises SEQ ID NO:28. In other embodiments, the FGF19 variant comprises SEQ ID NO:29. In certain embodiments, the FGF19 variant comprises any one of the foregoing sequences, wherein the N-terminal R residue is deleted. In some embodiments, the FGF19 variant comprises a subsequence of any of the foregoing sequences. In other embodiments, any combination of two or more of the foregoing FGF19 variants is also contemplated.

In some embodiments of the methods provided herein, the FGF19 variant consists of an amino acid sequence set forth in any one of SEQ ID NOS: 5-29; or a subsequence or fragment thereof. In certain embodiments, the N-terminal R residue is deleted. In some embodiments, the FGF19 variant consists of SEQ ID NO:5. In other embodiments, the FGF19 variant consists of SEQ ID NO:6. In one embodiment, the FGF19 variant consists of SEQ ID NO:7. In other embodiments, the FGF19 variant consists of SEQ ID NO:8. In another embodiment, the FGF19 variant consists of SEQ ID NO:9. In some embodiments, the FGF19 variant consists of SEQ ID NO:10. In other embodiments, the FGF19 variant consists of SEQ ID NO:11. In another embodiment, the FGF19 variant consists of SEQ ID NO:12. In some embodiments, the FGF19 variant consists of SEQ ID NO:13. In other embodiments, the FGF19 variant consists of SEQ ID NO:14. In one embodiment, the FGF19 variant consists of SEQ ID NO:15. In another embodiment, the FGF19 variant consists of SEQ ID NO:16. In some embodiments, the FGF19 variant consists of SEQ ID NO:17. In other embodiments, the FGF19 variant consists of SEQ ID NO:18. In yet other embodiments, the FGF19 variant consists of SEQ ID NO:19. In some embodiments, the FGF19 variant consists of SEQ ID NO:20. In one embodiment, the FGF19 variant consists of SEQ ID NO:21. In some embodiments, the FGF19 variant consists of SEQ ID NO:22. In other embodiments, the FGF19 variant consists of SEQ ID NO:23. In another embodiment, the FGF19 variant consists of SEQ ID NO:24. In some embodiments, the FGF19 variant consists of SEQ ID NO:25. In other embodiments, the FGF19 variant consists of SEQ ID NO:26. In yet other embodiments, the FGF19 variant consists of SEQ ID NO:27. In some embodiments, the FGF19 variant consists of SEQ ID NO:28. In other embodiments, the FGF19 variant consists of SEQ ID NO:29. In certain embodiments, the FGF19 variant consists of any one of the foregoing sequences, wherein the N-terminal R residue is deleted. In some embodiments, the FGF19 variant consists of a subsequence of any of the foregoing sequences. In other embodiments, any combination of two or more of the foregoing FGF19 variants is also contemplated.

As alluded to above, the present disclosure also contemplates various models. Any model can be used that provides reliable, reproducible results. The skilled artisan is familiar with models that can be used in conjunction with the subject matter of the present disclosure. In some embodiments, rodent models are used, particularly mouse models. In addition to the ob/ob mouse models used in the examples of the Experimental section, db/db, db/ob and DIO models can find use in practicing aspects of the present disclosure.

One such embodiment is directed to a model for determining whether a FGF19 variant is a candidate for preventing a cancerous disease, disorder or condition in a subject having a metabolic disorder, the model comprising a subject that (i) does not exhibit an indicia of a cancerous condition prior to the administration of an effective amount of FGF19 or FGF19 surrogate, and (ii) exhibits an indicia of a cancerous condition after the administration of the FGF19 or the FGF19 surrogate; and wherein an indicia of a cancerous condition improves upon administration of an effective amount of a polypeptide comprising an amino acid sequence set forth in SEQ ID NO:1. In certain embodiments, the polypeptide consists of an amino acid sequence set forth in SEQ ID NO:1.

The present disclosure also contemplates a model for determining whether a FGF19 variant is a candidate for treating a cancerous disease, disorder or condition in a subject having a metabolic disorder, the model comprising a subject having at least one indicia of cancer resulting from administration of FGF19 or FGF19 surrogate, wherein the indicia of cancer improves upon administration of an effective amount of a polypeptide comprising an amino acid sequence set forth in SEQ ID NO:1. In certain embodiments, the polypeptide consists of an amino acid sequence set forth in SEQ ID NO:1.

In some embodiments, provided herein is a model for determining whether a FGF19 variant is a candidate for preventing a cancerous disease, disorder or condition in a subject having a metabolic disorder, the model comprising a subject that i) does not exhibit an indicia of a cancerous condition prior to the administration of an effective amount of FGF19 or FGF19 surrogate, and ii) exhibits an indicia of a cancerous condition after the administration of the FGF19 or FGF19 surrogate; and wherein an indicia of a cancerous condition improves upon administration of an effective amount of a FGF19 variant.

In other embodiments, provided herein is a model for determining whether a FGF19 variant is a candidate for treating a cancerous disease, disorder or condition in a subject having a metabolic disorder, the model comprising a subject having at least one indicia of cancer resulting from administration of FGF19 or FGF19 surrogate, wherein the indicia of cancer improves upon administration of an effective amount of a FGF19 variant.

In certain embodiments of the models provided herein, the FGF19 variant comprises an amino acid sequence set forth in any one of SEQ ID NOS:5-29; or a subsequence or fragment thereof. In other embodiments of the models provided herein, the FGF19 variant consists of an amino acid sequence set forth in any one of SEQ ID NOS: 5-29; or a subsequence or fragment thereof. In certain embodiments, the N-terminal R residue is deleted. In some embodiments, the FGF19 variant comprises or consists of SEQ ID NO:5. In other embodiments, the FGF19 variant comprises or consists of SEQ ID NO:6. In one embodiment, the FGF19 variant comprises or consists of SEQ ID NO:7. In other embodiments, the FGF19 variant comprises or consists of SEQ ID NO:8. In another embodiment, the FGF19 variant comprises or consists of SEQ ID NO:9. In some embodiments, the FGF19 variant comprises or consists of SEQ ID NO:10. In other embodiments, the FGF19 variant comprises or consists of SEQ ID NO:11. In another embodiment, the FGF19 variant comprises or consists of SEQ ID NO:12. In some embodiments, the FGF19 variant comprises or consists of SEQ ID NO:13. In other embodiments, the FGF19 variant comprises or consists of SEQ ID NO:14. In one embodiment, the FGF19 variant comprises or consists of SEQ ID NO:15. In another embodiment, the FGF19 variant comprises or consists of SEQ ID NO:16. In some embodiments, the FGF19 variant comprises or consists of SEQ ID NO:17. In other embodiments, the FGF19 variant comprises or consists of SEQ ID NO:18. In yet other embodiments, the FGF19 variant comprises or consists of SEQ ID NO:19. In some embodiments, the FGF19 variant comprises or consists of SEQ ID NO:20. In one embodiment, the FGF19 variant comprises or consists of SEQ ID NO:21. In some embodiments, the FGF19 variant comprises or consists of SEQ ID NO:22. In other embodiments, the FGF19 variant comprises or consists of SEQ ID NO:23. In another embodiment, the FGF19 variant comprises or consists of SEQ ID NO:24. In some embodiments, the FGF19 variant comprises or consists of SEQ ID NO:25. In other embodiments, the FGF19 variant comprises or consists of SEQ ID NO:26. In yet other embodiments, the FGF19 variant comprises or consists of SEQ ID NO:27. In some embodiments, the FGF19 variant comprises or consists of SEQ ID NO:28. In other embodiments, the FGF19 variant comprises or consists of SEQ ID NO:29. In certain embodiments, the FGF19 variant comprises or consists of any one of the foregoing sequences, wherein the N-terminal R residue is deleted. In some embodiments, the FGF19 variant comprises or consists of a subsequence of any of the foregoing sequences. In other embodiments, any combination of two or more of the foregoing FGF19 variants is also contemplated.

Evaluation of the Effect of FGF19 Co-Administered with a FGF19 Variant

In the examples set forth in the Experimental section, the impact on db/db mice of FGF19 administered alone or co-administered with the FGF19 variant M70 were assessed. Adeno-associated virus (AAV) was used as the vehicle to deliver and express exogenous genes of interest in the mice and to enable continuous, persistent and systemic exposure to proteins encoded by the transgenes.

Figure 2:
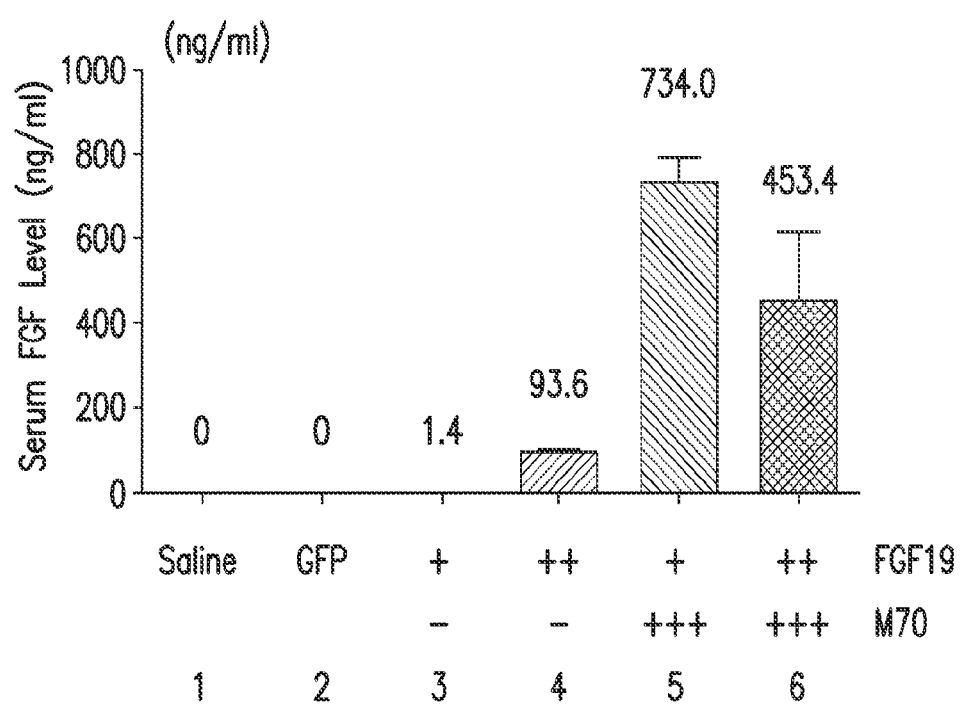
FIG. 2 depicts the plasma FGF19 concentrations determined by ELISA in db/db mice five weeks following AAV-mediated gene delivery (GFP as a control; FGF19; and/or M70).

FIG. 2 depicts plasma FGF19 concentrations determined by ELISA in db/db mice five weeks after AAV-mediated gene delivery of GFP (control); FGF19 (two separates doses); and FGF19 and FGF19 variant M70 (two separate doses of each). The high FGF19 concentrations observed following co-administration of the FGF19 and M70 transgenes reflect contributions from the expression of both FGF19 variant M70 and FGF19. FGF19-flag was used in the examples to facilitate quantification of the experimental results; as set forth in the Experimental section, the c-Flag component did not impact FGF19's tumorogenic effects, though it can have an impact FGF19's antidiabetic effects.

Figure 3:
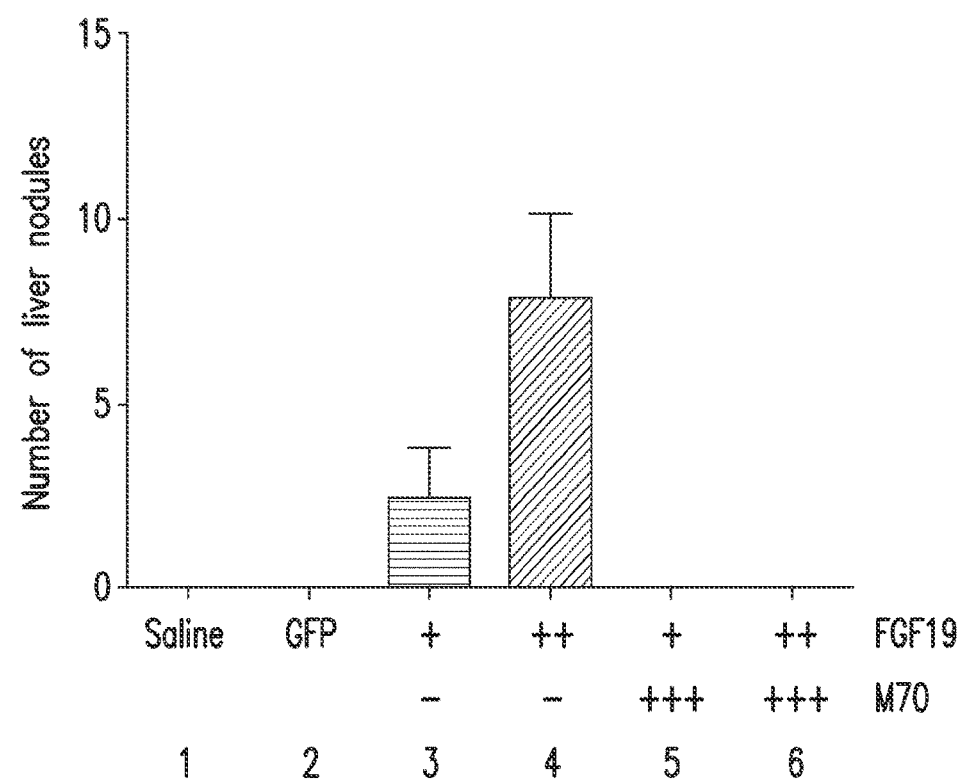
FIG. 3 depicts gross hepatic tumor nodule formation in db/db mice after continuous exposure to GFP; FGF19-flag; and/or M70 twenty-four weeks following AAV-mediated gene delivery.

The potential impact of co-administration of FGF19 and FGF19 variant M70 on HCC compared to administration of FGF19 alone was evaluated. As depicted in FIG. 3, ectopic expression of FGF19 in the db/db mouse model promoted the formation of multiple, large, raised tumor nodules protruding from the liver surface, whereas livers isolated from mice expressing both FGF19 and M70 were completely free (under the conditions employed) of hepatic nodules. Moreover, FGF19-mediated tumorigenesis, as evidenced by the appearance of hepatic lesions, is completely suppressed when the FGF19 and M70 transgenes are co-expressed. These data are surprising in that they suggest that not only does the engineered FGF19 variant M70 lack the tumorigenic potential in mice associated with the wild-type protein, but that it can effectively interfere with the proliferative effects of the wild-type protein. Although a precise understanding of the underlying mechanism of action associated with this phenomenon is not required in order to practice the present invention, it can be due, at least in part, to competition of M70 for wild-type FGF19 at the FGF19 binding site.

Figure 4:
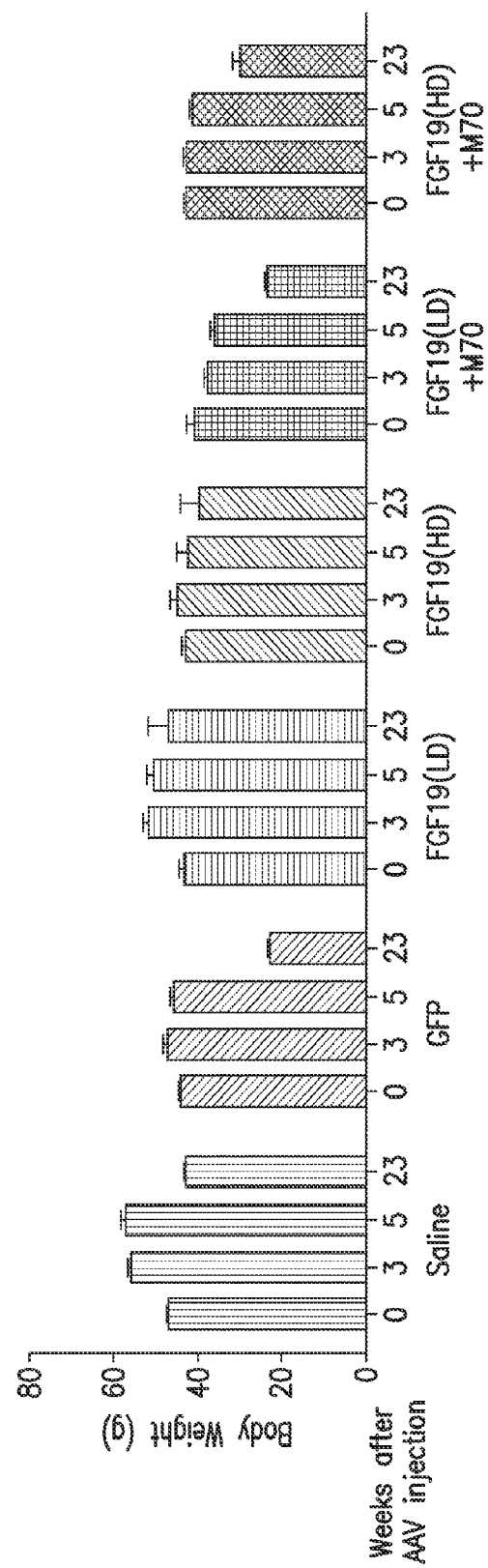
FIG. 4 depicts the effect on body weight, measured prior to injection and 3-, 5- and 23-weeks post-injection, in db/db mice after continuous exposure to GFP; FGF19-flag; and/or M70 following AAV-mediated gene delivery.

Example 4 sets forth the effect on mouse body weight initially measured prior to injection and subsequently determined 3-, 5- and 23-weeks post-injection of the indicated transgenes. As depicted in FIG. 4, transgenic db/db mice co-expressing the FGF19 variant M70 and FGF19 showed significant reductions in body weight compared to animals dosed with control, while less dramatic effects on body weight were observed in mice only expressing the FGF19 transgene. The changes in body weight observed in mice co-expressing the FGF19 and M70 transgenes were also reflected in reduced liver weights compared with weights of livers harvested from animals in the control group.

In a manner similar to that for determination of body weight, the effect of transgene expression on blood glucose was also evaluated prior to transgene injection and 3-, 5- and 23-weeks post-injection. The results, set forth in FIG. 5, indicate that transgenic db/db mice co-expressing the FGF19 variant M70 and FGF19 show significant reductions in blood glucose concentrations compared to control animals.

As an expansion of the above studies and date, and as provided in Examples 6-11 of the Experimental section, an in vivo tumorigenicity model was established in mice to evaluate FGF19-induced hepatocarcinogenicity in an effort to target FGF19 in tumorigenesis without compromising its essential roles, e.g., in bile acid homeostasis. Example 7 sets forth an AAV-mediated transgene system for evaluation of hepatocellular tumorigenesis in vivo. FGF19 transgene expression was introduced using an AAV-mediated gene delivery approach (Zhang et al., 2009, Hum. Gene Ther. 20, 922-929). As set forth in Example 8, a panel of FGF19 variants was evaluated in vivo and identified tumor-free variants including M70. Remarkably, as provided in Examples 8 and 9, M70 was shown to retain the beneficial activity of regulating bile acid homeostasis; and M70 was also shown to bind to and activate FGFR4, which is assumed to mediate FGF19-associated tumorigenicity (French et al., 2012, PloS one 7, e36713; Wu et al., 2010, J. Biol. Chem. 285, 5165-5170). As provided in Example 10, FGF19 was shown mechanistically to stimulate tumor progression by activating the STAT3 pathway, an activity eliminated in M70. Furthermore, as provided in Example 11, M70 was shown to inhibit FGF19-dependent tumor growth in multiple tumor models. Moreover, as provided in Example 12, M70 was shown to inhibit colon tumor growth in a syngenic mouse model.

Thus, in the examples provided herein, natural hormones are engineered to selectively eliminate potential deleterious activity (i.e., tumorigenicity), while leaving beneficial function (i.e., bile acid metabolism) intact. Through extensive structure activity analysis, M70 was identified as a tumor-free FGF19 variant that binds and selective activates FGFR4 receptor complex to maintain bile acid homeostasis. Mice with prolonged exposure to supra-physiological levels of M70 (24 weeks in db/db mice, 52 weeks in rasH2 mice) were free of liver tumors (Example 8; FIGS. 7 and 8). M70 was also demonstrated to block FGF19-associated tumorigenicity in mice and in human cancer xenografts (Example 11, FIG. 11). Although tumor-free FGF19 variants were identified previously (Wu et al., 2011, PloS one 6, e17868; Wu et al., 2010a, PNAS, 107, 14158-14163), these variants were specifically designed to eliminate FGFR4 binding, and by extension, were impaired in regulating bile acid metabolism. In contrast, M70 exhibits similar potency and efficacy in binding FGFR4 and regulating Cyp7a1 and pERK pathways downstream of FGFR4 (Examples 9 and 10; FIGS. 9 and 10). These results provide in vivo evidence of selective activation of FGFR4/KLB receptor complex, which does not lead to hepatocellular tumorigenesis.

The major differences between M70 and FGF19 lie in the N-terminus of the protein. Each FGF family protein consists of the structurally conserved central globular domain, and the flanking N-terminal and C-terminal segments that are structurally flexible and are divergent in primary sequences (Beenken and Mohammadi, 2009, Nat. Rev. Drug Discov. 8, 235-253). In X-ray crystal structures of multiple FGF/FGFR complexes, the N-terminal segment of the FGF molecule makes specific contact with the FGFR and is believed to play an important role determining the specificity of the FGF-FGFR interaction (Beenken and Mohammadi, 2009, Nat. Rev. Drug. Discov. 8, 235-253). Through our efforts of a systematic in vivo screen, changing 3 amino acids at the N-terminus coupled with a 5-aa deletion was shown to remove tumorigenicity without impairing its ability to activate FGFR4-dependent process such as bile acid regulation.

Without wishing to be bound by theory, several lines of evidence indicate that M70 exhibits pharmacologic characteristics of a "biased ligand" or a selective modulator. For example, as provided in Example 9 and FIG. 9, M70 binds to the extracellular domain of FGFR4 with similar potency and efficacy as wild type FGF19. M70 activates ERK phosphorylation in cells transfected with FGFR4-KLB or FGFR4 or cells expressing FGFR4-KLB endogenously. Like FGF19, M70 potently represses Cyp7a1 in primary hepatocytes and in mice. Unlike FGF19, M70 does not promote liver tumor formation. Again without wishing to be bound by theory, the lack of tumorigenicity by M70 could be explained by its lack of activation of pSTAT3, a key signaling molecule in hepatocellular carcinogenic pathways.

As provided in Example 10 and FIG. 10, FGF19, but not M70, was shown to activate STAT3 in the liver. STAT3 is a major player in hepatocellular oncogenesis (He and Karin, 2011, Cell Res. 21, 159-168). Phosphorylated (i.e. activated) STAT3 is found in approximate 60% of HCC in human (He et al., 2010, Cancer Cell 17, 286-297). STAT3 activation also correlates with poor prognosis in HCC patients (Calvisi et al., 2006, Gastroenterol. 130, 1117-1128). Constitutively-active STAT3 acts as an oncogene in cellular transformation (Bromberg et al., 1999, Cell 98, 295-303). Hepatocyte-specific ablation of STAT3 prevented HCC development in mice (He et al., 2010, Cancer cell 17, 286-297) Inhibitors of STAT3 activation block the growth of human cancer cells and are being tested in the clinic for treating various cancers including HCC (Chen et al., 2010, Clin. Cancer Res, 16, 5189-5199; Karras et al., 2000, Cellular immunol. 202, 124-135; Lin et al., 2009, Oncogene 28, 961-972). IL-6, among other inflammatory cytokines, is postulated to be the major STAT3 activator in the liver (He et al., 2010, (He et al., 2010, Cancer cell 17, 286-297). IL-6 signaling has been shown to stimulate malignant progression of liver cancer progenitors (He et al., 2013, Cell 155, 384-396). Increased IL-6 production was observed in patients with primary biliary cirrhosis, a cholestatic condition associated with increased HCC risk (Kakumu et al., 1993, Gastroenterologia Japonica 28, 18-24). FGF19 is also shown in Example 10 and FIG. 10 to activate STAT3 signaling in vivo. This effect could be directly mediated by FGFR4 receptor complex, or indirectly through induction of cytokines or growth factors. Indeed, the expression of IL-6 is elevated in the livers of FGF19-treated animals in our studies (Example 10; FIG. 10).

M70 may bind to an orthosteric site on FGFR4, since M70 is able to displace or interfere with FGF19 binding and inhibits FGF19-associated tumorigenicity. Yet M70 does not block all pathways nondiscriminatively to the same extent. M70 exhibits bias toward certain FGFR4 signaling pathways (i.e. Cyp7a1, pERK) to the relative exclusion of others (i.e., tumor), as observed for certain allosteric modulators (FIG. 12).

From a therapeutic perspective, our studies also provide experimental support for the use of M70 in chronic liver diseases and cancer. M70 can be useful as an anticancer agent for the treatment of FGF19-dependent tumors (see, e.g., Examples, 8 and 11; FIGS. 7, 8 and 11). This is particularly true given that FGF19 is amplified in ~15% human HCCs and is upregulated in cirrhosis and cholestatic conditions that often lead to tumor development. While a prior report showed development of a neutralizing anti-FGF19 monoclonal antibody that demonstrated anti-tumor activity in xenograft models (Desnoyers et al., 2008, Oncogene 27, 85-97), such a strategy caused serious adverse effects. Administration of this antibody to cynomolgus monkeys led to dose-related liver toxicity accompanied by severe diarrhea, due to on-target inhibition of endogenous FGF19, resulting in increased hepatic bile acid synthesis, elevated serum bile acid, perturbation of enterohepatic circulation, and the development of diarrhea and liver toxicity ((Pai et al., 2012, Toxicological sciences, 126, 446-456).).

As provided in the Experimental section, and in contrast to neutralizing antibodies, our studies show that M70 retains FGF19's activity on bile acid regulation, while eliminating tumorigenicity (see, e.g., Examples 8, 9 and 11; FIGS. 8, 9 and 11). This ensures preservation of bile acid homeostasis when used as an anti-cancer agent. Importantly, the experimental data provided herein shows that, not only does M70 lack the tumorigenic potential, but it can also effectively interfere with the tumorigenic effects associated with wild type FGF19. Furthermore, M70 inhibits the growth of colon cancer xenograft tumors, in addition to FGF19-mediated HCC. M70 also inhibits the growth of colon cancer in a syngenic mouse model (see, e.g., Example 12 and FIG. 13). These results confirm that, as a selective FGFR4 modulator, M70 antagonizes the oncogenic activity of FGF19.

As provided in the Experimental section, a robust, high throughput system was also established to evaluate multiple proteins in hepatocellular tumorigenesis in adult mice using AAV-mediated gene delivery. Overexpression of FGF19 at orthotopic site (liver) was shown to lead to liver dysplasia and the development of HCC in multiple strains of mice. This eliminates the confounding factors in embryogenesis and development in the traditional transgenic mice approach. No chemical tumor promoters such as diethylnitrosamine (DEN) or phenobarbital are needed for tumor initiation or promotion. The same approach can be adapted to evaluate other oncogenes, signaling proteins, as well as variants of natural proteins.

FGF19 demonstrates an array of biological effects. The therapeutic potential for FGF19 includes the treatment of chronic liver diseases, as well as obesity and diabetes, but its promotion of hepatocyte proliferation and carcinogenic potential challenges the development of FGF19 for chronic use. However, with the identification of M70 as an engineered FGF19 variant devoid of tumorigenicity while retaining its potent metabolic properties, therapeutic benefits could be achieved without unwanted side effects. Our results not only confirm that the selective activation of FGFR4-KLB receptor complex does not induce liver tumor formation, but further provide new avenues for utilizing this pathway to treat cancer, diseases with bile acid deregulation, type 2 diabetes, and other metabolic disorders.

Polypeptide and Nucleic Acid Molecules

The present disclosure also contemplates active fragments (e.g., subsequences) of the polypeptides containing contiguous amino acid residues derived from the polypeptide sequences described herein. The length of contiguous amino acid residues of a peptide or a polypeptide subsequence varies depending on the specific naturally-occurring amino acid sequence from which the subsequence is derived. In certain embodiments, peptides and polypeptides are from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, from about 50 amino acids to about 75 amino acids, from about 75 amino acids to about 100 amino acids, or from about 100 amino acids up to the full-length polypeptide.

In certain embodiments of the FGF19 variant polypeptides provided herein, the total number of amino acid residues (or mimetics thereof) is less than about 250. In other embodiments, the number of amino acid residues ranges from about 190 to about 230, from about 200 to about 225, or from about 210 to about 220 residues. In still further embodiments, the number of amino acid residues is greater than 180, greater than 185, greater than 190, greater than 195, greater than 200, greater than 205, greater than 210, greater than 215, greater than 220 or greater than 225 residues.

Additionally, in certain embodiments, the polypeptides have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, in some embodiments, a suitable polypeptide comprises an amino acid sequence having at least about 75%, at least about 80%, at least about 85%, at least about 90%, at least about 95%, at least about 98%, or at least about 99%, amino acid sequence identity to a contiguous stretch of from about 5 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, from about 90 amino acids to about 100 amino acids, from about 100 amino acids to about 110 amino acids, from about 110 amino acids to about 120 amino acids, from about 120 amino acids to about 130 amino acids, from about 130 amino acids to about 140 amino acids, from about 140 amino acids to about 150 amino acids, from about 150 amino acids to about 160 amino acids, from about 160 amino acids to about 170 amino acids, from about 170 amino acids to about 180 amino acids, from about 180 amino acids to about 190 amino acids, or about 194 amino acids, of one of the amino acid sequences described herein.

In certain embodiments, the polypeptides are isolated from a natural source (e.g., an environment other than its naturally-occurring environment) and also can be recombinantly made (e.g., in a genetically modified host cell such as bacteria; yeast; Pichia; insect cells; and the like), where the genetically modified host cell is modified with a nucleic acid comprising a nucleotide sequence encoding the polypeptide. The polypeptides can also be synthetically produced (e.g., by cell-free chemical synthesis). Methods of productions are described in more detail below.

In some embodiments, a polypeptide is generated using recombinant techniques to manipulate different FGF19-related nucleic acids known in the art to provide constructs capable of encoding the polypeptide. It will be appreciated that, when provided a particular amino acid sequence, the ordinary skilled artisan will recognize a variety of different nucleic acid molecules encoding such amino acid sequence in view of her background and experience in, for example, molecular biology.

In some embodiments, the present disclosure also provides polypeptides that have one or more alterations in the amino acid residues (e.g., at locations that are not conserved across variants or species) compared to a reference sequence (e.g., the corresponding wild-type sequence). Such polypeptides frequently retain domains that are conserved among species and have the same biological activity as the naturally-occurring polypeptides. Such polypeptides frequently also have one or more conservative amino acid substitutions. The phrase "conservative amino acid substitution" generally refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions preserve the activity of the protein by replacing an amino acid(s) in the protein with an amino acid with a side chain of similar acidity, basicity, charge, polarity, or size of the side chain. Guidance for substitutions, insertions, or deletions can be based on alignments of amino acid sequences of different variant proteins or proteins from different species.

In particular embodiments, modifications to the Loop-8 region of FGF19 are contemplated. Herein, FGF19 residues 127-129 (SEQ ID NO:3) are defined as constituting the Loop-8 region, although in the literature the Loop-8 region is sometimes defined as including or consisting of other residues (e.g., residues 125-129). Certain combinations of R127L and P128E substitutions to the FGF19 framework had an unexpectedly positive effect on HCC formation. A combination of R127L and P128E substitutions and a substitution of Gln (Q) for Leu (L) in the FGF19 core region also had significant effects on preventing HCC formation.

Accordingly, variants of the FGF19 Loop-8 region are included since they can reduce or eliminate substantial, measurable or detectable HCC formation. Furthermore, the effect of reducing HCC formation may be enhanced by modifications to amino acid residues outside of the Loop-8 region (e.g., substitutions of amino acid residues in the core region, such as the region corresponding to amino acids 21-29 of SEQ ID NO:3).

In some embodiments, the Loop-8 modified variant is M70: MRDSSPLVHYGWGDPIRLRHLYTSGPHGLSSC-FLRIRADGVVDCARGQSAHSLLEIKAVALR TVAIK-GVHSVRYLCMGADGKMQGLLQYSEEDCAFEEEI RPDGYNVYRSEKHRLPVSLS SAK QRQLYKNRGFL-PLSHFLPMLPMVPEEPEDLRGHL-ESDMFSSPLETDS16MDPFGLVTGLEAV RSPSFEK (SEQ ID NO:70), comprising a substitution in the FGF19 Loop-8 region (underlined). In certain embodiments, the Loop-8 modified M70 variant comprises a substitution in the FGF19 Loop-8 region (underlined) corresponding to (i) a R127L substitution, (ii) a P128E substitution, or (iii) a R127L substitution and a P128E substitution. In certain embodiments, the Loop-8 modified M70 variant further comprises or further comprises a substitution in the FGF19 core region. In some embodiments, the Loop-8 modified M70 variant comprises a L18Q substitution.

In other embodiments, the Loop-8 modified variant is M5 (SEQ ID NO:5), M6 (SEQ ID NO:6), M7 (SEQ ID N07), M14 (SEQ ID NO:8), M15 (SEQ ID NO:9), M32 (SEQ ID NO:10), M36 (SEQ ID NO:11), M43 (SEQ ID NO:12), M50 (SEQ ID NO:13), M52 (SEQ ID NO14), M53 (SEQ ID NO:15), M67 (SEQ ID NO:16), M68 (SEQ ID NO:17), M69 (SEQ ID NO:18), M70 (SEQ ID NO:1 or 19), M75 (SEQ ID NO:20), M76 (SEQ ID NO:21), M77 (SEQ ID NO22), M83 (SEQ ID NO:23), M84 (SEQ ID NO:24), M140 (SEQ ID NO:25), M5-R (SEQ ID NO:26), M6-R (SEQ ID NO:27), M50-R (SEQ ID NO:28), or M160 (SEQ ID NO:29). In some embodiments, the Loop-8 modified variant comprises a substitution in the FGF19 Loop-8 region corresponding to amino acids 127-129 of SEQ ID NO:3. In certain embodiments, the Loop-8 modified variant comprises a substitution in the FGF19 Loop-8 region corresponding to (i) a R127L substitution, (ii) a P128E substitution, or (iii) a R127L substitution and a P128E substitution. In some embodiments, the FGF19 variant comprises or further comprises a substitution in the core region corresponding to amino acids 21-29 of SEQ ID NO:3. In certain embodiments, the FGF19 variant comprises or further comprises a substitution in the core region corresponding to a L22Q substitution.

Nucleic acid molecules encoding the polypeptides described herein are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to a polypeptide due to degeneracy of the genetic code.

Amide Bond Substitutions

In some cases, a polypeptide includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of a polypeptide can be substituted.

In another example, one or more amide linkages (—CO—NH—) in a polypeptide can be replaced with a linkage which is an isostere of an amide linkage, such as —CH$_2$NH—, CH$_2$S—, —CH$_2$CH$_2$—, —CH=CH-(cis and trans), —COCH$_2$—, —CH(OH)CH$_2$— or —CH$_2$SO—. One or more amide linkages in a polypeptide can also be replaced by, for example, a reduced isostere pseudopeptide bond. See Couder et al. (1993) Int. J. Peptide Protein Res. 41:181-184. Such replacements and how to effect are known to those of ordinary skill in the art.

Amino Acid Substitutions

In certain embodiments, one or more amino acid substitutions are made in a polypeptide. The following are non-limiting examples:

a) a substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) a substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) a substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogen, oxygen or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) a substitution of side chain amide residue, including asparagine, glutamine, and alkyl or aromatic substitute derivatives of asparagine or glutamine; and/or f) a substitution of hydroxyl containing amino acids, including serine, threonine, homoserine, 2,3-diaminopropionic acid, and alkyl or aromatic substituted derivatives of serine or threonine.

In some embodiments, a polypeptide comprises one or more naturally occurring non-genetically encoded L-amino acids, synthetic L-amino acids or D-enantiomers of an amino acid. For example, a polypeptide can comprise only D-amino acids. For example, in certain embodiments, a polypeptide comprises one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

In some embodiments, a cysteine residue or a cysteine analog is introduced into a polypeptide to provide for linkage to another peptide via a disulfide linkage or to provide for cyclization of the polypeptide. Methods of introducing a cysteine or cysteine analog are known in the art; see, e.g., U.S. Pat. No. 8,067,532.

In other embodiments, a polypeptide is cyclized. For example, one or more cysteine or cysteine analogs can be introduced into a polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with amino acid and —(CH2)$_n$—CO— or —(CH2)$_n$—C$_6$H$_4$—CO—) with functional groups which allow for the introduction of a bridge. Some examples are disulfides, disulfide mimetics such as the —(CH2)$_n$-carba bridge, thioacetal, thioether bridges (cystathionine or lanthionine) and bridges containing esters and ethers. In these examples, n can be any integer, but is frequently less than ten.

Other exemplary modifications include, for example, an N-alkyl (or aryl) substitution (ψ[CONR]), or backbone crosslinking to construct lactams and other cyclic structures. Other derivatives of the modulator compounds of the present disclosure include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a polypeptide are replaced with a D-amino acid.

In some cases, a polypeptide is a retro-inverso analog (Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) Nature 368:744; and Brady et al. (1994) Nature 368:692.

A polypeptide can include a "Protein Transduction Domain" (PTD), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a polypeptide, while in other embodiments, a PTD is covalently linked to the carboxyl terminus of a polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:30); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila antennapedia* protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID N0:31); transportan GWTLNSAGYLLGKINLKALAALAKKIL (SEQ ID NO:32); KALAWEAKLAKALAKALAKHLAKALAKALKCEA (SEQ ID NO:33); and RQIKIWFQNRRMKWKK (SEQ ID NO:34). Exemplary PTDs include, but are not limited to, YGRKKRRQRRR (SEQ ID NO:30), RKKRRQRRR (SEQ ID NO:35); an arginine homopolymer of from 3 arginine residues to 50 arginine residues. Exemplary PTD domain amino acid sequences include, but are not limited to, any of the following: YGRKKRRQRRR (SEQ ID NO:30); RKKRRQRR (SEQ ID NO:36); YARAAARQARA (SEQ ID NO:37); THRLPRRRRRR (SEQ ID NO:38); and GGRRARRRRRR (SEQ ID NO:39).

The carboxyl group COR$_3$ of the amino acid at the C-terminal end of a polypeptide can be present in a free form (R$_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C$_1$-C$_6$-alkyl alcohols, e.g., ethyl alcohol or tert-butanol. The carboxyl group can also be amidated with primary or secondary amines such as ammonia, branched or unbranched C$_1$-C$_6$-alkylamines or C$_1$-C$_6$ di-alkylamines, e.g., methylamine or dimethylamine.

The amino group of the amino acid NR$_1$R$_2$ at the N-terminus of a polypeptide can be present in a free form (R$_1$=H and R$_2$=H) or in the form of a physiologically-tolerated salt such as, e.g., a chloride or acetate. The amino group can also be acetylated with acids such that R$_1$=H and R$_2$=acetyl, trifluoroacetyl, or adamantyl. The amino group can be present in a form protected by amino-protecting groups conventionally used in peptide chemistry such as, e.g., Fmoc, Benzyloxycarbonyl (Z), Boc, or Alloc. The amino group can be N-alkylated in which R$_1$ and/or R$_2$=C$_1$-C$_6$ alkyl or C$_2$-C$_8$ alkenyl or C$_7$-C$_9$ aralkyl. Alkyl residues can be straight-chained, branched or cyclic (e.g., ethyl, isopropyl and cyclohexyl, respectively).

Methods of Production of Polypeptides

A polypeptide of the present disclosure can be produced by any suitable method, including recombinant and non-recombinant methods (e.g., chemical synthesis).

A. Chemical Synthesis

Where a polypeptide is chemically synthesized, the synthesis can proceed via liquid-phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides of the present disclosure. Details of the chemical synthesis are known in the art (e.g., Ganesan A. 2006 Mini Rev. Med. Chem. 6:3-10; and Camarero J. A. et al., 2005 Protein Pept Lett. 12:723-8).

Solid phase peptide synthesis can be performed as described hereafter. The α functions (Nα) and any reactive side chains are protected with acid-labile or base-labile groups. The protective groups are stable under the conditions for linking amide bonds but can be readily cleaved without impairing the peptide chain that has formed. Suitable protective groups for the α-amino function include, but are not limited to, the following: t-butyloxycarbonyl (Boc), benzyloxycarbonyl (Z), o-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitro-sulfenyl, 2-cyano-t-butoxy-carbonyl, 9-fluorenylmethoxycarbonyl (Fmoc), 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl (2-CIZ), 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers and the like. Polystyrene (1%)-divinylbenzene or TentaGel® derivatized with 4-benzyloxybenzyl-alcohol (Wang-anchor) or 2-chlorotrityl chloride can be used if it is intended to prepare the peptidic acid. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material with the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, o-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or also in the absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, e.g., in a 2-fold excess and at temperatures between about 10° C. and 50° C., e.g., 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride under the conditions described above.

The Nα-protected amino acid (e.g., the Fmoc amino acid) can be coupled to the 2-chlorotrityl resin in dichloromethane with the addition of DIEA with reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained can be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Where a polypeptide is produced using recombinant techniques, the polypeptide can be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein can be isolated using metal chelate chromatography methods. Proteins can contain modifications to facilitate isolation.

The polypeptides can be prepared in substantially pure or isolated form (e.g., free from other polypeptides). The polypeptides can be present in a composition that is enriched for the polypeptide relative to other components that can be present (e.g., other polypeptides or other host cell components). For example, purified polypeptide can be provided such that the polypeptide is present in a composition that is substantially free of other expressed proteins, e.g., less than 90%, less than 60%, less than 50%, less than 40%, less than 30%, less than 20%, less than 10%, less than 5%, or less than 1%, of the composition is made up of other expressed proteins.

Therapeutic and Prophylactic Uses

Also provided herein are methods for treating or preventing hyperglycemia, hyperinsulinemia, glucose intolerance, glucose metabolism disorders, obesity and other body weight disorders, as well as other metabolic and metabolic-associated diseases, disorders and conditions by the administration of the agents, or compositions thereof. Furthermore, as described herein, the present disclosure provides methods for treating or preventing a host of other diseases, disorders and conditions. Such methods can also have an advantageous effect on one or more symptoms associated with a disease, disorder or condition by, for example, decreasing the severity or the frequency of a symptom. In certain embodiments, the method is a method for treating a disease or disorder. In other embodiments, the method is a method for preventing a disease or disorder.

In certain embodiments, the present disclosure contemplates methods of treating (or preventing, in certain circumstances) a subject having a metabolic disorder, the method comprising providing a subject having a metabolic disorder, wherein the subject exhibits an indicia of a FGF19-induced cancerous condition, and administering to the subject a therapeutically effective amount of a FGF19 variant identified from a pool of candidate FGF19 variant polypeptides as described herein; wherein there is an improvement in the metabolic disorder in the subject.

Non-limiting examples of diseases, disorders and conditions include: 1) glucose utilization disorders and the sequelae associated therewith, including diabetes mellitus (type I and type-2), gestational diabetes, hyperglycemia, insulin resistance, abnormal glucose metabolism, "pre-diabetes" (Impaired Fasting Glucose (IFG) or Impaired Glucose Tolerance (IGT)), and other physiological disorders associated with, or that result from, the hyperglycemic condition, including, for example, histopathological changes such as pancreatic β-cell destruction. Further hyperglycemic-related disorders include kidney damage (e.g., tubule damage or nephropathy), liver degeneration, eye damage (e.g., diabetic retinopathy or cataracts), and diabetic foot disorders; 2) dyslipidemias and their sequelae such as, for example, atherosclerosis, coronary artery disease, cerebrovascular disorders and the like; 3) other conditions which can be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension, cardiovascular disease, stroke and heart failure; 4) disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; 5) disorders of cell cycle or cell differentiation processes such as adipose cell tumors, lipomatous carcinomas including, for example, liposarcomas, solid tumors, and neoplasms; 6) neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; 7) skin and dermatological disorders and/or disorders of wound healing processes, including erythematosquamous dermatoses; and 8) other disorders such as syndrome X, osteoarthritis, and acute respiratory distress syndrome.

In order to determine whether a subject can be a candidate for the treatment or prevention of hyperglycemia, hyperinsulinemia, glucose intolerance, and/or glucose disorders by the methods provided herein, various diagnostic methods known in the art can be utilized (e.g., fasting plasma glucose (FPG) evaluation and the oral glucose tolerance test (oGTT)).

In order to determine whether a subject can be a candidate for the treatment or prevention of a body weight disorder (e.g., obesity) by the methods provided herein, parameters such as, but not limited to, the etiology and the extent of the subject's condition (e.g., how overweight the subject is compared to reference healthy individual) should be evaluated. For example, an adult having a BMI between ~25 and ~29.9 kg/m² can be considered overweight (pre-obese), while an adult having a BMI of ~30 kg/m² or higher can be considered obese. For subjects who are overweight and/or who have poor diets (e.g., diets high in fat and calories), it is common to initially implement and assess the effect of modified dietary habits and/or exercise regimens before initiating a course of therapy comprising one or more of the polypeptides of the present disclosure.

Also provided herein is a method of treating a subject (e.g., an animal, such as a human) having a metabolic or metabolic-associated disease, disorder or condition, said method comprising: (i) determining whether a test subject having a metabolic disorder is a candidate for treatment with a FGF19 variant, the method comprising: (a) providing a test subject having an indicia of a cancerous condition, the subject having a metabolic disorder, (b) co-administering FGF19 or a FGF19 surrogate, and a FGF19 variant to the test subject, wherein the amount of the FGF19 or the FGF19 surrogate administered to the test subject is sufficient to induce a cancerous condition in a reference population, and (c) determining whether an indicia of a cancerous condition is enhanced in the test subject; wherein the absence of enhancement of an indicia of a cancerous condition indicates that the test subject is a candidate for treatment with a FGF19 variant; and wherein if there is an absence of enhancement of the indicia of a cancerous condition in the test subject, then the method further comprises (ii) subsequently administering the FGF19 variant to the subject (e.g., an animal, such as a human). In certain embodiments, the subsequent administration of the FGF19 variant is a therapeutically effective amount resulting in the treatment of the metabolic or metabolic-associated disease, disorder or condition in the subject (e.g., an animal, such as a human).

Also provided herein is a method of treating a subject (e.g., an animal, such as a human) having a metabolic or metabolic-associated disease, disorder or condition, said method comprising: (i) determining whether a test subject having a metabolic disorder is a candidate for treatment with a FGF19 variant, the method comprising: (a) providing a test subject having an indicia of a cancerous condition, the test subject having a metabolic disorder, and (b) co-administering FGF19 or a FGF19 surrogate, and a FGF19 variant to the test subject, wherein the amount of the FGF19 or the FGF19 surrogate is administered to the test subject is sufficient to induce a cancerous condition in a reference population, and (c) determining whether an indicia of a cancerous condition is reduced in the test subject; wherein the reduction of an indicia of a cancerous condition indicates that the test subject is a candidate for treatment with a FGF19 variant; and wherein if there is a reduction of the indicia of a cancerous condition in the test subject, then the method further comprises (ii) subsequently administering the FGF19 variant to the subject (e.g., an animal, such as a human). In certain embodiments, the subsequent administration of the FGF19 variant is a therapeutically effective amount resulting in the treatment of the metabolic or metabolic-associated disease, disorder or condition in the subject (e.g., an animal, such as a human).

Also provided herein is a method of treating a subject (e.g., an animal, such as a human) having a metabolic or metabolic-associated disease, disorder or condition, said method comprising: (i) determining whether a FGF19 variant is a candidate for treating a test subject having a metabolic disorder, the method comprising: (a) co-administering FGF19 or a FGF19 surrogate, and the FGF19 variant to the test subject having a metabolic disorder, wherein the amount of the FGF19 or the FGF19 surrogate administered to the test subject is sufficient to induce a cancerous condition in a reference population, and (b) determining whether an indicia of a cancerous condition is observed in the test subject; wherein the absence of an indicia of a cancerous condition indicates that the FGF19 variant is a candidate for treatment of the test subject; and wherein if there is an absence of an indicia of a cancerous condition, then the method further comprises (ii) subsequently administering the FGF19 variant to the subject (e.g., an animal, such as a human). In certain embodiments, the subsequent administration of the FGF19 variant is a therapeutically effective amount resulting in the treatment of the metabolic or metabolic-associated disease, disorder or condition in the subject (e.g., an animal, such as a human).

Also provided herein is a method of treating a subject (e.g., an animal, such as a human) having a metabolic or metabolic-associated disease, disorder or condition, said method comprising: (i) determining whether a FGF19 variant is a candidate for treating a test subject having a metabolic disorder, the method comprising: (a) providing a test subject having a metabolic disorder, the test subject having an indicia of a cancerous condition, (b) co-administering FGF19 or a FGF19 surrogate, and a FGF19 variant to the test subject, wherein the amount of the FGF19 or the FGF19 surrogate is administered to the test subject is sufficient to exacerbate a cancerous condition in a reference population, and (c) determining whether an indicia of a cancerous condition is enhanced in the test subject; wherein the absence of exacerbation of an indicia of a cancerous condition indicates that the FGF19 variant is a candidate for treatment of the test subject; and wherein if there is an absence of enhancement of the indicia of a cancerous condition in the test subject, then the method further comprises (ii) subsequently administering the FGF19 variant to the subject (e.g., an animal, such as a human). In certain embodiments, the subsequent administration of the FGF19 variant is a therapeutically effective amount resulting in the treatment of the metabolic or metabolic-associated disease, disorder or condition in the subject (e.g., an animal, such as a human). In some embodiments, one or more indicia of a cancerous condition are reduced in the test subject.

Also provided herein is a method of treating a subject having a metabolic or metabolic-associated disease, disorder or condition, comprising: (a) providing a subject having a metabolic disorder, wherein the subject exhibits an indicia of a FGF19-induced cancerous condition, and (b) administering to the subject a therapeutically effective amount of a FGF19 variant identified in any one of methods or models provided herein; wherein there is an improvement in the metabolic or metabolic-associated disease, disorder or condition in the subject.

In certain embodiments of the methods provided herein, the subject is an animal. In other embodiments, the subject is a human. In some embodiments, the cancerous condition is a tumor. In certain embodiments, the tumor is a colon tumor or a hepatic tumor. In some embodiments, the metabolic or metabolic-associated disease, disorder or condition is a metabolic disorder. In some embodiments, the metabolic disorder is selected from the group consisting of a hyperglycemic condition, insulin resistance, hyperinsulinemia, glucose intolerance, obesity and metabolic syndrome. In one embodiment, the hyperglycemic condition is diabetes. In another embodiment, the treatment results in an improvement in the metabolic disorder. In certain embodiments, the improvement of the metabolic disorder is a decrease in blood glucose. In other embodiments, the improvement in the metabolic disorder in the subject is a decrease in body weight. In certain embodiments, the improvement in the metabolic disorder in the subject is a decrease in insulin.

In another aspect, provided herein is a method of antagonizing the oncogenic activity of FGF19, for example, using a FGF19 variant provided herein. In some embodiments, a cell expressing FGF19 is contacted with a FGF19 variant provided herein. In some embodiments, the FGF19 variant is M70. In certain embodiments, provided herein is a method of antagonizing the oncogenic activity of FGF19 in a subject, comprising administering to the subject a therapeutically effective amount of a FGF19 variant, thereby antagonizing the oncogenic activity of FGF19 in the subject. In some embodiments, provided is a method of preventing a FGF19-dependent disease, disorder or condition, or a symptom thereof, in a subject, comprising administering to the subject a therapeutically effective amount of a FGF19 variant, wherein the disease, disorder, condition, or symptom thereof is prevented in the subject. In other embodiments, provided is a method of treating a FGF19-dependent disease, disorder or condition, or a symptom thereof, in a subject, comprising administering to the subject a therapeutically effective amount of a FGF19 variant, wherein the disease, disorder, condition, or symptom thereof is treated in the subject.

In certain embodiments, the subject has a metabolic disorder and/or an indicia of a cancerous condition. In certain embodiments, the FGF19-dependent disease, disorder or condition is a cancer or tumor. In some embodiments, the cancer or tumor is a liver, colon, prostate or lung cancer or tumor. In some embodiments, the cancer or tumor is benign. In other embodiments, the cancer or tumor is malignant.

In certain embodiments, the subject has or is at risk of developing a FGF19-dependent disease, disorder or condition. In some embodiments, the FGF19-dependent disease, disorder or condition is a liver (hepatocellular) disease, disorder or condition, such as cirrhosis or cholestasis. In some embodiments, the liver disease or disorder is a chronic liver disease or disorder. In some embodiments, the FGF19-dependent disease, disorder or condition is cancer or tumor, such as HCC. In other embodiments, the FGF19-dependent disease, disorder or condition is not a liver disease, disorder or condition, such as cirrhosis or cholestasis. In some embodiments, the FGF19-dependent disease, disorder or condition is not a cancer or tumor, such as HCC. In some embodiments, the FGF19-dependent disease, disorder or condition is a colon cancer or tumor. In certain embodiments, the colon cancer or tumor is a colon adenocarcinoma. In some embodiments, the FGF19-dependent disease, disorder or condition is a prostate cancer or tumor. In yet other embodiments, the FGF19-depenndent disease, disorder or condition is a lung cancer or tumor. In certain embodiments, the lung cancer or tumor is a lung squamous cell carcinoma. In some embodiments, FGF19 is expressed in a primary or metastatic cancer or tumor cell. In certain embodiments, the FGF19-dependent disease, disorder or condition is precancerous. For example, cirrhosis and cholestasis sometimes to lead to liver cancers, such as HCC, and methods of treating or preventing such liver diseases and disorders are contemplated. In certain embodiments, the subject is a subject in need of prevention or treatment thereof. In some embodiments, administration of the FGF19 variant maintains bile acid homeostasis in the subject.

Also provided herein is a method of treating a cancer or tumor, such as a FGF19-dependent cancer or tumor, or a symptom thereof, in a subject, comprising administering to the subject a therapeutically effective amount of a FGF19 variant. In certain embodiments, the administration results in an improvement in the cancer, tumor or symptom thereof in the subject. In some embodiments, the method results in a reduction in tumor number, tumor size, or tumor weight. Also provided herein is a method of preventing a cancer or tumor, such as a FGF19-dependent cancer or tumor, or a symptom thereof, in a subject, comprising administering to the subject a therapeutically effective amount of a FGF19 variant. In some embodiments, the administration results in prevention of the cancer, tumor, or symptom thereof in the subject. In some embodiments, the method results in a reduction in tumor number, tumor size, or tumor weight. In a specific embodiment, the cancer or tumor is a FGF19-dependent cancer or tumor. In certain embodiments, the cancer or tumor is hepatocellular carcinoma. In some embodiments, the cancer or tumor is not hepatocellular carcinoma. In one embodiment, the cancer or tumor is a colon cancer or tumor. In some embodiments, the cancer or tumor is a prostate cancer or tumor. In certain embodiments, the cancer or tumor is a lung cancer or tumor. In certain embodiments, the FGF19 variant is a polypeptide comprising an amino acid sequence set forth in SEQ ID NO:1. In some embodiments, the FGF19 variant is a polypeptide consisting of an amino acid sequence set forth in SEQ ID NO:1. In certain embodiments, the subject is a subject in need thereof.

It is understood that any of the therapeutic or prophylactic methods provided herein can be used in conjunction with any of the models or other methods provided herein.

In certain embodiments of the methods provided herein, the FGF19 variant is selected from the group consisting of M5, M6, M7, M14, M15, M32, M36, M43, M52, M53, M67, M68, M69, M70, M75, M76, M77, M83, M84, M140, M144, M145, M146 and M160. In one embodiment, the FGF19 variant is M5. In another embodiment, the FGF19 variant is M6. In some embodiments, the FGF19 variant is M7. In one embodiment, the FGF19 variant is M14. In another embodiment, the FGF19 variant is M15. In other embodiments, the FGF19 variant is M32. In one embodiment, the FGF19 variant is M36. In another embodiment, the FGF19 variant is M43. In other embodiments, the FGF19 variant is M52. In yet other embodiment, the FGF19 variant is M53. In some embodiments, the FGF19 variant is M67. In one embodiment, the FGF19 variant is M68. In another embodiment, the FGF19 variant is M69. In some embodiments, the FGF19 variant is M70. In one embodiment, the FGF19 variant is M75. In another embodiment, the FGF19 variant is M76. In other embodiments, the FGF19 variant is M77. In yet other embodiments, the FGF19 variant is M83. In one embodiment, the FGF19 variant is M84. In another embodiment, the FGF19 variant is M140. In other embodiments, the FGF19 variant is M144. In yet other embodiments, the FGF19 variant is M145. In one embodiment, the FGF19 variant is M146. In some embodiments, the FGF19 variant is M160. In other embodiments, any combination of two or more of the foregoing FGF19 variants is also contemplated.

In some embodiments of the methods provided herein, the FGF19 variant comprises an amino acid sequence set forth in any one of SEQ ID NOS:5-29; or a subsequence or fragment thereof. In other embodiments of the methods provided herein, the FGF19 variant consists of an amino acid sequence set forth in any one of SEQ ID NOS: 5-29; or a subsequence or fragment thereof. In certain embodiments, the N-terminal R residue is deleted. In some embodiments, the FGF19 variant comprises or consists of SEQ ID NO:5. In other embodiments, the FGF19 variant comprises or consists of SEQ ID NO:6. In one embodiment, the FGF19 variant comprises or consists of SEQ ID NO:7. In other embodiments, the FGF19 variant comprises or consists of SEQ ID NO:8. In another embodiment, the FGF19 variant comprises or consists of SEQ ID NO:9. In some embodiments, the FGF19 variant comprises or consists of SEQ ID NO:10. In other embodiments, the FGF19 variant comprises or consists of SEQ ID NO:11. In another embodiment, the FGF19 variant comprises or consists of SEQ ID NO:12. In some embodiments, the FGF19 variant comprises or consists of SEQ ID NO:13. In other embodiments, the FGF19 variant comprises or consists of SEQ ID NO:14. In one embodiment, the FGF19 variant comprises or consists of SEQ ID NO:15. In another embodiment, the FGF19 variant comprises or consists of SEQ ID NO:16. In some embodiments, the FGF19 variant comprises or consists of SEQ ID NO:17. In other embodiments, the FGF19 variant comprises or consists of SEQ ID NO:18. In yet other embodiments, the FGF19 variant comprises or consists of SEQ ID NO:19. In some embodiments, the FGF19 variant comprises or consists of SEQ ID NO:20. In one embodiment, the FGF19 variant comprises or consists of SEQ ID NO:21. In some embodiments, the FGF19 variant comprises or consists of SEQ ID NO:22. In other embodiments, the FGF19 variant comprises or consists of SEQ ID NO:23. In another embodiment, the FGF19 variant comprises or consists of SEQ ID NO:24. In some embodiments, the FGF19 variant comprises or consists of SEQ ID NO:25. In other embodiments, the FGF19 variant comprises or consists of SEQ ID NO:26. In yet other embodiments, the FGF19 variant comprises or consists of SEQ ID NO:27. In some embodiments, the FGF19 variant comprises or consists of SEQ ID NO:28. In other embodiments, the FGF19 variant comprises or consists of SEQ ID NO:29. In certain embodiments, the FGF19 variant comprises or consists of any one of the foregoing sequences, wherein the N-terminal R residue is deleted. In some embodiments, the FGF19 variant comprises or consists of a subsequence of any of the foregoing sequences. In other embodiments, any combination of two or more of the foregoing FGF19 variants is also contemplated.

Pharmaceutical Compositions

The polypeptides of the present disclosure can be in the form of compositions suitable for administration to a subject. In general, such compositions are "pharmaceutical compositions" comprising one or more polypeptides and one or more pharmaceutically acceptable or physiologically acceptable diluents, carriers or excipients. In certain embodiments, the polypeptides are present in a therapeutically acceptable amount. The pharmaceutical compositions can be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions can be used in combination with other therapeutically active agents or compounds (e.g., glucose lowering agents) as described herein in order to treat or prevent the diseases, disorders and conditions as contemplated by the present disclosure.

The pharmaceutical compositions typically comprise a therapeutically effective amount of at least one of the polypeptides contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver the polypeptides, including implants (e.g., implantable pumps) and catheter systems, both of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections. In certain embodiments, the use of Nano Precision Medical's depot delivery technology (Nano Precision Medical; Emeryville, Calif.) is contemplated. The technology utilizes a titania nanotube membrane that produces zero-order release rates of macromolecules, such as protein and peptide therapeutics. The biocompatible membrane is housed in a small, subcutaneous implant that provides long-term (e.g., up to one year), constant-rate delivery of therapeutic macromolecules. The technology is currently being evaluated, e.g., for the delivery of GLP-1 agonists for the treatment of Type II diabetes.

The pharmaceutical compositions can be in the form of a sterile injectable aqueous or oleaginous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butanediol. Acceptable diluents, solvents and dispersion media that can be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil can be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient can be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration can be uncoated or coated by known techniques to delay disintegration and absorption in the gastrointestinal tract and thereby provide a sustained action. For example, a time-delay material such as glyceryl monostearate or glyceryl distearate can be employed. They can also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use can also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxy-ethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

Oily suspensions can be formulated by suspending the active ingredient in a vegetable oil, for example *arachis* oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure can also be in the form of oil-in-water emulsions. The oily phase can be a vegetable oil, for example olive oil or *arachis* oil, or a mineral oil, for example, liquid paraffin, or mixtures of these. Suitable emulsifying agents can be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, can be employed.

The present disclosure contemplates the administration of the polypeptides in the form of suppositories for rectal administration of the drug. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The polypeptides contemplated by the present disclosure can be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the disclosed polypeptides, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

Regarding antibodies, in an exemplary embodiment an antibody or antibody fragment of the present disclosure is stored at 10 mg/ml in sterile isotonic aqueous saline solution for injection at 4° C. and is diluted in either 100 ml or 200 ml 0.9% sodium chloride for injection prior to administration to the subject. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

Combination Therapy

The present disclosure contemplates the use of the FGF19 variant polypeptides identified herein in combination with one or more active therapeutic agents or other prophylactic or therapeutic modalities. In such combination therapy, the various active agents frequently have different mechanisms of action. Such combination therapy can be especially advantageous by allowing a dose reduction of one or more of the agents, thereby reducing or eliminating the adverse effects associated with one or more of the agents; furthermore, such combination therapy can have a synergistic therapeutic or prophylactic effect on the underlying disease, disorder, or condition.

As used herein, "combination" is meant to include therapies that can be administered separately, for example, formulated separately for separate administration (e.g., as can be provided in a kit), and therapies that can be administered together in a single formulation (i.e., a "co-formulation"). Combinations of the polypeptides identified using the methods and models described herein with one or more active therapeutic agents or other prophylactic or therapeutic modalities can be administered or applied sequentially (e.g., where one agent is administered prior to one or more other agents) or simultaneously (e.g., where two or more agents are administered at or about the same time). Regardless of whether the two or more agents are administered sequentially or simultaneously, they are considered to be administered in combination for purposes of the present disclosure.

Accordingly, methods and uses of the polypeptides identified through use of the methods and models described herein can be practiced prior to, substantially contemporaneously with or following another treatment, and can be supplemented with other forms of therapy. Supplementary therapies include other glucose lowering and/or weigh loss treatments, such as insulin, an insulin sensitivity enhancer and other drug treatments, a change in diet (low sugar, fats, etc.), weight loss surgery—(reducing stomach volume by gastric bypass, gastrectomy), gastric banding, gastric balloon, gastric sleeve, etc.

The present disclosure contemplates combination therapy with numerous agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA and ITCA 650 (an osmotic pump inserted subcutaneously that delivers an exenatide analog over a 12-month period; Intarcia, Boston, Mass.)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, RXR agonists, glycogen synthase kinase-3 inhibitors, immune modulators, beta-3 adrenergic receptor agonists, 1 lbeta-HSD1 inhibitors, and amylin analogues.

Furthermore, the present disclosure contemplates combination therapy with agents and methods for promoting weight loss, such as agents that stimulate metabolism or decrease appetite, and modified diets and/or exercise regimens to promote weight loss. Appetite suppression drugs are well known and can be used in combination with the methods provided herein.

The FGF19 variant polypeptides of the present disclosure can be used in combination with one or more other agent in any manner appropriate under the circumstances. In one embodiment, treatment with the at least one active agent and at least one polypeptide of the present disclosure is maintained over a period of time. In another embodiment, treatment with the at least one active agent is reduced or discontinued (e.g., when the subject is stable), while treatment with the polypeptide of the present disclosure is maintained at a constant dosing regimen. In a further embodiment, treatment with the at least one active agent is reduced or discontinued (e.g., when the subject is stable), while treatment with the polypeptide of the present disclosure is reduced (e.g., lower dose, less frequent dosing or shorter treatment regimen). In yet another embodiment, treatment with the at least one active agent is reduced or discontinued (e.g., when the subject is stable), and treatment with the polypeptide of the present disclosure is increased (e.g., higher dose, more frequent dosing or longer treatment regimen). In yet another embodiment, treatment with the at least one active agent is maintained and treatment with the polypeptide of the present disclosure is reduced or discontinued (e.g., lower dose, less frequent dosing or shorter treatment regimen). In yet another embodiment, treatment with the at least one active agent and treatment with the polypeptide of the present disclosure are reduced or discontinued (e.g., lower dose, less frequent dosing or shorter treatment regimen).

Dosing

The polypeptides of the present disclosure can be administered to a subject in an amount that is dependent upon, for example, the goal of the administration (e.g., the degree of resolution desired); the age, weight, sex, and health and physical condition of the subject to be treated; the nature of the polypeptide, and/or formulation being administered; the route of administration; and the nature of the disease, disorder, condition or symptom thereof (e.g., the severity of the dysregulation of glucose/insulin and the stage of the disorder). The dosing regimen can also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with absorption, distribution, metabolism, and excretion ("ADME"), taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the polypeptides of the present disclosure can be an amount that, when administered in one or more doses to a subject, produces a desired result relative to a healthy subject. For example, an effective dose can be one that, when administered to a subject having elevated plasma glucose and/or plasma insulin, achieves a desired reduction relative to that of a healthy subject by at least about 10%, at least about 20%, at least about 25%, at least about 30%, at least about 40%, at least about 50%, at least about 60%, at least about 70%, at least about 80%, or more than 80%.

An appropriate dosage level will generally be about 0.001 to 100 mg/kg of patient body weight per day, which can be administered in single or multiple doses. In some embodiments, the dosage level will be about 0.01 to about 25 mg/kg per day, and in other embodiments about 0.05 to about 10 mg/kg per day. A suitable dosage level can be about 0.01 to 25 mg/kg per day, about 0.05 to 10 mg/kg per day, or about 0.1 to 5 mg/kg per day. Within this range, the dosage can be 0.005 to 0.05, 0.05 to 0.5 or 0.5 to 5.0 mg/kg per day.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The polypeptides can be administered on a regimen of, for example, 1 to 4 times per day, and often once or twice per day.

The dosage of the polypeptides of the present disclosure can be repeated at an appropriate frequency, which can be in the range of once per day to once every three months, depending on the pharmacokinetics of the polypeptides (e.g. half-life) and the pharmacodynamic response (e.g. the duration of the therapeutic effect of the polypeptide). In some embodiments where the polypeptide is an antibody or a fragment thereof, or a polypeptide or variants thereof, dosing is frequently repeated between once per week and once every 3 months. In other embodiments, such polypeptides are administered approximately once per month.

In certain embodiments, the dosage of the disclosed polypeptides is contained in a "unit dosage form." The phrase "unit dosage form" refers to physically discrete units, each unit containing a predetermined amount of a polypeptide of the present disclosure, either alone or in combination with one or more additional agents, sufficient to produce the desired effect. It will be appreciated that the parameters of a unit dosage form will depend on the particular agent and the effect to be achieved. Exemplary unit doses can range from about 25-250; 250-500; 500-1,000; 1,000-2,500; 2,500-5,000; 5,000-25,000; or 25,000-50,000 ng; or from about 25-250; 250-500; 500-1,000; 1,000-2,500; 2,500-5,000; 5,000-25,000; 25,000-50,000 µg; or from about 25-250; 250-500; 500-1,000; 1000-2,500; 2,500-5,000; 5,000-25,000; or 25,000-50,000 mg.

Single or multiple doses can be administered, for example, multiple times per day, on consecutive days, alternating days, weekly or intermittently (e.g., twice per week, once every 1, 2, 3, 4, 5, 6, 7 or 8 weeks, or once every 2, 3, 4, 5 or 6 months).

Kits

The present disclosure also contemplates kits comprising the disclosed polypeptides, and pharmaceutical compositions thereof. The kits are generally in the form of a physical structure housing various components, as described below, and can be utilized, for example, in practicing the methods described above (e.g., administration of a polypeptide to a subject in need of restoring glucose homeostasis).

A kit can include one or more of the polypeptides disclosed herein (provided in, e.g., a sterile container), which can be in the form of a pharmaceutical composition suitable for administration to a subject. The polypeptides can be provided in a form that is ready for use or in a form requiring, for example, reconstitution or dilution prior to administration. When the polypeptides are in a form that needs to be reconstituted by a user, the kit can also include buffers, pharmaceutically acceptable excipients, and the like, packaged with or separately from the polypeptides. When combination therapy is contemplated, the kit can contain the several agents separately or they can already be combined in the kit. Each component of the kit can be enclosed within an individual container and all of the various containers can be within a single package. A kit of the present disclosure can be designed for conditions necessary to properly maintain the components housed therein (e.g., refrigeration or freezing).

A kit can contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert can be, e.g., integrated into the physical structure housing the components, contained separately within the physical structure, or affixed to a component of the kit (e.g., an ampoule, tube or vial). Exemplary instructions include those for reducing or lowering blood glucose, treatment of hyperglycemia, treatment of diabetes, etc. with the disclosed polypeptides, and pharmaceutical compositions thereof Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

In case of conflict, the specification, including definitions, will control. As used herein and in the appended claims, the singular forms "a," "an," and "the" include plural referents unless the context clearly dictates otherwise. Thus, for example, reference to "a peptide sequence" or a "treatment," includes a plurality of such sequences, treatments, and so forth. It is further noted that the claims can be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges, unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1000, 1000-2500, 2500-5000, 5000-25,000, or 5000-50,000 includes any numerical value or range within or encompassing such values, e.g., 25, 26, 27, 28, 29 . . . 250, 251, 252, 253, 254 . . . 500, 501, 502, 503, 504 . . . , etc. The use of a series of ranges includes combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the descriptions in the Experimental section are intended to illustrate but not limit the scope of invention described in the claims.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); s.c.=subcutaneous(ly); bid=twice daily; HPLC=high performance liquid chromatography; BW=body weight; U=unit; ns=not statistically significant; PG=fasting plasma glucose; FPI=fasting plasma insulin; ITT=insulin tolerance test; PTT=pyruvate tolerance test; oGTT=oral glucose tolerance test; GSIS=glucose-stimulated insulin secretion; AAV=adneno-associated virus; PBS=phosphate-buffered saline; PCR=polymerase chain reaction; NHS=N-Hydroxysuccinimide; DMEM=Dulbeco's Modification of Eagle's Medium; GC=genome copy; EDTA=ethylenediaminetetraacetic acid; FGF19CF=FGF19 with FLAG-tag at the C-terminus; GFP=green fluorescent protein; ELISA=enzyme-linked immunosorbance assay; ANOVA=analysis of variance; SEM=standard error of the mean.

Example 1

Materials and Methods for Examples 2-5

The following methods and materials were used in Examples 2-5 below.

Animals.

db/db mice (The Jackson Laboratory; Bar Harbor, Me.), approximately 15 weeks old mice and weighing approximately 36-48 g at initiation of treatment, were kept in accordance with welfare guidelines under controlled light (12-hour light and 12-hour dark cycle, dark 6:30 p.m.-6:30 a.m.), temperature (22±4° C.) and humidity (50%±20%) conditions. Mice had free access to autoclaved distilled water and were fed ad libitum a commercial diet (Harlan Laboratories, Indianapolis, Ind., Irradiated 2018 Teklad Global 18% Protein Rodent Diet) containing 18 kcal % fat, 24 kcal % protein and 58 kcal % carbohydrate. All animal studies were approved by the NGM Institutional Animal Care and Use Committee.

Nucleic Acid and Amino Acid Sequences.

FGF19 ORF (cDNA of ORF encoding hFGF19 (GenBank Accession No. NM_005117.2) and protein sequence encoded thereby (GenBank Accession No. NP_005108.1)) was amplified via PCR using recombinant DNA (cDNA) prepared from human small intestinal tissue. PCR reagent kits with Phusion® high-fidelity DNA polymerase ((F-530L; New England BioLabs; Ipswich, Mass.) were used with the following primers: forward PCR primer: 5' CCGACTAGTCACCatgcggagcgggtgtgtgg (SEQ ID NO:40), and reverse PCR primer: 5' ATAAGAATGCGGC-CGCTTACTTCTCAAAGCTGGGACTCCTC (SEQ ID NO:41).

Amplified DNA fragment was digested with Spe I and Not I (the restriction sites were included in the 5' or 3' PCR primers, respectively) and was then ligated with AAV transgene vectors that had been digested with the same restriction enzymes. The vector used for expression contained a selectable marker and an expression cassette composed of a strong eukaryotic promoter 5' of a site for insertion of the cloned coding sequence, followed by a 3' untranslated region and bovine growth hormone polyadenylation tail. The expression construct was also flanked by internal terminal repeats at the 5' and 3' ends.

Production and Purification of AAV Encoding FGF19 and FGF19 Variants.

AAV293 cells (Agilent Technologies, Santa Clara, Calif.) were cultured in Dulbeco's Modification of Eagle's Medium (DMEM, Mediatech, Herndon, Va.) supplemented with 10% fetal bovine serum and 1× antibiotic-antimycotic solution (Mediatech). The cells were plated at 50% density on Day 1 in 150-mm cell culture plates and transfected on Day 2, using calcium phosphate precipitation method, with the following three plasmids (20 μg/plate of each): i) AAV transgene plasmid, ii) pHelper plasmids (Agilent Technologies), and iii) AAV2/9 plasmid (Rabinowitz et al. 2002). Forty-eight hours after transfection, the cells were scraped off the plates, pelleted by centrifugation at 3000×g and re-suspended in buffer containing 20 mM Tris pH 8.5, 100 mM NaCl and 1 mM $MgCl_2$. The suspension was frozen in an alcohol dry ice bath and was then thawed in 37° C. water bath; the freeze-thaw cycle was repeated three times. Benzonase® (Sigma-Aldrich; St. Louis, Mo.) was added to 50 units/mL and deoxycholate was added to a final concentration of 0.25%. After incubation at 37° C. for 30 minutes, cell debris was pelleted by centrifugation at 5000×g for 20 minutes. Viral particles in the supernatant were purified using a discontinued iodixanal (Sigma-Aldrich) gradient as previously described (Zolotukhin et al., 2002) Endocrinology 143(5):1741-47. The viral stock was concentrated using Vivaspin® 20 (molecular weight (MW) cutoff 100,000 Da, Sartorius Stedim Biotech; Aubagne, France) and re-suspended in phosphate-buffered saline (PBS) with 10% glycerol and stored at −80° C.

To determine the viral genome copy (GC) number, 2 μL of viral stock was incubated in 6 μL of solution containing 50 units/mL Benzonase, 50 mM Tris-HCl pH 7.5, 10 mM $MgCl_2$, and 10 mM $CaCl_2$ at 37° C. for 30 minutes. Afterwards, 15 μL of the solution containing 2 mg/mL of Proteinase K, 0.5% SDS, and 25 mM EDTA were added and the mixture was incubated for an additional 20 minutes at 55° C. to release viral DNA. Viral DNA was cleaned with mini DNeasy® Kit (Qiagen; Valencia, Calif.) and eluted with 40 μL of water. Viral GC was determined using quantitative PCR. Viral stock was diluted with saline to the desirable GC/mL and the working solution (200 μL) was injected into mice via a tail vein.

Blood Glucose Assay.

Blood samples were collected from individual non-fasted animals by tail snip, and plasma glucose levels were measured using a glucometer (Accu-Chek® instruments; Roche Diagnostics, Indianapolis, Ind.) following manufacturer's instruction.

Serum FGF19 and FGF19 Variant Exposure Level Assay.

Whole blood (~50 μl/mouse) from mouse tail snips was collected into plain capillary tubes (BD Clay Adams SurePrep™, Becton Dickenson; Sparks, Md.). Serum and blood cells were separated by centrifugation for 10 mins at 10,000 rpm, 4° C. in an Autocrit™ Ultra 3 centrifuge (Becton Dickinson) and immediately frozen at −80° C. Levels of FGF19 and FGF19 variants were measured in serum using a commercially available ELISA (Biovendor; Asheville, N.C.) following the manufacturer's instructions. Human FGF19 was used as the standard and relative concentrations of M70 were determined. Relative concentrations of other FGF19 variants can be determined accordingly.

Fat Mass and Lean Mass Measurements.

Un-anesthetized animals were placed individually in a plastic holder and body composition determined using NMR-MRI (whole body composition analyzer, EchoMRI™, Houston, Tex.). Fat mass, lean mass, and water content (data not presented) were recorded. The entire procedure did not exceed 2 minutes for each animal.

Gross Liver Nodule Assessment.

Twenty-four weeks after AAV injection, animals were euthanized and individual livers were examined for gross nodule formation. The number of visible liver nodules (>2 mm in diameter) were counted and recorded.

Statistical Analysis.

All results were expressed as the mean±standard error of the mean (SEM). One-way ANOVA followed by Dunnett's post-test was used to compare data from multiple groups (GraphPad Prism®; San Diego, Calif.). When indicated, unpaired Student's t-test was used to compare two treatments. Two-way ANOVA followed by Bonferroni's post-test was use to compare multiple groups for time-course studies. A p-value of 0.05 or smaller was considered statistically significant.

Example 2

Plasma FGF19 Levels in Db/Db Mice Following Gene Delivery

A 24-week study was conducted in order to evaluate whether the FGF19 variant M70 was able to block FGF19-induced tumorigenicity in db/db mice. As an alternative to conventional methods of delivery, AAV was used in this example (and examples 2-4 that follow) as the vehicle to deliver and express exogenous genes of interest in mice and enable continuous, persistent and systemic exposure to proteins encoded by those transgenes.

Prior to gene delivery, mice were sorted into six groups (5 male mice/group) as set forth in Table 1, and blood glucose and body weight measurements were recorded for each mouse.

TABLE 1

| Group | AAV Construct | Dose Level (AAV) | Volume (mL/mouse) | Descriptor |
|---|---|---|---|---|
| 1 | Saline | 0 | 0.2 | Control |
| 2 | GFP | 3e11 | 0.2 | AAV-Control |
| 3 | FGF19-flag | 3e9 | 0.2 | FGF19 Low Dose |
| 4 | FGF19-flag | 3e10 | 0.2 | FGF19 High Dose |
| 5 | M70 | 3e11 | 0.2 (total) | M70/FGF19 Low Dose |
|   | FGF19-flag | 3e9 |   |   |
| 6 | M70 | 3e11 | 0.2 (total) | M70/FGF19 High Dose |
|   | FGF19-flag | 3e10 |   |   |

At week 0, mice were injected either with 0.2 mL saline or 0.2 mL of one of the AAV constructs from Groups 2-6. At weeks 3 and 5, blood glucose and body weight measurements were again recorded for each mouse in Groups 1-6.

Five weeks after gene delivery, FGF19 concentrations were measured in sera isolated from mice injected either with saline (Group 1) or AAV constructs (Groups 2-6). Since the ELISA used to measure drug concentrations was unable to accurately distinguish between FGF19 and M70, plasma levels determined for Groups 5 and 6 represent the total plasma concentrations of both proteins.

The results are set forth in FIG. 2. FGF19 levels detected in mice receiving low (3e9; Group 3) and high (3e10; Group 4) doses of recombinant FGF19-flag virus were proportional to AAV dose (1.4±0.5 ng/mL and 93.6±12.6 ng/mL, respectively). In mice injected with both the FGF19-flag and M70 transgenes, the M70 virus (3e11) was present at either 100- or 10-fold excess compared with the FGF19-flag construct alone. As a result of co-injecting the two transgenes, high serum levels of FGF19 were detected at both low and high doses of FGF19-flag (734.0±61.1 ng/mL (Group 5) and 453.4±169.4 ng/mL (Group 6), respectively), representing contributions from the expression of both M70 and FGF19-flag. In contrast, FGF19 was undetectable in samples isolated from db/db mice injected with either saline or AAV-GFP.

At week 23, blood glucose and body weight measurements were again recorded for each mouse. Twenty-four weeks after gene delivery, all animals were euthanized and subjected to necropsy.

Example 3

FGF19-Mediated Formation of Gross Hepatic Nodules in Db/Db Mice in the Absence and Presence of FGF19 Variant M70

Using the euthanized animals from Example 2, livers from individual mice were examined, and the numbers of visible liver nodules were determined. The results are set forth in FIG. 3. References to Group numbers refer to Table 1.

As depicted in FIG. 3, ectopic expression of FGF19-flag in the db/db mouse model promoted the formation of multiple, large, raised nodules protruding from the liver surface at both low (3e9; Group 3)) and high (3e10; Group 4) viral doses (2.4±1.4 lesions per liver and 7.8 lesions per liver, respectively). By comparison, livers isolated from mice expressing both FGF19-flag and M70 were completely free of hepatic nodules (Group 5 and Group 6). Results are expressed as the mean and SEM for all animals within the same study group. It should be noted that the c-Flag component did not impact FGF19's tumorogenic effects, though it can impact FGF19's antidiabetic effects.

Ectopic expression of FGF19-flag promotes the formation of hepatic nodules in db/db mice at serum concentrations as low as 1 ng/mL. However, FGF19-mediated tumorigenesis, as evidenced by the appearance of hepatic lesions, is completely suppressed when the FGF19-flag and M70 transgenes are co-expressed in this model. These data suggest that not only does the engineered FGF19 variant M70 lack the tumorigenic potential in mice associated with the wild-type protein, but that it can effectively interfere with the proliferative effects of the wild-type protein.

Example 4

Effects of Transgene Expression on Body Weight and Composition in Db/Db Mice

As alluded to in Example 2, 15-week-old male db/db mice (n=5) were injected with 0.2 mL saline or recombinant AAV transgenes as indicated in Table 1. Body weights were measured for each mouse prior to injection (week −1) and 3-, 5- and 23-weeks post-injection. The results, set forth in FIG. 4, are expressed as the mean of individual measurements from all animals and SEM.

Transgenic db/db mice co-expressing M70 and FGF19-flag (Groups 5 and 6) showed significant reductions in body weight as compared with animals dosed with saline (Group 1). Less dramatic effects on body weight were observed in mice expressing the FGF19-flag transgene, although the reductions appeared to be dose-dependent and were significant at weeks 3 and 5 in animals injected with the higher dose (Groups 3 and 4).

Note that mice in both control groups (dosed either with saline (Group 1) or AAV-GFP (Group 2)), tended to show significant loss of mass by the end of the study, compared with their maximum body weights in weeks 3 and 5 following gene delivery. The body weight loss in these animals is commonly associated with the severe hyperglycemia observed in db/db mice and the progression of type 2 diabetes during the course of the 24-week study.

The changes in body weight observed in mice co-expressing the FGF19-flag and M70 transgenes were reflected in reduced liver weights compared with those harvested from animals in the saline group (data not shown); notably, the reduced organ size was directly proportional to the lower body weight in these mice. In contrast, the relative liver weight was increased in mice expressing FGF19-flag, although these changes were similarly not significant when normalized to body weight (data not shown)

In addition, the effects of treatment on body composition were determined 23-weeks post-injection using NMR-MRI. Consistent with the observed reductions in body weight, ectopic co-expression of the M70 and FGF19-flag transgenes resulted in the loss of both fat mass and lean mass in db/db mice compared with mice treated with saline (data not shown). Expression of FGF19-flag had little effect on body composition in db/db mice receiving either the low or high dose of the transgene (data not shown).

Example 5

Effects of Transgene Expression on Non-Fasted Blood Glucose in Db/Db Mice

Figure 5:
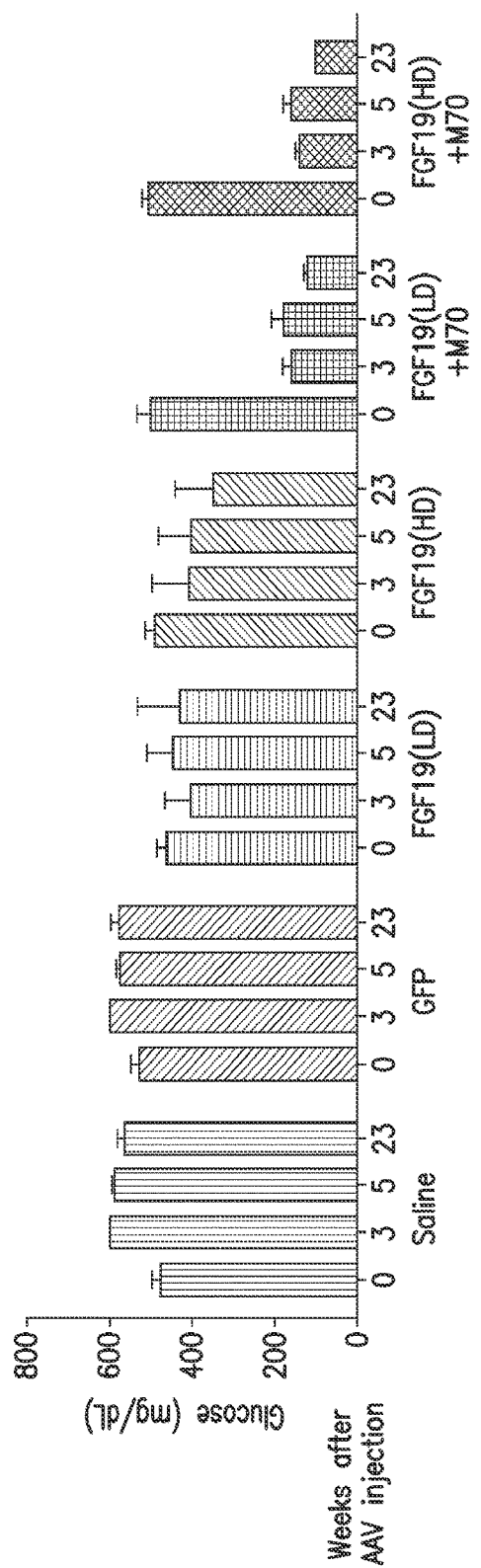
FIG. 5 depicts the effect on glucose concentration, measured prior to injection and 3-, S- and 23-weeks post-injection, in db/db mice after continuous exposure to GFP; FGF19-flag; and/or M70 following AAV-mediated gene delivery.

As alluded to in Example 2, 15-week-old male db/db mice (n=5) were injected with 0.2 mL saline or recombinant AAV transgenes as indicated in Table 1. Blood glucose was measured for each mouse prior to injection (week −1) and 3-, 5- and 23-weeks post-injection. The results, set forth in FIG. 5, are expressed as the mean of individual measurements from all animals and SEM.

Transgenic db/db mice co-expressing M70 and FGF19-flag (Groups 5 and 6) showed significant reductions in blood glucose concentrations as compared with control animals (Groups 1 and 2). Glucose levels were reduced rapidly in mice co-expressing the FGF19-flag and M70 transgenes, reaching plateau levels by approximately 3 weeks after gene delivery (160 and 141 mg/dL at the high dose (Group 6) and low dose (Group 5) of FGF19-flag transgene, respectively). The blood glucose levels in mice expressing FGF19-flag (Groups 3 and 4) were significantly lower than in control groups, and maintained at initial baseline levels (approximately 400-450 mg/dL) during the course of the 24-week study. As previously indicated, although the c-Flag component did not impact FGF19's tumorogenic effects, it can impact FGF19's antidiabetic effects. The low systemic levels of FGF19-flag detected in these mice appear to provide some protection against the deteriorating glycemia observed in mice treated with saline or AAV-GFP, but fail to lower glucose levels below the baseline values.

As would be expected, no glucose-lowering was observed during the course of the study following injection with saline (Group 1) or a control virus, AAV-GFP (Group 2). Of note, the blood glucose concentrations determined by glucometer in the control groups (~600 mg/dL) represent the upper limit of detection by the instrument and may underrepresent the actual glucose concentration in these samples.

Example 6

Materials and Methods for Examples 7-11

The following methods and materials were used in Examples 7-16 below.

DNA Constructs.

Human FGF19 (NM_005117), human FGFR4 (NM_022963), mouse FGFR4 (NM_008011), human KLB (NM_175737) and mouse KLB (NM_031180) cDNAs were purchased from Genecopoeia. Mutations were introduced in the FGF19 constructs using the QuickChange™ Site-Directed Mutagenesis kit (Stratagene).

Production and Purification of AAV Encoding FGF19 and FGF19 Variants.

AAV293 cells (Agilent Technologies, Santa Clara, Calif.) were cultured in Dulbeco's Modification of Eagle's Medium (DMEM, Mediatech, Herndon, Va.) supplemented with 10% fetal bovine serum and 1× antibiotic-antimycotic solution (Mediatech). The cells were plated at 50% density on Day 1 in 150-mm cell culture plates and transfected on Day 2, using calcium phosphate precipitation method, with the following three plasmids (20 µg/plate of each): i) AAV transgene plasmid, ii) pHelper plasmids (Agilent Technologies), and iii) AAV2/9 plasmid (Rabinowitz et al. 2002). Forty-eight hours after transfection, the cells were scraped off the plates, pelleted by centrifugation at 3000×g and re-suspended in buffer containing 20 mM Tris pH 8.5, 100 mM NaCl and 1 mM $MgCl_2$. The suspension was frozen in an alcohol dry ice bath and was then thawed in 37° C. water bath; the freeze-thaw cycle was repeated three times. Benzonase® (Sigma-Aldrich; St. Louis, Mo.) was added to 50 units/mL and deoxycholate was added to a final concentration of 0.25%. After incubation at 37° C. for 30 minutes, cell debris was pelleted by centrifugation at 5000×g for 20 minutes. Viral particles in the supernatant were purified using a discontinued iodixanal (Sigma-Aldrich) gradient as previously described (Zolotukhin et al., (2002) Endocrinology 143(5):1741-47. The viral stock was concentrated using Vivaspin® 20 (molecular weight (MW) cutoff 100,000 Da, Sartorius Stedim Biotech; Aubagne, France) and re-suspended in phosphate-buffered saline (PBS) with 10% glycerol and stored at −80° C.

To determine the viral genome copy (GC) number, 2 µL of viral stock was incubated in 6 µL of solution containing 50 units/mL Benzonase, 50 mM Tris-HCl pH 7.5, 10 mM $MgCl_2$, and 10 mM $CaCl_2$ at 37° C. for 30 minutes. Afterwards, 15 µL of the solution containing 2 mg/mL of Proteinase K, 0.5% SDS, and 25 mM EDTA were added and the mixture was incubated for an additional 20 minutes at 55° C. to release viral DNA. Viral DNA was cleaned with mini DNeasy® Kit (Qiagen; Valencia, Calif.) and eluted with 40 µL of water. Viral GC was determined using quantitative PCR. Viral stock was diluted with saline to the desirable GC/mL and the working solution (200 µL) was injected into mice via a tail vein.

Animal Experiments.

All animal studies were approved by the Institutional Animal Care and Use Committee at NGM. Mice were housed in a pathogen-free animal facility at 22° C. under controlled 12 hour light/12 hour dark cycle. All mice were kept on standard chow diet (Harlan Laboratories, Teklad 2918) and autoclaved water ad libitum. Male mice were used unless otherwise specified. C57BL/6J, FVB/NJ, BDF, ob/ob, and db/db mice were purchased from Jackson Laboratory. Heterozygous rasH2 transgenic mice were obtained from Taconic. On Day −7, cohorts of 10-12 week old ob/ob or db/db mice, or 6-8 week old C57BL/6J, FVB/NJ, BDF, or rasH2 mice, were randomized into treatment groups based on body weight. All animals received a single 200 µL intravenous injection of $3\times10^{11}$ genome copies of AAV via tail vein on Day 1. Body weights were recorded and blood was collected via tail snip for measurement of serum FGF levels. Animals were euthanized and livers were collected 24 or 52 weeks after dosing with AAV.

Gross, Histological, and Immunohistochemical Analysis.

To determine the onset of liver changes in mice injected with AAV-FGF19, gross and histological evaluations were performed at designated intervals throughout the course of a year. Body weight, liver weight, and liver tumor nodule numbers were recorded upon necropsy. For tumor score calculation for FGF19 variants, tumor score=number of tumor nodules on the entire surface of the liver expressing variant/number of tumor nodules on the entire surface of the liver expressing wild type FGF19. Therefore FGF19-expressing mice were given a tumor score with an arbitrary value of 1. Formalin-fixed paraffin-embedded tissue sections were stained with hematoxylin and eosin (H & E) for histological assessment of hepatocytic hyperplasia, hypertrophy, or neoplasia. When indicated, liver sections were treated for antigen retrieval using citrate buffer (Vector Laboratories) and then incubated with 10 µg/mL anti-PCNA (Dako), anti-Ki67 (Dako), anti-glutamine synthetase (Thermofisher), or anti-β-catenin antibodies (Cell Signaling). Biotinylated secondary antibody, ABC-HRP reagent, and DAB colorimetric peroxidase substrate (Vector Laboratories) were used for detection. For LacZ staining, livers were embedded in OCT and sectioned on Cryostat. Tissue sections were fixed in PBS containing 4% paraformaldehyde and 2% glutaraldehyde for 10 minutes and incubated with 1 mg/mL X-gal (Promega) in 5 mM potassium ferrocyanide and 5 mM potassium ferricyanide at 37° C. for 2 hours.

Luciferase Assays.

Rat L6 myoblasts were obtained from American Type Culture Collection (ATCC) and cultured in Dulbecco's Modified Eagle Medium (DMEM) supplemented with 10% fetal bovine serum (FBS) at 37° C. under 5% CO2. Cells in 96-well plates were transiently transfected with expression vectors encoding mouse KLB, mouse FGFR4, GAL4-Elk-1 transcriptional activator (pFA2-Elkl, Stratagene), firefly luciferase reporter driven GAL4 binding sites (pFR-luc, Stratagene), and Renilla luciferase (pRL-SV40, Promega), using FuGENE® 6 transfection reagent (Roche Applied Science). The day after transfection, the cells were stimulated for 6 hours with ligands in serum free media containing 20 µg/mL heparin (Sigma). Cells were lysed with lysis buffer (Promega) and luciferase activity was determined using Dual-Glo® Luciferase Assay System (Promega) and EnSpire® Plate Reader (Perkin Elmer). Firefly luciferase activity was normalized to the co-expressed Renilla luciferase activity and shown as mean±SEM of three replicates.

Cyp7a1 Expression in Primary Hepatocytes.

Primary hepatocytes from mouse, rat or human livers (Life Technologies) were plated on collagen I-coated 96-well plates (Becton Dickinson) and incubated overnight in Wiliams' E media supplemented with 100 nM dexamethasone and 0.25 mg/mL matrigel. Cells were treated with recombinant FGF19 or M70 proteins for 24 hours (mouse or rat hepatocytes) or 6 hours (human hepatocytes). Cyp7a1 expression in cell lysates was determined by qRT-PCR analysis using QuantiTect multiplex qRT-PCR master mix (Qiagen) and premade primers and probes (Life Technologies; mouse Cyp7a1: Mm00484150_m1; rat Cyp7a1: Rn00564065_m1; human Cyp7a1: Hs00167982_m1). Reactions were performed in triplicates on Applied Biosystems 7900HT Sequence Detection System. Relative mRNA levels were calculated by the comparative threshold cycle method using 18S RNA (mouse and rat) or actin (human) as the internal standard.

In Vivo Signaling Analysis.

db/db mice (9-11 week old) (Jackson Laboratories) were given intraperitoneal (i.p.) injections (1 mg/kg) of FGF19 or M70 recombinant proteins. Livers were collected 15 minutes, 2 hours or 4 hours after injection and snap frozen in liquid nitrogen. Frozen liver samples were homogenized in RIPA lysis buffer (50 mM Tris pH7.5, 150 mM NaCl, 1% NP40 and 0.5% sodium deoxycholic acid, 1 mM dithiothereitol, 1 mM PMSF, 2 mM sodium fluoride, and 2 mM sodium orthovanadate) containing protease inhibitors (Roche) and phosphatase inhibitors (Sigma). Equal amounts of protein (15 µg), as determined by BCA assay (Thermo Fisher), were separated on 4-20% polyacrylamide gels (Bio-Rad) and transferred to nitrocellulose membranes (Bio-Rad). Membranes were blocked in 5% non-fat dry milk in PBS/0.05% Tween 20 and incubated with antibodies to pSTAT3 (Cell Signaling), STAT3 (Cell Signaling), or antibody cocktail I (Cell Signaling). Bound antibodies were detected with horse radish peroxidase (HRP)-conjugated secondary reagents and visualized using Odyssey® scanner (Li-Cor Biotechnology).

Xenograft Experiments.

6-8 week old athymic nu/nu female mice (Charles River Laboratories) were injected subcutaneously in the flanks with $5\times10^6$ cells (200 µL/mouse). Mice bearing tumors of similar volumes (~100 mm$^3$) were randomized into groups and treated via one-time tail vein injection of $3\times10^{11}$ AAV-M70 or a control virus (AAV-GFP). Tumors were measured with an electronic caliper and average tumor volume was calculated using the formula: (W2×L)/2, where W and L are the smaller and large diameter, respectively.

Statistical Analysis.

All results are expressed as the mean±standard error of the mean (SEM). One-way ANOVA followed by Dunnett's post-test was used to compare data from multiple groups (GraphPad Prism®). When indicated, unpaired Student's t-test was used to compare two treatment groups. Two-way ANOVA followed by Bonferroni's post-test was used to compare multiple groups for time-course studies. A p-value of 0.05 or smaller was considered statistically significant.

Example 7

An AAV-Mediated Transgene System for Evaluation of Hepatocellular Tumorigenesis In Vivo AAV-mediated gene delivery provides a means to achieve continuous transgene expression without inflammatory responses that are commonly associated with other viral vectors (Zaiss et al., 2002, J. Virol. 76, 4580-4590). Sustained expression of up to 1 year has been observed with the AAV gene delivery method when introduced into adult mice (Rivera et al., 1999, PNAS 96, 8657-8662). The first AAV vector was recently approved as a treatment for a genetic disorder in human (Wirth et al., 2013, Gene 525, 162-169).

Figure 6A:
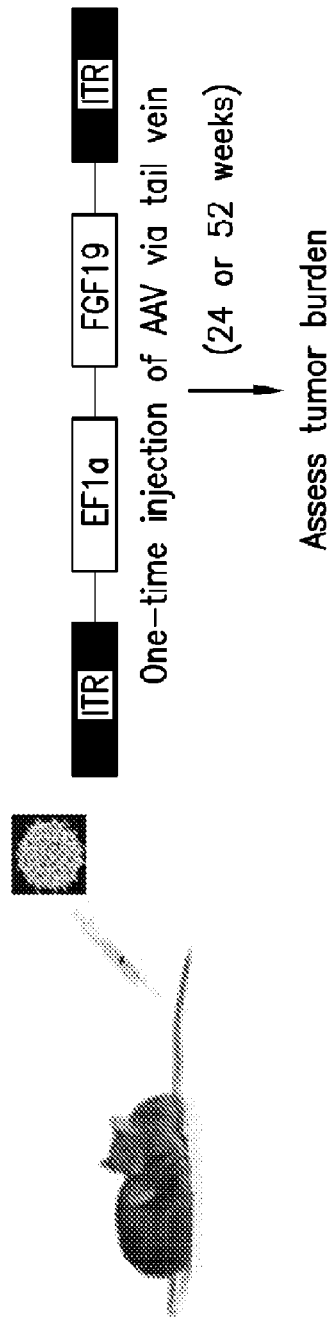
FIGS. 6A-6E depict an AAV-mediated transgene system for studying hepatocellular tumorigenesis. (A) A diagram of experimental protocol. Mice were given a single injection of $3\times10^{11}$ genome copies of AAV-FGF19 via tail vein when 6-12 week old. Mice were sacrificed 24 or 52 week later for liver tumor analysis. ITR, inverted terminal repeat; EF1a, elongation factor 1α promoter. (B) Representative livers of db/db mice 24 weeks after administration of AAV-FGF19. Multiple, large, raised tumors protruding from the hepatic surface were observed in db/db mice expressing FGF19. No liver tumor was observed in animals injected with a control virus (AAV-GFP) in this experiment. Scale bars, 10 mm. (C) Serum levels of FGF19 were measured by ELISA at 1, 4, 12, and 24 weeks after AAV administration in db/db mice (n=5). All values represent mean±SEM. (D) Liver tumor multiplicity, size, and scoring in db/db mice expressing FGF19 transgene. Tumors per liver were counted and maximal tumor sizes were measured. The mean in each group is indicated by horizontal lines (n=15 per group, each dot represents an individual animal). All values represent mean±SEM. ***$p<0.001$, *$p<0.05$ denote significant differences vs. control group by two-tailed t test. (E) Histological and immunohistochemical characterization of FGF19-induced liver tumors in db/db mice. The columns are, from top to bottom: hematoxylin and eosin (H & E) staining of liver sections; immunohistochemical detection of Ki-67, PCNA, glutamine synthetase, and β-catenin. FGF19-induced neoplastic cells are strongly glutamine synthetase-positive. Tumors (T) are outlined by dotted lines. Scale bars, 100 μm.

In previously reported FGF19 transgenic model, FGF19 was ectopically expressed in the skeletal muscle, a non-physiological site of FGF19 expression (Inagaki et al., 2005, Cell Metabol. 2, 217-225; Nicholes et al., 2002, Amer. J. Pathol. 160, 2295-2307). Under pathological conditions such as cirrhosis or cholestasis, FGF19 expression is induced in the liver (Desnoyers et al., 2008, Oncogene 27, 85-97; Hasegawa Y, 2013, Hepatol. 58, 802A; Schaap et al., 2009, Hepatol. 49, 1228-1235). As an alternative to conventional methods of generating transgenic mice, FGF19 was introduced via AAV in 6-12 week old mice (FIG. 6A). The primary tissue of transgene expression is liver using this approach, with only marginal expression in heart and muscle (data not shown). 90-100% transduction of hepatocytes and long-term gene expression without toxicity following a single administration of AAV were observed as previously reported (Zincarelli et al., 2008, Mol. Ther. 16, 1073-1080) (data not shown).

Multiple mouse strains were evaluated for latency and robustness of FGF19-mediated liver tumor formation (Table 2). A control AAV virus (AAV-GFP, green fluorescent protein) did not produce any liver tumors (Table 2).

As shown in Table 2, FGF19 Promotes Hepatocarcinogenesis in Multiple Mouse Models. Various strains of mice (6-12 week old) were injected with $3\times10^{11}$ genome copies of AAV vectors encoding FGF19 or a control gene (GFP, green fluorescent protein). Tumor incidence was determined at 24 or 52 weeks after AAV administration. n.d., not determined.

TABLE 2

| Mouse strain | FGF19 | | Control | |
|---|---|---|---|---|
| | 24 weeks | 52 weeks | 24 weeks | 52 weeks |
| C57BL6/J | 0/5 | 4/5 (80%) | 0/5 | 0/5 |
| BDF | 0/5 | 5/5 (100%) | 0/5 | 0/5 |
| FVB/N | 0/5 | 3/5 (60%) | 0/5 | 0/5 |
| ob/ob | 3/5 (60%) | n.d. | n.d. | n.d. |
| db/db | 5/5 (100%) | n.d. | n.d. | n.d. |

In general, mice injected with AAV-GFP exhibited similar phenotype as saline-injected animals (data not shown). For simplicity, only results from AAV-GFP-injected animals were shown as controls in the following studies.

Figure 6B:
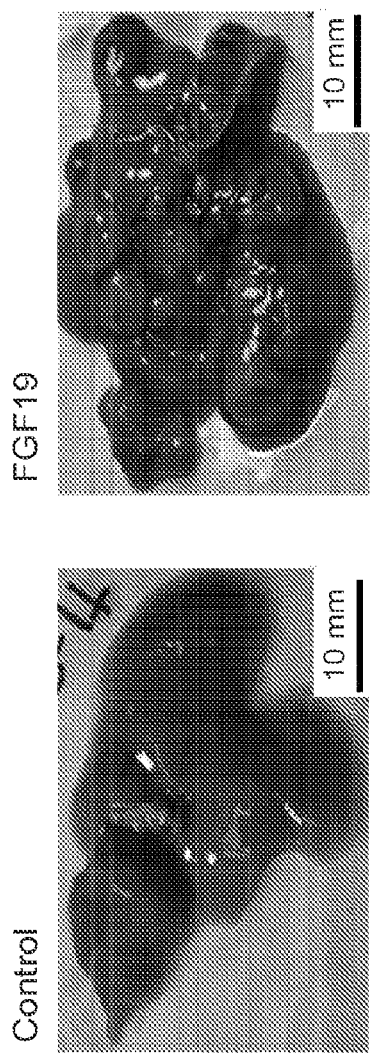

Interestingly, the tumor latency varied depending upon the mouse genetic background. Mutations in leptin receptor are frequently found in cirrhotic livers and are linked to HCC in human (Ikeda et al., 2014, Gastroenterol., 146:222-232; Wang et al., 2010, World J. Gastroenterol. 16, 5801-5809). db/db mice, which have a genetic defect in leptin receptor (Tartaglia et al., 1995, Cell 83, 1263-1271), provide a clinically relevant genetic context for evaluating candidate HCC-promoting genes. Indeed, among several mouse strains tested, db/db mice exhibited the shortest latency and high tumor penetrance, with the appearance of multiple, large, raised tumor nodules protruding from the liver surface 24 weeks following AAV-FGF19 delivery (FIG. 6B).

Figure 6C:
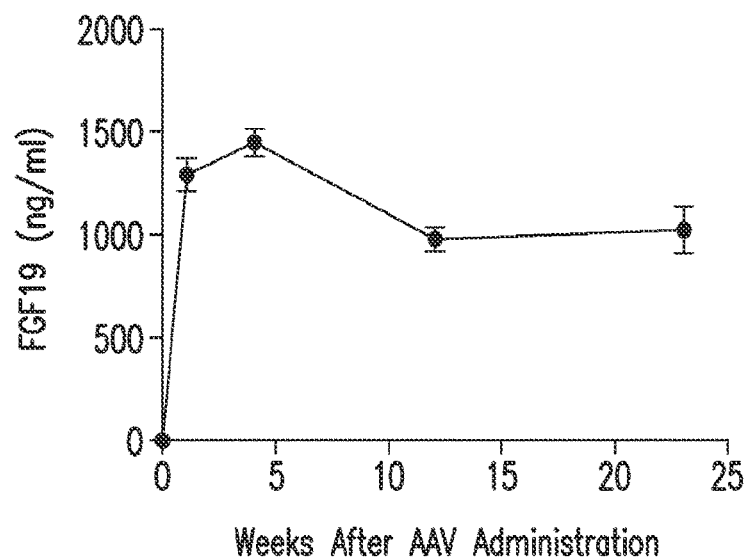
Figure 6D:
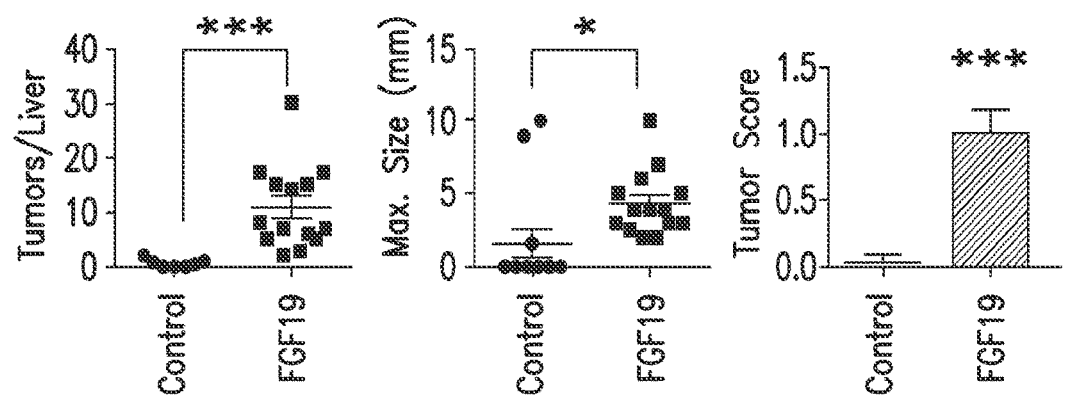

Serum FGF19 levels reached ~1 µg/ml, 1 week after single tail vein injection of $3\times10^{11}$ genome copies of AAV-FGF19 in db/db mice (FIG. 6C). No FGF19 was detected in mice injected with control virus. The high circulating levels of FGF19 persisted throughout the 24-week study period (FIG. 6C). Visible tumor nodules on the entire surface of the liver were counted (FIG. 6D). The maximum diameter of the liver tumor nodules was recorded (FIG. 6D). Occasionally a few liver tumor nodules were observed in db/db mice injected with control virus or saline, probably reflecting increased background in tumorigenesis in this genetic model (FIG. 6D and data not shown). A tumor score system was established based on the multiplicity of liver tumor nodules as described in the materials and methods (Example 6) (FIG. 6D).

Figure 6E:
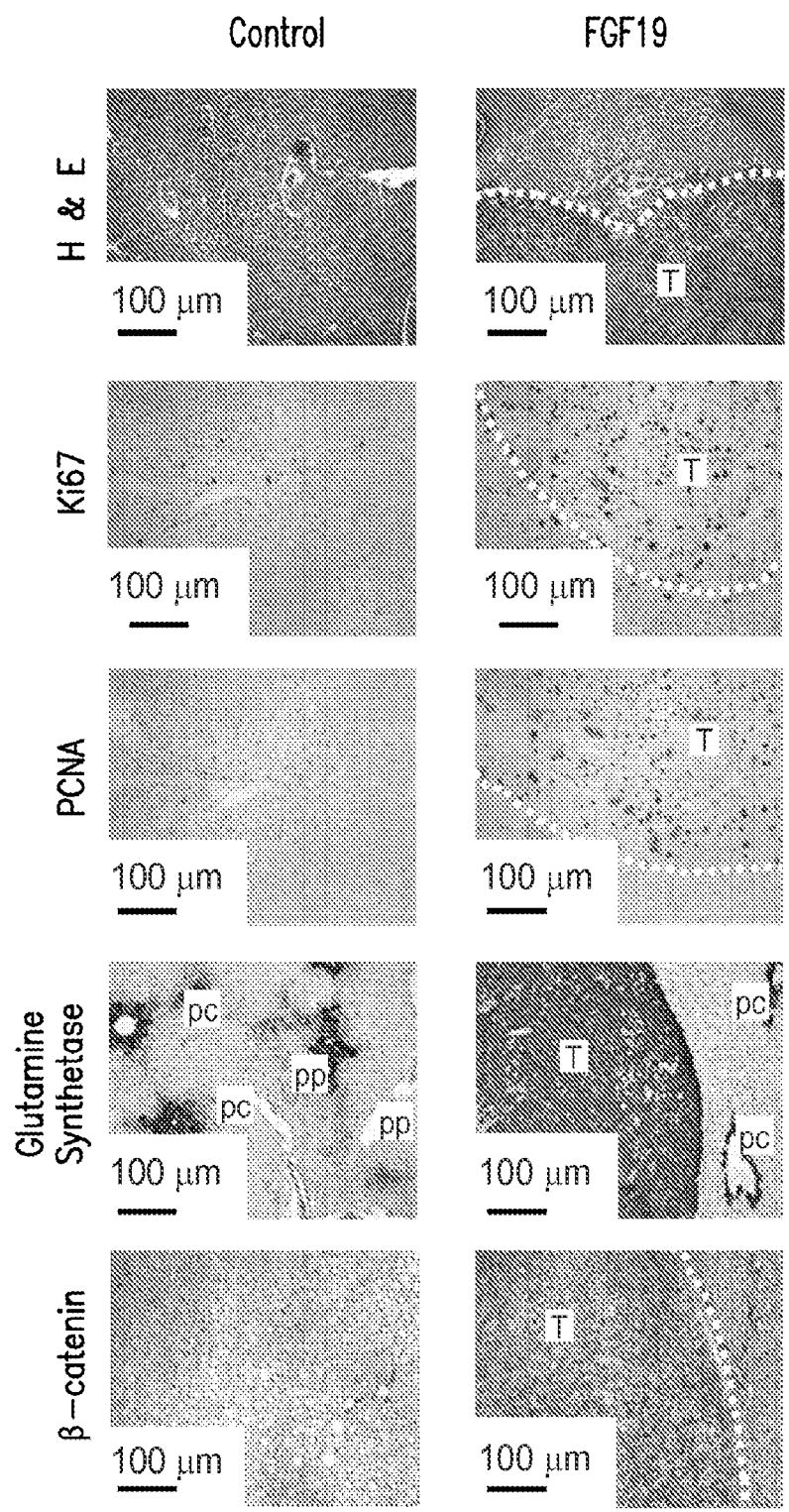

Microscopic examination of classified the AAV-FGF19-induced in situ liver tumors as solid HCCs, which resembled those reported in FGF19-transgenic animals (FIG. 6E). Cellular proliferative status, examined by immunohistochemical staining for Ki-67 and PCNA, indicated that the tumors were highly proliferative. Similar to what was observed in FGF19-transgenic mice, liver tumors in AAV-FGF19 mice were glutamine synthetase-positive, suggestive of a pericentral origin (Nicholes et al., 2002, Amer. J. Pathol. 160, 2295-2307) (FIG. 6E). Liver tumors from AAV-FGF19 mice also showed increased nuclear staining for β-catenin (FIG. 6E). Thus, the AAV-mediated transgene expression provides a robust system to evaluate FGF19-induced hepatocarcinogenesis in vivo.

Example 8

M70 is an Engineered, Tumor-Free FGF19 Variant

FGF19 and FGF21 belong to the same FGF subfamily, sharing 34% amino acid identity. Interestingly, unlike FGF19, FGF21 does not induce liver tumor formation in our AAV-mediated transgene models (data not shown). In order to identify structural elements that are crucial for tumorigenicity induced by FGF19, a number of chimeric constructs between FGF19 and FGF21 were generated by systematically swapping predicted secondary structural elements including α-strands and β-helices (Table 3). Table 3 shows chimeric constructs with amino acid sequences derived from FGF19 or FGF21. Liver tumor formation was assessed 24 weeks after AAV-mediated transgene expression. Secondary structural components (β-sheets and loops between β-sheets) of FGF19 are replaced systematically. Constructs were individually introduced into db/db mice by AAV to assess their tumorigenic potential after 24 weeks of continuous exposure. The N-terminal 10-20 amino acids of FGF19 were identified as being critical for tumorigenicity (Table 3).

TABLE 3

| Name | Amino Acids from FGF19 | Amino Acids from FGF21 | Tumor Score |
|---|---|---|---|
| Control | | | 0.00 ± 0.00 |
| FGF19 | R23-K216 | | 1.00 ± 0.18 |
| FGF21 | | H28-S208 | 0.00 ± 0.00 |
| FGF19 "end swap" variants: | | | |
| N-ter | R23-R43 | H28-R44 | 0.00 ± 0.00 |
| C-ter | P170-K216 | R162-S208 | 2.70 + 0.50 |
| FGF19 "loop swap" variants: | | | |
| Loop-1 | S50-L56 | D51-T56 | 0.59 + 0.29 |
| Loop-2 | R63-G66 | R63-G66 | 2.55 + 0.34 |
| Loop-3 | A71-A76 | A71-P76 | 1.58 + 0.51 |
| Loop-4 | A86-T89 | K86-V89 | 1.69 + 0.27 |
| Loop-5 | G94-S97 | G94-T97 | 0.90 + 0.17 |
| Loop-6 | A105-G107 | P105-G107 | 1.00 + 0.17 |
| Loop-7 | L112-S116 | S112-D129 | 0.67 + 0.18 |
| Loop-8 | R127-D129 | L127-D129 | 0.06 + 0.03 |
| Loop-9 | S136-H139 | S136-H139 | 0.79 + 0.10 |
| Loop-10 | V1434-L162 | L143-K149 | 1.32 + 0.22 |
| Loop-11 | R157-H164 | R158-G168 | 1.24 + 0.38 |
| FGF19 "sheet swap" variants: | | | |
| Sheet-1 | R43-T49 | R44-T50 | 0.32 + 0.14 |
| Sheet-2 | S57-I62 | E57-I62 | 0.35 + 0.10 |
| Sheet-3 | V67-A71 | T67-A71 | 1.78 + 0.14 |
| Sheet-4 | L80-V85 | L80-L85 | 3.99 + 0.63 |
| Sheet-5 | T89-K93 | V89-L93 | 0.38 + 0.05 |
| Sheet-6 | V98-G104 | S98-R104 | 0.73 + 0.17 |
| Sheet-7 | K108-G111 | A108-G111 | 1.91 + 0.66 |
| Sheet-8 | F122-R127 | F122-L127 | 0.94 + 0.21 |
| Sheet-9 | G130-S138 | G130-S136 | 1.17 + 0.22 |
| Sheet-10 | R140-P142 | G140-P142 | 2.00 + 0.41 |
| Sheet-11 | F165-M168 | R158-A161 | 0.38 + 0.31 |

Subsequently, additional constructs were generated by only altering amino acids within this region (Table 4). Table 4 shows the structure activity relationship analysis of FGF19 variants in the N-terminal region. Amino acid changes from wild type FGF19 are underlined. Liver tumor formation was assessed 24 weeks after transgene expression.

TABLE 4

| Name | N-terminal Sequence | Tumor Score |
|---|---|---|
| Control | | 0.00 ± 0.00 |
| FGF19 | RPLAFSDAGPHVHYGWGDPIRLRHLYTSGPHGLSS | 1.00 ± 0.18 |
| FGP19 N-terminal SAR variants: | | |
| N1 | R-----DAGPHVHYGWGDPIRLRHLYTSGPHGLSS | 1.25 ± 0.30 |
| N2 | R----------VHYGWGDPIRLRHLYTSGPHGLSS | 0.00 ± 0.00 |
| SSL | R-----D__SS__PLVHYGWGDPIRLRHLYTSGPHGLSS | 0.00 ± 0.00 |
| SSH | R-----D__SS__PHVHYGWGDPIRLRHLYTSGPHGLSS | 2.39 ± 0.93 |
| SGL | R-----D__S__GP__L__VHYGWGDPIRLRHLYTSGPHGLSS | 0.68 ± 0.14 |
| ASL | R-----DA__S__P__L__VHYGWGDPIRLRHLYTSGPHGLSS | 1.09 ± 0.18 |
| EDL | R-----D__ED__P__L__VHYGWGDPIRLRHLYTSGPHGLSS | 1.18 ± 0.45 |
| EGL | R-----D__EG__P__L__VHYGWGDPIRLRHLYTSGPHGLSS | 1.15 ± 0.17 |

TABLE 4-continued

| Name | N-terminal Sequence | Tumor Score |
|------|---------------------|-------------|
| EDH | R-----DEDPHVHYGWGDPIRLRHLYTSGPHGLSS | 1.00 ± 0.36 |
| EGH | R-----DEGPHVHYGWGDPIRLRHLYTSGPHGLSS | 1.44 ± 0.05 |
| QGH | R-----DQGPHVHYGWGDPIRLRHLYTSGPHGLSS | 1.01 ± 0.16 |
| QGL | R-----DQGPLVHYGWGDPIRLRHLYTSGPHGLSS | 0.68 ± 0.12 |
| QSH | R-----DQSPHVHYGWGDPIRLRHLYTSGPHGLSS | 1.42 ± 0.20 |
| ESH | R-----DESPHVHYGWGDPIRLRHLYTSGPHGLSS | 1.22 ± 0.31 |
| QSL | R-----DQSPLVHYGWGDPIRLRHLYTSGPHGLSS | 1.08 ± 0.33 |
| ESL | R-----DESPLVHYGWGDPIRLRHLYTSGPHGLSS | 0.01 ± 0.01 |

Figure 7A:
FIGS. 7A-7H depict M70 is a tumor-free FGF19 variant after continuous exposure in db/db mice for 24 weeks. (A) Alignment of protein sequences of M70 and FGF19 in the N-terminal region. Mutations introduced into M70 are underlined. (B)-(F) Number of tumors per liver (B), liver weight (C), and ratio of liver to body weight (D) of db/db mice expressing FGF19 or M70 for 24 weeks (n=5 per group). Growth curve (E) and serum levels of transgene expression (F) were also determined. (G) Representative liver sections from db/db mice after 24 weeks of transgene expression. The liver panel columns are, from top to bottom.

Overall, more than 30 FGF19 variants were individually assessed for their tumorigenicity. A FGF19 variant carrying 3 amino acid substitutions (A30S, G31 S, H33L) and a 5-amino acid deletion, referred as M70 (SEQ ID NO:1), was selected for further studies (FIG. 7A).

Figure 7B:
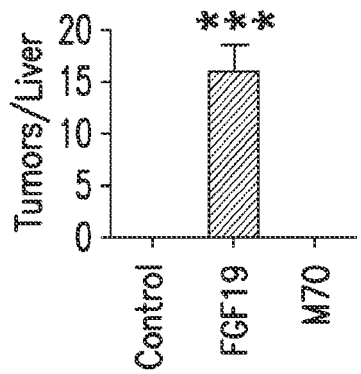
Figure 7C:
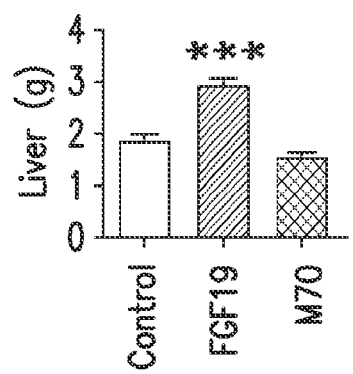
Figure 7D:
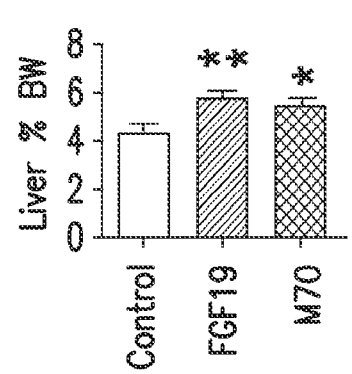
Figure 7E:
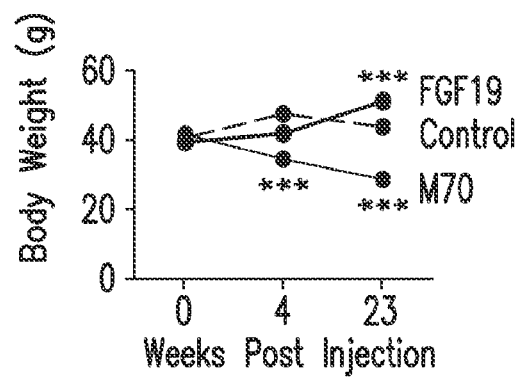
Figure 7F:
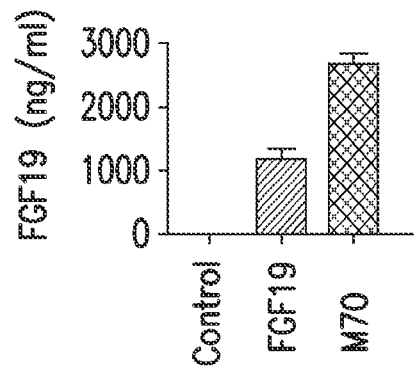
Figure 7G:
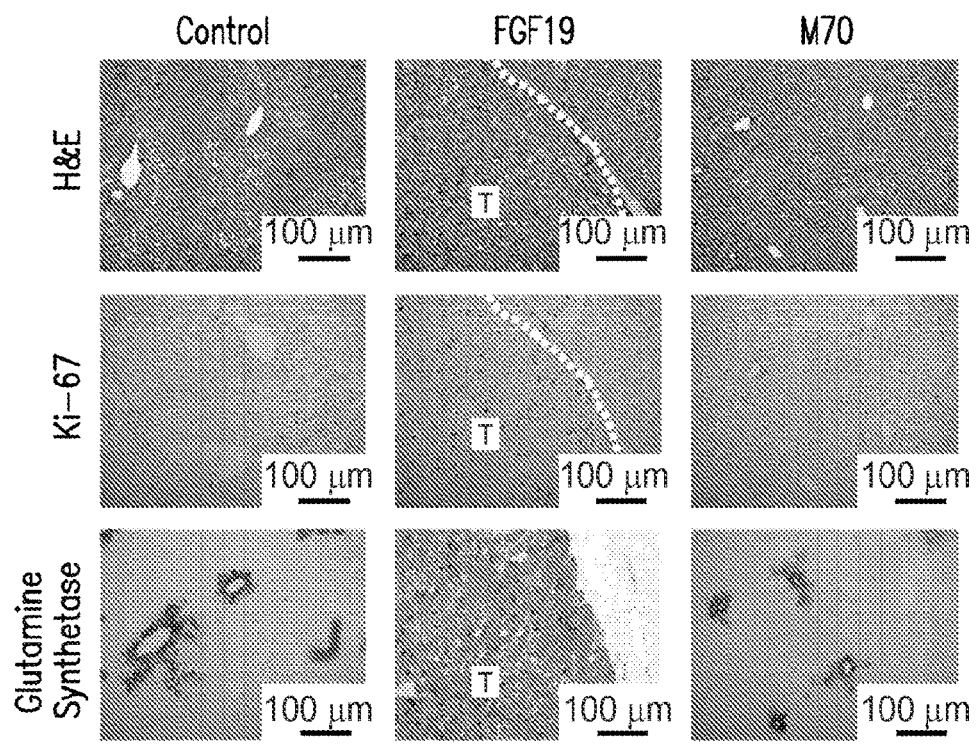
Figure 7H:
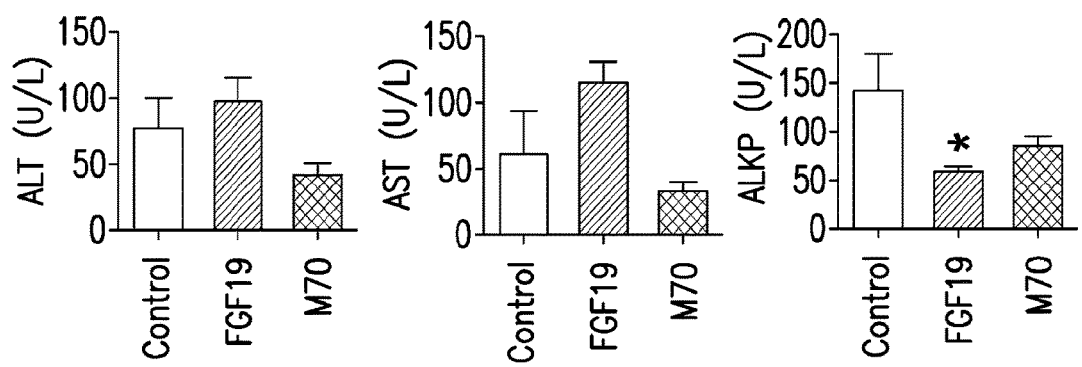

In contrast to FGF19, livers from db/db mice with high systemic exposure to M70 for 24 weeks were completely free of hepatic tumor nodules (15.6±2.8 tumor nodules per liver and 0.0±0.0 tumor nodules per liver for FGF19 and M70, respectively, n=5, p<0.001; FIG. 7B). FGF19-expressing mice exhibited significant increase in liver weight (2.91±0.19 g vs. 1.86±0.12 g in control mice, n=5, p<0.001; FIG. 7C), which as reported in previous studies closely correlates with liver tumor burden. In contrast, M70-expressing mice did not show any increased liver weight (1.56+0.09 g vs. 2.91±0.19 g in FGF19 mice, n=5, p<0.001; FIG. 7C). Similar results were obtained when the liver-to-body weight ratio was calculated (FIG. 7D and FIG. 7E). Average serum concentration of M70 was 2-3 µg/ml in these mice, about 10,000-fold higher than circulating FGF19 level in human (FIG. 7F). Liver histological analysis revealed that M70-expressing mice did not develop any discernable pre-neoplastic and neoplastic lesions associated with FGF19 overexpression in mice. Specifically, no altered hepatic foci, hepatocellular dysplasia, hepatocellular adenomas, or hepatocellular carcinomas was observed (FIG. 7G). In FGF19-expressing mice, non-tumorigenic regions showed increased cellular density around central vein, but no such change was observed in M70-expressing mice. Overexpression of M70 did not cause increased number of Ki-67-positive cells resulting from FGF19-overexpression (FIG. 7G). Furthermore, while liver tumor lesions in FGF19 expressing cells became highly positive for glutamine synthetase, no increased expression of glutamine synthease was observed in the liver of M70 expressing-mice (FIG. 7G). Finally, no liver toxicity was observed following 24 weeks of prolonged exposure to M70, as determined by serum levels of liver enzymes (FIG. 7H). Taken together, these results demonstrate that M70 lacks the ability to promote hepatocellular tumorigenesis in db/db mice.

The tumorigenicity of M70 in a rasH2 transgenic mouse model was further evaluated. CB6F1-RasH2 mice hemizygous for a human H-RAS transgene have been extensively used as an accelerated evaluation for the conventional 2-year carcinogenicity assessment in rodents (Storer et al., 2010, Toxicologic Pathol. 38, 51-61). Sensitive to both genotoxic and nongenotoxic carcinogens, rasH2 mice develop both spontaneous and induced neoplasms earlier than wild type mice. This strain also provides a relevant genetic background for studying hepatocarcinogenicity since activation of RAS signaling pathway is frequently observed in human HCC (Calvisi et al., 2006, Gastroenterol. 130, 1117-1128).

Figure 8A:
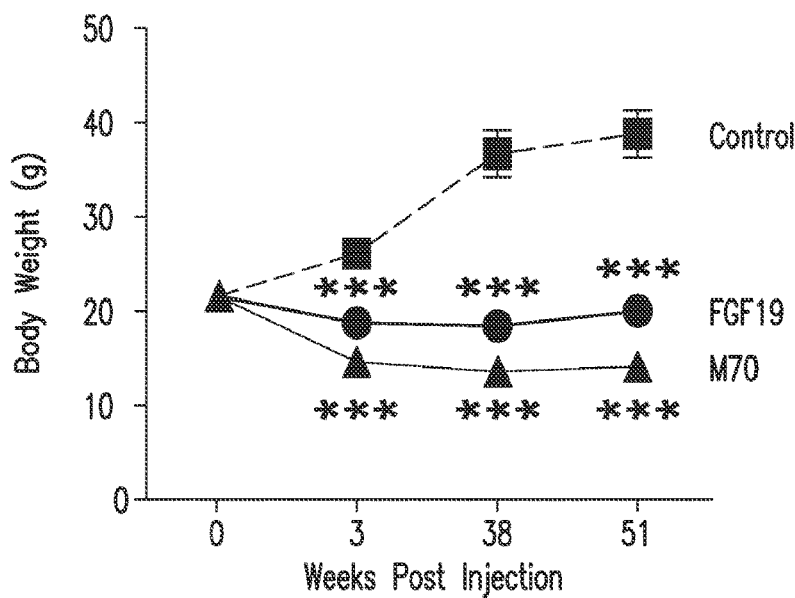
Figure 8B:
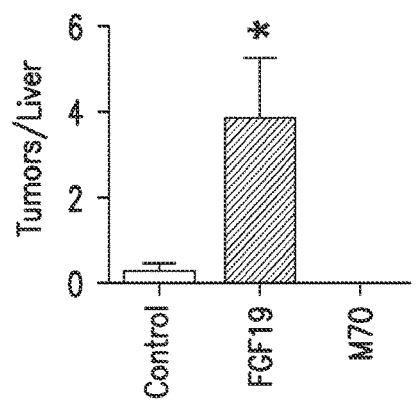
Figure 8C:
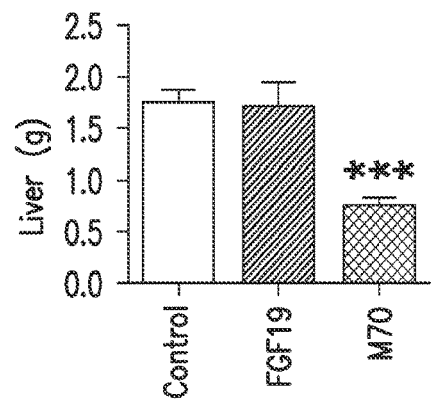
Figure 8D:
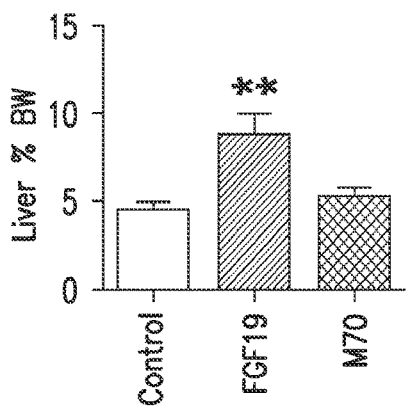
Figure 8E:
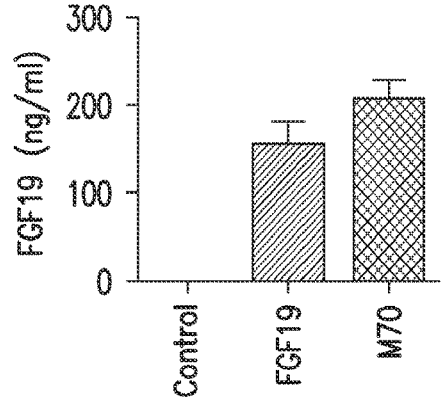

During the course of a 52-week study, rasH2 mice expressing FGF19 or M70 had a significant reduction of body weight gain compared with control mice (FIG. 8A). However, the morphology of the livers from FGF19 and M70-expressing groups showed dramatic differences. Gross morphological changes with multiple tumor nodules were observed in the livers of mice expressing FGF19, consistent with the formation of HCC (3.8+1.5 tumor nodules per liver; FIG. 8B). In contrast, the livers from mice expressing M70 had normal gross morphology and were completely free of tumor nodules (FIG. 8B). It should be pointed out that a low level of spontaneous liver tumor formation was observed in control rasH2 mice (FIG. 8B). M70-expressing animals showed a dramatic decrease in liver weight compared with FGF19 mice (0.76+0.05 g vs. 1.71+0.24 g in FGF19 mice, n=9, p<0.001; FIG. 8C). M70 also normalized the ratio of liver and body weight in rasH2 mice (5.34+0.24% vs. 8.66+1.36% in FGF19 mice, n=9, p<0.01; FIG. 8D). The serum levels of FGF19 and M70 in these mice are comparable, which are 155±28 ng/ml and 209±22 ng/ml, respectively (FIG. 8E).

Figure 8F:
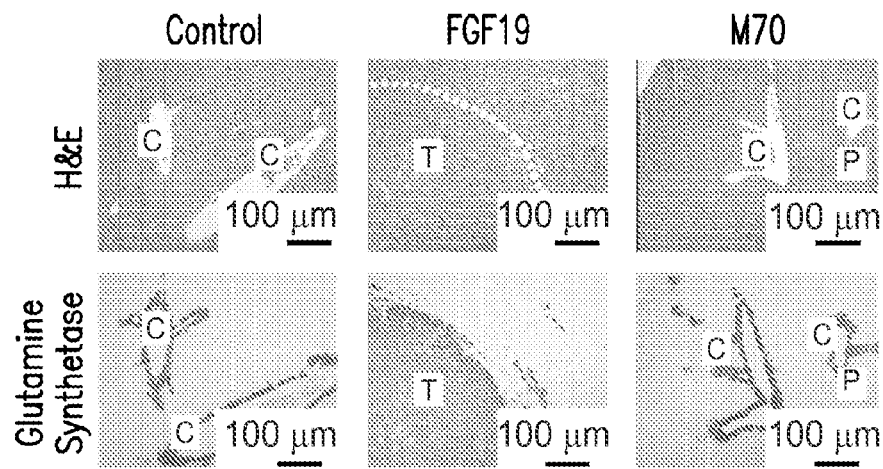
Figure 8G:
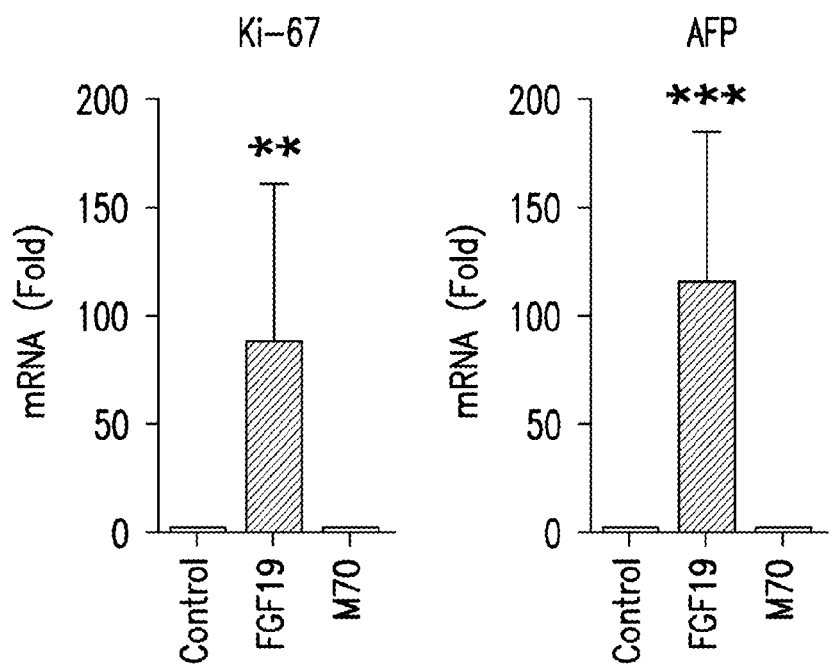

H & E stained liver sections from these mice were evaluated for the presence of tumors and preneoplastic lesions (FIG. 8F). In addition, anti-glutamine synthetase staining was carried out as a marker of FGF19-induced liver tumor (FIG. 8F). The sections stained for glutamine synthetase were taken from paired section stained with H & E and the photographs showed the same portal (p) and central (c) veins. rasH2 mice expressing FGF19 displayed hepatocellular adenoma as well as hepatocellular carcinomas. Preneoplastic hepatocellular lesions were also noted in FGF19-expressing rasH2 mice. Remarkably, none of the livers from mice expressing M70 exhibited tumors or histological evidence of preneoplastic lesions (FIG. 8F). Corroborating histological results, increased hepatic expression of Ki-67 and AFP (an embryonic hepatic protein often induced in HCC (Marrero and El-Serag, 2011, Hepatol. 53, 1060-1062) were observed in FGF19-expressing rasH2 mice, but not in M70-expressing mice (FIG. 8G).

These results demonstrate that, unlike FGF19, prolonged exposure to high circulating levels of M70 (i.e., 24 weeks in db/db mice or 52 weeks in rasH2 mice) does not promote liver tumor formation.

Example 9

M70 Binds and Activates FGFR4 In Vitro and In Vivo

Figure 9A:
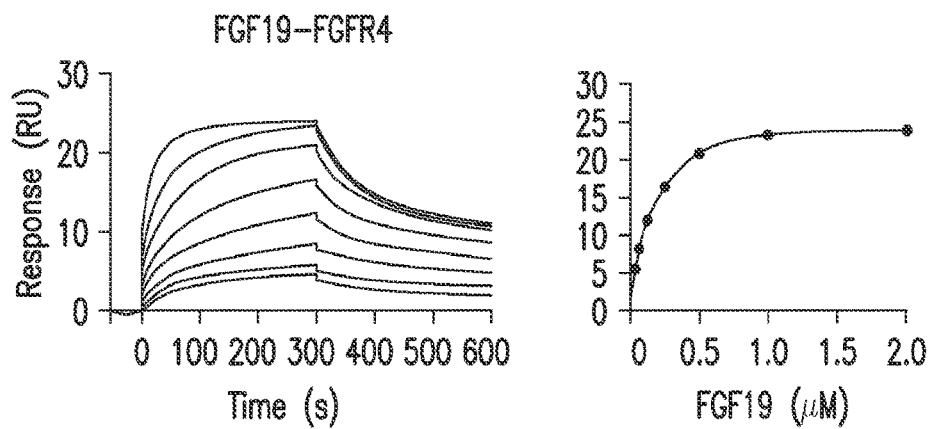
Figure 9B:
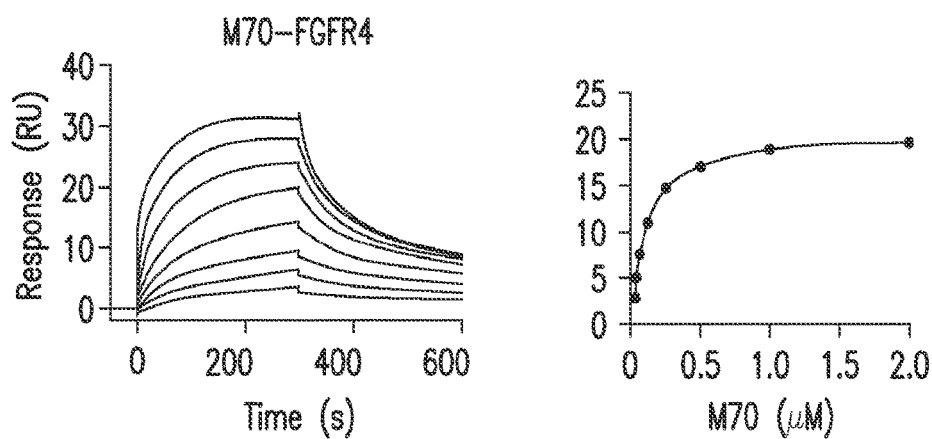
Figure 9C:
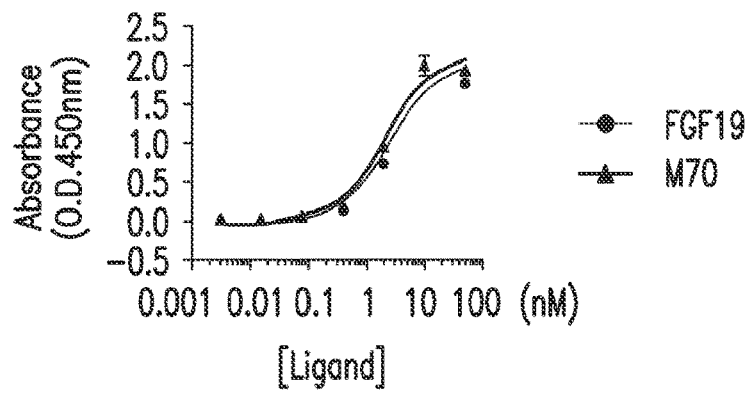

To elucidate the molecular mechanism that underline M70's inability to induce liver tumors, the interaction of M70 to the known receptor complex of FGF19 was assessed. Surface plasmon resonance (SPR) analysis was used to measure direct binding of M70 or FGF19 to FGFR4. In a Biacore assay, M70 or FGF19 was used to flow over chips coated with an Fc fusion protein of the extracellular domain (ECD) of FGFR4. M70 directly interacted with FGFR4 with comparable affinity to FGF19 (dissociation constant $K_D=134\pm47$ nM and $167\pm5$ nM, respectively, FIG. 9A and FIG. 9B). M70 also bound with similar affinity to KLB as FGF19 ($K_D=24.1+11.0$ pM and $28.5+0.8$ pM, respectively; data not shown). M70 binds to the same site of KLB as FGF19, demonstrated by a competition Biacore assay (data not shown). In a solid phase assay, M70 interacted with FGFR4-KLB receptor complex (FIG. 9C). The presence of KLB dramatically increased ligand-receptor affinity. The dissociation constant of M70 binding to the FGFR4-KLB receptor complex indicated a high-affinity interaction, with $K_D$ of 2.14 nM (vs. $K_D$ of 2.49 nM for FGF19).

Figure 9D:
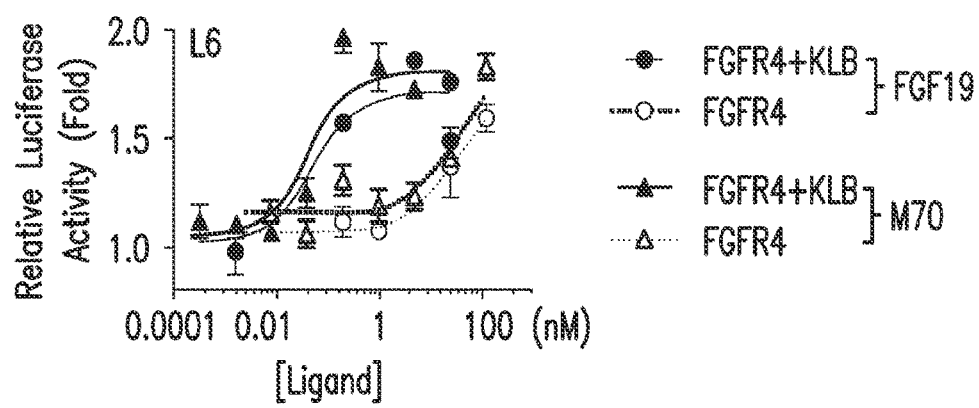
Figure 9E:
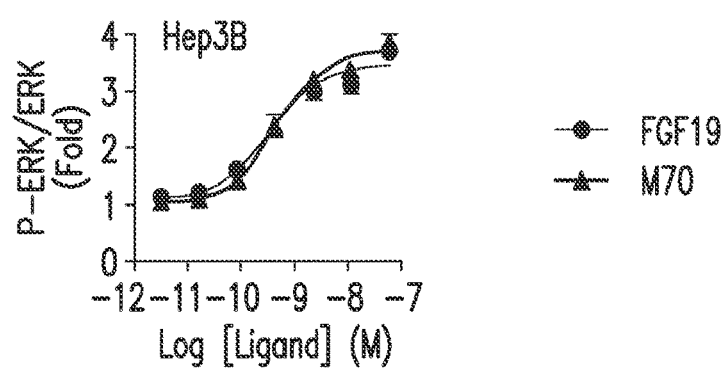

The ability of M70 to activate its receptors was evaluated in a cell-based assay using rat L6 cells transfected with a FGF-responsive GAL-Elkl luciferase reporter gene (Wu et al., 2011, PloS one 6, e17868; Wu et al., 2010a, PNAS, 107, 14158-14163). In this assay, effective binding of a ligand to FGFR results in activation of an endogenous ERK kinase pathway, leading to subsequent activation of a chimeric transcriptional activator comprising of an Elk-1 activation domain and a GAL4 DNA-binding domain. L6 cells lack functional FGFR or KLB and are only responsive to FGF19 when co-transfected with cognate receptors (data not shown). M70 activated intracellular signaling pathways in L6 cells co-expressing FGFR4 and KLB as effectively as FGF19 (EC50=38 pM and 52 pM for M70 and FGF19, respectively; FIG. 9D). In contrast, signaling in cells transfected with FGFR4 alone was much less responsive to either ligand, showing a >500-fold reduction in potency upon addition of either FGF19 or M70 (FIG. 9D). These results suggest that the formation of a ternary complex between FGFR4-KLB co-receptors and the cognate ligands is important for potent activation of intracellular signaling. FGFR4 pathway activation in Hep3B, a human HCC cell line was then analyzed. Hep3B cells predominantly express FGFR4, among isoforms of FGFRs, and KLB. Recombinant M70 protein induced phosphorylation and activation of ERK with a similar potency and efficacy as wild type FGF19 (half maximum effective concentration $EC_{50}=0.38$ nM and 0.37 nM for M70 and FGF19, respectively; FIG. 9E).

Figure 9F:
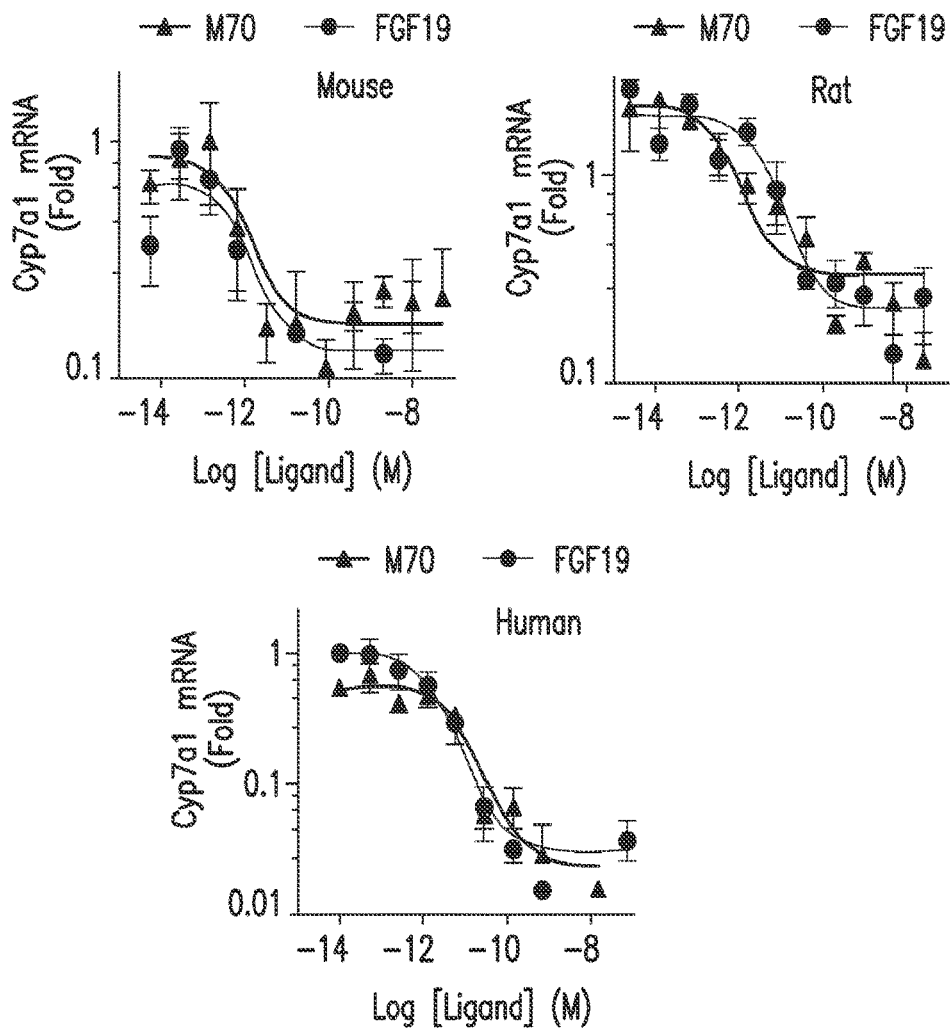

FGF19/FGF15 have been implicated in the regulation of hepatic bile acid metabolism in humans and in rodents, respectively (Holt et al., 2003, Genes Dev. 17, 1581-1591) (Inagaki et al., 2005, Cell Metabol. 2, 217-225). FGF19/FGF15 potently represses hepatic expression of cholesterol-7a-hydroxylase 1 (Cyp7a1), in a process that requires FGFR4 (Inagaki et al., 2005, Cell Metabol. 2, 217-225; Wu et al., 2011, PloS one 6, e17868). The ability of M70 to regulate Cyp7a1 in primary hepatocytes was evaluated. Upon addition to the culture media, M70 effectively repressed Cyp7a1 expression in primary hepatocytes derived from mouse, rat, or human liver (FIG. 9F). The activity of M70 was comparable to that of wild-type FGF19 (half maximum inhibitory concentration 1050 0.64 pM for M70 vs. 0.65 pM for FGF19 in primary mouse hepatocytes; 1050 0.49 pM for M70 vs. 3.96 pM for FGF19 in primary rat hepatocytes; 1050 6.80 pM for M70 vs. 1.73 pM for FGF19 in primary human hepatocytes; FIG. 9F). In primary human hepatocytes, the addition of FGF19 resulted in a maximum suppression of Cyp7a1 mRNA by 97%. Similarly, M70 was able to reduce Cyp7a1 expression by 98% (FIG. 9F).

Figure 9G:
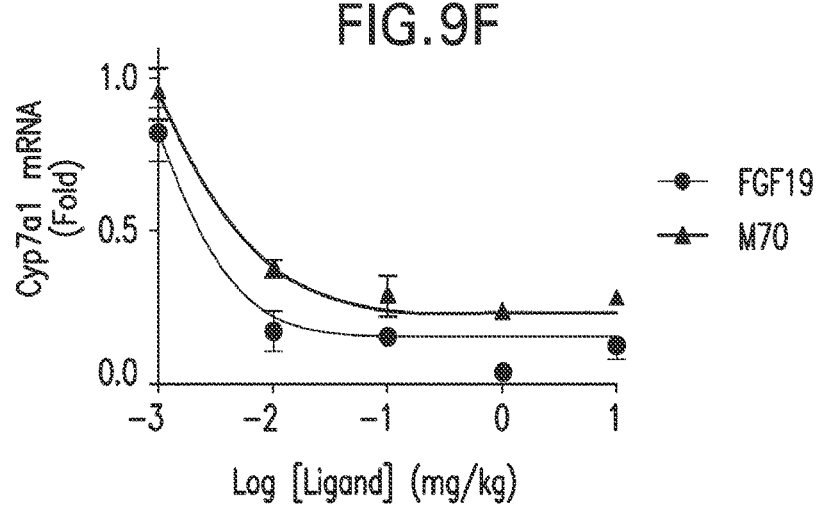

To evaluate the acute effects of M70 administration on hepatic expression of Cyp7a1 in vivo, mice were injected intraperitoneally (i.p.) with recombinant M70 or FGF19 protein at doses ranging from 0.001 to 10 mg/kg (FIG. 9G). A single i.p. injection of M70 potently suppressed Cyp7a1 mRNA with an ED50 of 1.29 µg/kg (FIG. 9G). These data demonstrate that systemic administration of M70 can potently and rapidly trigger FGFR4-mediated intracellular in vivo.

In summary, M70 and wild type FGF19 exhibit a comparable profile of biological activities, leading to activation of ERK signaling and Cyp7a1 regulation.

Example 10

M70 Exhibits Differential Signaling Pathway Activation Compared with FGF19

M70 binds FGFR4 receptor complex and activates the intracellular signaling pathway leading to Cyp7a1 repression, but does not promote liver tumor formation in either db/db or rasH2 mouse models. In order to elucidate the molecular basis for the lack of tumorigenic potential, the activation of key signaling proteins involved in tumorigenesis, including ERK, PI3K/AKT, STATs, and WNT/β-catenin pathways, was analyzed.

M70 and FGF19 proteins (1 mg/kg) were injected intraperitoneally into db/db mice. Livers were collected 15 minutes (data not shown), 2 hours (FIG. 10A), and 4 hours (data not shown) later and phosphorylation of signaling proteins was measured by immunoblotting. Consistent with the ability of both molecules to signal in cultured primary hepatocytes, FGF19 and M70 stimulated ERK phosphorylation to a similar extent in liver tissues in vivo. In line with previous reports on the role of FGF19 in modulating hepatic protein synthesis (Kir et al., 2011, Science 331, 1621-1624), both wild type FGF19 and M70 induced robust phosphorylation of ribosomal S6 protein in the liver (FIG. 10 and data not shown). This agrees with the notion that M70 retains activity on FGFR4-KLB receptor complex. Neither M70 nor FGF19 had any effect on hepatic levels of phosphorylated AKT. No activation of GSK3β and β-catenin was observed at all three time points tested.

Remarkably, FGF19 induced STAT3 phosphorylation 2 hours after dosing (FIG. 10A). This effect lasted to 4 hours post dosing (data not shown). In contrast, M70 did not increase STAT3 phosphorylation (FIG. 10A). IL-6, a known STAT3 activator, was shown to be upregulated in FGF19— but not M70-treated livers (FIG. 10B). The pSTAT3 activation by FGF19 is likely due to non-cell autonomous mechanisms on the liver, since no induction of pSTAT3 was observed 15 minutes after protein injection or in primary mouse hepatocyte culture (data not shown). Corroborating with STAT3 phosphorylation and activation, increased expression of STAT3 target genes, including survivin, bcl-$X_L$, and cyclin D1, was observed in rasH2 livers expressing FGF19, not M70 (FIG. 10C). Since STAT3 is an oncogene frequently activated in HCC (He and Karin, 2011, Cell Res. 21, 159-168), its activation by FGF19 poses a plausible mechanism for FGF19-induced hepatocarcinogenicity. The inability of M70 to activate STAT3 pathway could contribute to its lack of tumorigenicity in vivo.

Thus, M70 only activates a subset of signaling pathways downstream of its receptors, a hallmark of selective modulators (Kenakin and Christopoulos, 2013, Nat. Rev. Drug Discov. 12, 205-21). The identification and characterization of M70 allow us to define two distinct biological processes regulated by FGF19-FGFR4 pathway, bile acid homeostasis and tumorigenesis.

Example 11

M70 Inhibits FGF19-Mediated Tumor Formation

Figure 11E:
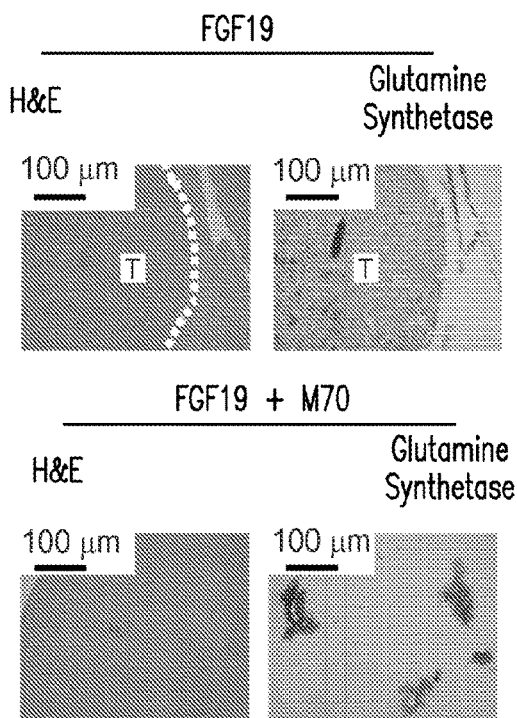
Figure 11F:
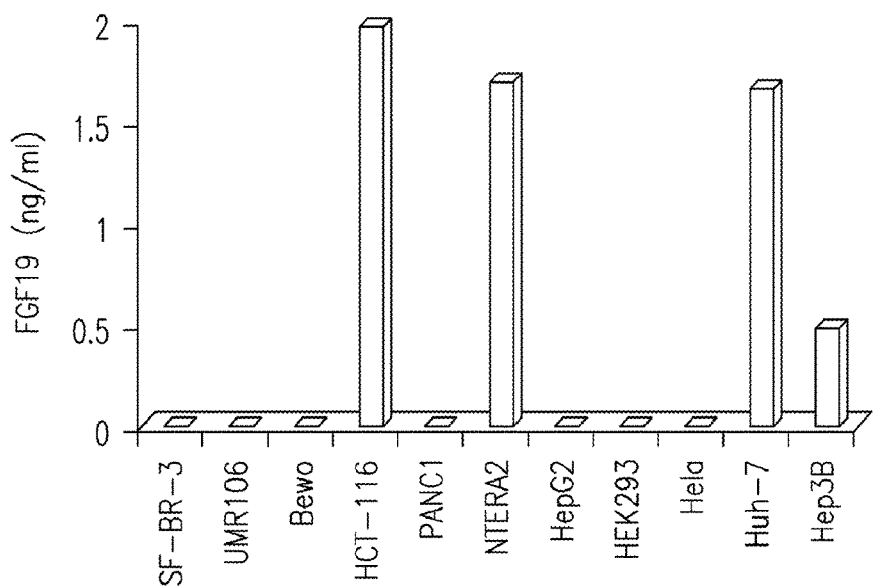

Our observation suggests that M70 behaves as a selective modulator or a "biased ligand" to activate the metabolic signaling but not the tumorigenic signals from FGFR4. Next, it was determined whether the biased agonism of M70 can be utilized to inhibit FGF19-associated tumor formation via an orthosteric or allosteric mechanism.

db/db mice were injected with $3 \times 10^{10}$ genome copies of AAV-FGF19, with or without 10-fold molar excess of AAV-M70 ($3 \times 10^{11}$ genome copies). Mice were necropsied 24 weeks after transgene expression and the livers were exercised for analysis. While ectopic expression of FGF19 in db/db mice promoted the formation of tumor nodules on hepatic surface (7.8+2.3 tumor nodules per liver), livers from mice expressing both FGF19 and M70 were completely free of tumor nodules (FIG. 11A). Liver weights from M70-coexpressing mice were significantly lower relative to FGF19-expressing mice (1.59 g±0.14 g and 2.42 g±0.20 g, respectively, n=5, p<0.01; FIG. 11B). The ratios of liver to body weight in M70 and FGF19 co-treated mice were not significantly different from those of control mice (FIG. 11C). The serum levels of FGF19 were 94±12 ng/ml when dosed alone, and the combined serum level of FGF19 and M70 was 453±169 ng/ml (FIG. 11D). Histological analysis of the livers confirmed that unlike FGF19-expression mice, mice co-expressing M70 and FGF19 did not exhibit any histological evidence of liver tumors (FIG. 11E). These data demonstrate that M70 effectively competes with FGF19 to prevent tumor formation in FGF19-expressing mice.

FGF19 is reported to be amplified and/or overexpressed in HCC and colon cancer (Desnoyers et al., 2008; Sawey et al., 2011, Oncogene 27, 85-97). A panel of liver, colon, breast and other human cancer cell lines were screened, and it was observed that FGF19 is produced and secreted by, among others, Huh-7 (HCC) and HCT-116 (colon cancer) cell lines (FIG. 11F), which were chosen for further studies. The levels of FGF19 in the culture media reached 1-2 ng/ml by ELISA measurement, about 10-fold higher than physiological FGF19 concentration in human.

Figure 11G:
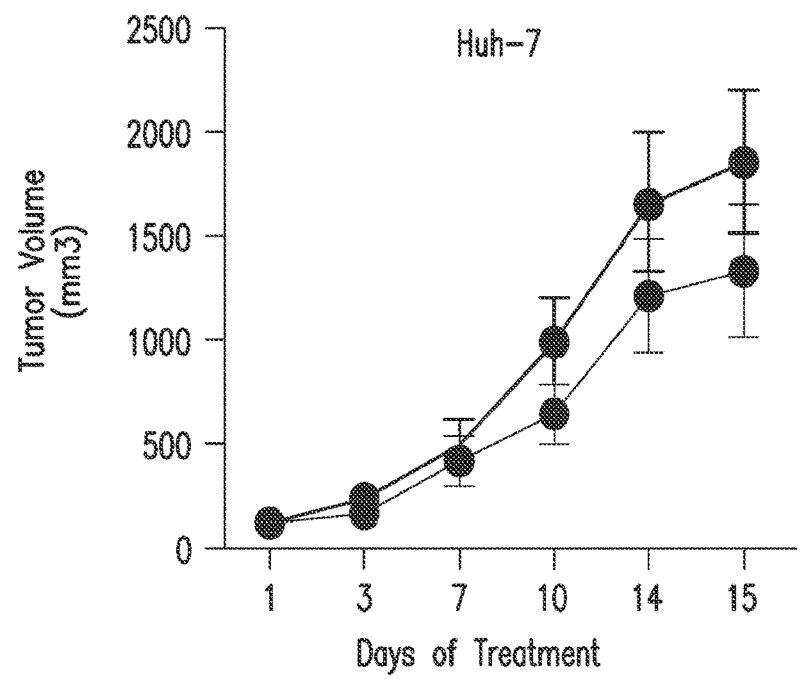

HCC cell line Huh-7 harbors the 11q13.3 amplicon and overexpresses both FGF19 and CCND1. The effect of M70 on the tumor-forming ability of Huh-cells was tested. Athymic nude mice were injected subcutaneously with Huh-7 cells, and tumors were allowed to reach a size of ~100 mm$^3$. At that point, mice were placed into 2 treatment groups: one injected intravenously with AAV-M70, another with a control virus. M70-treated mice exhibited a trend of delayed growth by 28% (end-stage tumor size: 1856±348 mm$^3$ in controls vs. 1340±406 mm$^3$ after M70 treatment; n=10; FIG. 11G). No significant effect on body weight was noted (data not shown).

Figure 11H:
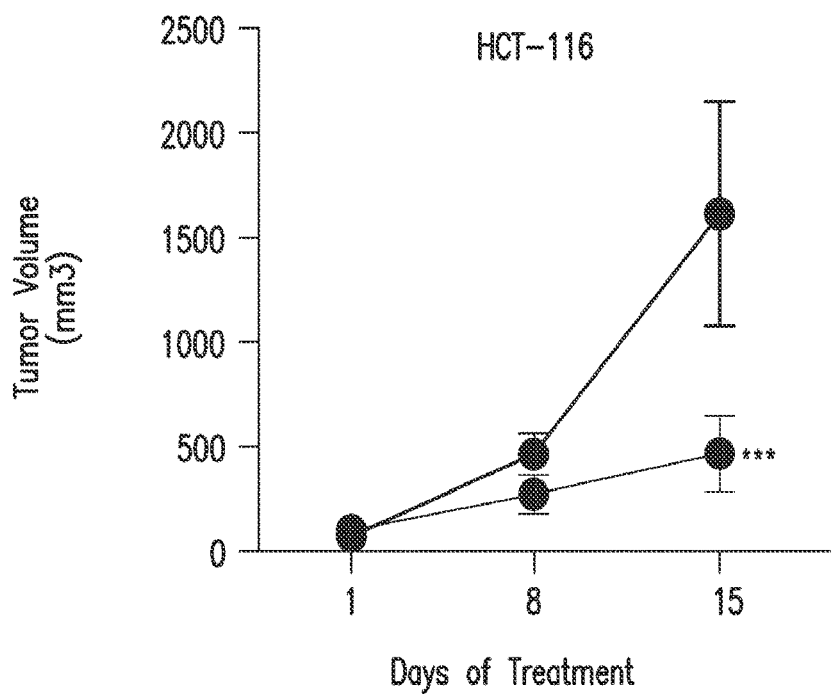
Figure 11I:
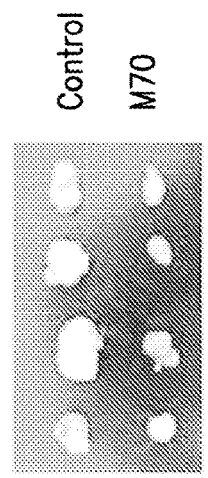
Figure 11J:
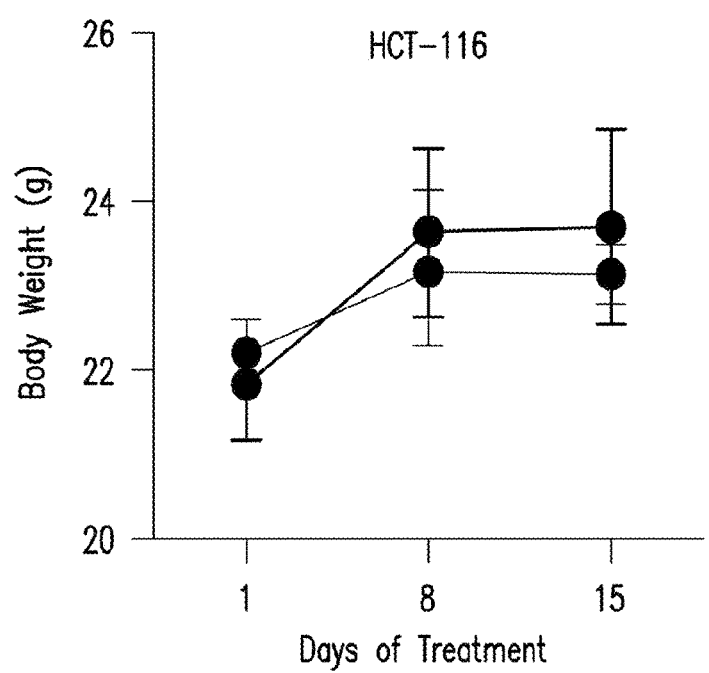

The effect of M70 on HCT-116 colon cancer xenograft growth was also examiner. Mice bearing established HCT116 colon cancer tumors were dosed with AAV-M70 or control virus. As early as day 8 after treatment began, M70 suppressed tumor growth by 37% (tumor size: 459±83 mm$^3$ in control group vs. 287±87 mm$^3$ in M70 group; n=5; FIG. 11H). On day 15 post treatment, M70-treated mice exhibited a statistically significant 71% inhibition of tumor growth (end-stage tumor size: 1634±524 mm$^3$ in controls vs. 479±155 mm$^3$ after M70 treatment, n=5, p<0.001; FIGS. 11H and 11I). No significant effect on body weight was observed (FIG. 11J).

These results suggest that M70 acts as a biased ligand that is capable of antagonizing wild type FGF19 in tumorigenic signaling, and demonstrate the potential of using a selective modulator such as M70 to suppress FGF19-dependent tumor growth.

Example 12

M70 Inhibits CT26 Colon Tumor Growth

This study was conducted to further assess the effect of M70 on tumor progression in a syngenic model in immune-competent mice. CT26 is a mouse colon cancer cell line, which grafts and grows well in syngenic Balb/c mice. CT26 was widely used for characterizing compounds/agents on tumor growth, especially for evaluating cancer immunotherapies.

As a positive control, a blocking antibody against Programmed Death-1 (PD-1) was used. PD-1 and its ligands PD-L1/PD-L2 represent an immune checkpoint axis. The PD-1 pathway down-regulates tumor-specific immunity by impairing T-cell responses and promoting the induction of Foxp3+ Tregs in the periphery. Blocking the PD-1 pathway, in conjunction with other immune therapies, inhibits tumor progression in syngenic models. Multiple human anti-PD-1 monoclonal antibodies (mAbs), as well as human anti-PD-L1 mAbs, have entered clinical trials, and the first anti-PD-1 antibody was recently approved by FDA as an anti-cancer therapy.

Balb/c mice were purchased from the Jackson Laboratory. Animals were maintained in a pathogen-free facility. All animal protocols were approved by Institutional Animal Care and Use Committee at NGM Biopharmaceuticals.

CT26 mouse colon cancer cell line was purchased from ATCC. Cells were cultured in DMEM with 10% FBS and penicillin/streptomycin cocktail. Exponentially grown cells were harvested for implantation in mice. Cells were resuspended in saline for injection.

Balb/c mice were implanted with $1 \times 10^6$ CT26 cells on the right flank. Three days later, M70 protein was subcutaneously injected in Balb/c mice bearing the CT26 implant once daily for 15 days. The growth of CT26 tumor was measured twice weekly with a caliper. Tumor volume was calculated using formula: Tumor volume=width$^2$*length/2.

As shown in FIG. 13, M70 delays tumor growth in a CT26 colon cancer syngenic mouse model following administration of 10 mg/kg doses (FIG. 13A) or 3 mg/kg doses (FIG. 13B) as compared to vehicle alone. M70 was also shown to reduce body weight following administration of 10 mg/kg doses (FIG. 14A) or 3 mg/kg doses (FIG. 14B).

Thus, these studies show that M70 treatment delays CT26 colon tumor growth in immune-competent Balb/c syngenic mice, with anti-tumor efficacy being observed for both doses (3 mg/kg and 10 mg/kg) of M70.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

SEQUENCE LISTING

The present specification is being filed with a computer readable form (CRF) copy of the Sequence Listing. The CRF entitled 13370-020-228_SEQLIST.txt, which was created on Oct. 27, 2014 and is 50,105 bytes in size, is identical to the paper copy of the Sequence Listing and is incorporated herein by reference in its entirety.

What is claimed is:

1. A method of treating a FGF19-dependent cancer or tumor, or a symptom thereof, in a subject in need thereof, comprising administering to the subject a therapeutically effective amount of a polypeptide comprising or consisting of the amino acid sequence set forth in SEQ ID NO:1, thereby treating the FGF19-dependent cancer or tumor, or symptom thereof in the subject.

2. The method of claim 1, wherein the FGF19-dependent cancer or tumor is hepatocellular carcinoma, a colon cancer or tumor, a prostate cancer or tumor, or a lung cancer or tumor.

3. The method of claim 2, wherein polypeptide comprises the amino acid sequence set forth in SEQ ID NO:1.

4. The method of claim 3, wherein the FGF19-dependent cancer or tumor is hepatocellular carcinoma.

5. The method of claim 3, wherein the FGF19-dependent cancer or tumor is a colon cancer or tumor.

6. The method of claim 3, wherein the FGF19-dependent cancer or tumor is a prostate cancer or tumor.

7. The method of claim 3, wherein the FGF19-dependent cancer or tumor is a lung cancer or tumor.

8. The method of claim 2, wherein polypeptide consists of the amino acid sequence set forth in SEQ ID NO:1.

9. The method of claim 8, wherein the FGF19-dependent cancer or tumor is hepatocellular carcinoma.

10. The method of claim 8, wherein the FGF19-dependent cancer or tumor is a colon cancer or tumor.

11. The method of claim 8, wherein the FGF19-dependent cancer or tumor is a prostate cancer or tumor.

12. The method of claim 8, wherein the FGF19-dependent cancer or tumor is a lung cancer or tumor.

13. The method of claim 1, wherein polypeptide comprises the amino acid sequence set forth in SEQ ID NO:1.

14. The method of claim 1, wherein polypeptide consists of the amino acid sequence set forth in SEQ ID NO:1.

15. A method of antagonizing the oncogenic activity of FGF19 in a subject in need thereof, comprising administering to the subject a therapeutically effective amount of a polypeptide comprising or consisting of the amino acid sequence set forth in SEQ ID NO:1, thereby antagonizing the oncogenic activity of FGF19 in the subject.

16. The method of claim 15, wherein polypeptide comprises the amino acid sequence set forth in SEQ ID NO:1.

17. The method of claim 16, wherein the subject has hepatocellular carcinoma.

18. The method of claim 16, wherein the subject has a colon cancer or tumor.

19. The method of claim 16, wherein the subject has a prostate cancer or tumor.

20. The method of claim 16, wherein the subject has a lung cancer or tumor.

21. The method of claim 15, wherein polypeptide consists of the amino acid sequence set forth in SEQ ID NO:1.

22. The method of claim 21, wherein the subject has hepatocellular carcinoma.

23. The method of claim 21, wherein the subject has a colon cancer or tumor.

24. The method of claim 21, wherein the subject has a prostate cancer or tumor.

25. The method of claim 21, wherein the subject has a lung cancer or tumor.

* * * * *

SEQUENCE LISTING

```
<160> NUMBER OF SEQ ID NOS: 42

<210> SEQ ID NO 1
<211> LENGTH: 190
<212> TYPE: PRT
<213> ORGANISM: Artificial Sequence
<220> FEATURE:
<223> OTHER INFORMATION: M70 sequence

<400> SEQUENCE: 1

Met Arg Asp Ser Ser Pro Leu Val His Tyr Gly Trp Gly Asp Pro Ile
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 2
<211> LENGTH: 8
<212> TYPE: PRT
<213> ORGANISM: Artificial Sequence
<220> FEATURE:
<223> OTHER INFORMATION: FLAG-tag (or FLAG octapeptide) sequence
```

```
<400> SEQUENCE: 2

Asp Tyr Lys Asp Asp Asp Asp Lys
1               5

<210> SEQ ID NO 3
<211> LENGTH: 194
<212> TYPE: PRT
<213> ORGANISM: Homo sapiens
<220> FEATURE:
<223> OTHER INFORMATION: FGF19 sequence

<400> SEQUENCE: 3

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Trp Gly Asp Pro Ile
1               5

<210> SEQ ID NO 5
<211> LENGTH: 191
<212> TYPE: PRT
<213> ORGANISM: Artificial Sequence
<220> FEATURE:
<223> OTHER INFORMATION: M5 sequence

<400> SEQUENCE: 5

Arg His Pro Ile Pro Asp Ser Ser Pro Leu Leu Gln Phe Gly Gly Gln
1               5                   10                  15
```

```
Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 6
<211> LENGTH: 187
<212> TYPE: PRT
<213> ORGANISM: Artificial Sequence
<220> FEATURE:
<223> OTHER INFORMATION: M6 sequence

<400> SEQUENCE: 6

Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
                180                 185
```

<210> SEQ ID NO 7
<211> LENGTH: 192
<212> TYPE: PRT
<213> ORGANISM: Artificial Sequence
<220> FEATURE:
<223> OTHER INFORMATION: M7 sequence

<400> SEQUENCE: 7

```
Arg Pro Leu Ala Phe Ser Asp Ser Ser Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 8
<211> LENGTH: 191
<212> TYPE: PRT
<213> ORGANISM: Artificial Sequence
<220> FEATURE:
<223> OTHER INFORMATION: M14 sequence

<400> SEQUENCE: 8

```
Arg His Pro Ile Pro Asp Ser Ser Pro His Val His Tyr Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125
```

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 9
<211> LENGTH: 192
<212> TYPE: PRT
<213> ORGANISM: Artificial Sequence
<220> FEATURE:
<223> OTHER INFORMATION: M15 sequence

<400> SEQUENCE: 9

Arg Pro Leu Ala Phe Ser Asp Ala Gly Pro His Val His Tyr Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 10
<211> LENGTH: 191
<212> TYPE: PRT
<213> ORGANISM: Artificial Sequence
<220> FEATURE:
<223> OTHER INFORMATION: M32 sequence

<400> SEQUENCE: 10

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr

```
                    50                  55                  60
Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
                130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 11
<211> LENGTH: 191
<212> TYPE: PRT
<213> ORGANISM: Artificial Sequence
<220> FEATURE:
<223> OTHER INFORMATION: M36 sequence

<400> SEQUENCE: 11

Arg His Pro Ile Pro Asp Ser Ser Pro Leu Leu Gln Phe Gly Gly Asn
  1                   5                  10                  15

Val Arg Leu Arg His Leu Tyr Thr Ser Gly Pro His Gly Leu Ser Ser
                 20                  25                  30

Cys Phe Leu Arg Ile Arg Ala Asp Gly Val Val Asp Cys Ala Arg Gly
                 35                  40                  45

Gln Ser Ala His Ser Leu Leu Glu Ile Lys Ala Val Ala Leu Arg Thr
 50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
                130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 12
<211> LENGTH: 192
<212> TYPE: PRT
<213> ORGANISM: Artificial Sequence
<220> FEATURE:
<223> OTHER INFORMATION: M43 sequence
```

-continued

<400> SEQUENCE: 12

Arg Pro Leu Ala Phe Ser Asp Ala Gly Pro His Val His Tyr Gly Gly
1               5                   10                  15

Asp Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 13
<211> LENGTH: 191
<212> TYPE: PRT
<213> ORGANISM: Artificial Sequence
<220> FEATURE:
<223> OTHER INFORMATION: M50 sequence

<400> SEQUENCE: 13

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Leu Glu Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

```
Asp Met Phe Ser Ser Pro Leu Glu Thr Asp Ser Met Asp Pro Phe Gly
            165                 170                 175

Leu Val Thr Gly Leu Glu Ala Val Arg Ser Pro Ser Phe Glu Lys
        180                 185                 190

<210> SEQ ID NO 14
<211> LENGTH: 187
<212> TYPE: PRT
<213> ORGANISM: Artificial Sequence
<220> FEATURE:
<223> OTHER INFORMATION: M52 sequence

<400> SEQUENCE: 14

Arg Asp Ser Ser Pro Leu Leu Gln Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 15
<211> LENGTH: 194
<212> TYPE: PRT
<213> ORGANISM: Artificial Sequence
<220> FEATURE:
<223> OTHER INFORMATION: M53 sequence

<400> SEQUENCE: 15

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95
```

Asp Cys Ala Phe Glu Glu Ile Leu Pro Asp Gly Tyr Asn Val Tyr
                100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 16
<211> LENGTH: 191
<212> TYPE: PRT
<213> ORGANISM: Artificial Sequence
<220> FEATURE:
<223> OTHER INFORMATION: M67 sequence

<400> SEQUENCE: 16

Arg Pro Leu Ala Phe Ser Asp Ala Gly Pro His Val Trp Gly Asp Pro
1               5                   10                  15

Ile Arg Leu Arg His Leu Tyr Thr Ser Gly Pro His Gly Leu Ser Ser
                20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 17
<211> LENGTH: 193
<212> TYPE: PRT
<213> ORGANISM: Artificial Sequence
<220> FEATURE:
<223> OTHER INFORMATION: M68 sequence

<400> SEQUENCE: 17

Arg Pro Leu Ala Phe Ser Asp Ala Gly Pro His Val His Tyr Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 18
<211> LENGTH: 189
<212> TYPE: PRT
<213> ORGANISM: Artificial Sequence
<220> FEATURE:
<223> OTHER INFORMATION: M69 sequence

<400> SEQUENCE: 18

Arg Asp Ser Ser Pro Leu Val His Tyr Gly Trp Gly Asp Pro Ile Arg
1               5                   10                  15

Leu Arg His Leu Tyr Thr Ser Gly Pro His Gly Leu Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

```
Thr Gly Leu Glu Ala Val Arg Ser Pro Ser Phe Glu Lys
            180                 185
```

<210> SEQ ID NO 19
<211> LENGTH: 190
<212> TYPE: PRT
<213> ORGANISM: Artificial Sequence
<220> FEATURE:
<223> OTHER INFORMATION: M70 sequence

<400> SEQUENCE: 19

```
Met Arg Asp Ser Ser Pro Leu Val His Tyr Gly Trp Gly Asp Pro Ile
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190
```

<210> SEQ ID NO 20
<211> LENGTH: 184
<212> TYPE: PRT
<213> ORGANISM: Artificial Sequence
<220> FEATURE:
<223> OTHER INFORMATION: M75 sequence

<400> SEQUENCE: 20

```
Arg Val His Tyr Gly Trp Gly Asp Pro Ile Arg Leu Arg His Leu Tyr
1               5                   10                  15

Thr Ser Gly Pro His Gly Leu Ser Ser Cys Phe Leu Arg Ile Arg Ala
            20                  25                  30

Asp Gly Val Val Asp Cys Ala Arg Gly Gln Ser Ala His Ser Leu Leu
        35                  40                  45

Glu Ile Lys Ala Val Ala Leu Arg Thr Val Ala Ile Lys Gly Val His
    50                  55                  60

Ser Val Arg Tyr Leu Cys Met Gly Ala Asp Gly Lys Met Gln Gly Leu
65                  70                  75                  80

Leu Gln Tyr Ser Glu Glu Asp Cys Ala Phe Glu Glu Glu Ile Arg Pro
                85                  90                  95

Asp Gly Tyr Asn Val Tyr Arg Ser Glu Lys His Arg Leu Pro Val Ser
            100                 105                 110
```

Leu Ser Ser Ala Lys Gln Arg Gln Leu Tyr Lys Asn Arg Gly Phe Leu
            115                 120                 125

Pro Leu Ser His Phe Leu Pro Met Leu Pro Met Val Pro Glu Glu Pro
        130                 135                 140

Glu Asp Leu Arg Gly His Leu Glu Ser Asp Met Phe Ser Ser Pro Leu
145                 150                 155                 160

Glu Thr Asp Ser Met Asp Pro Phe Gly Leu Val Thr Gly Leu Glu Ala
                165                 170                 175

Val Arg Ser Pro Ser Phe Glu Lys
                180

<210> SEQ ID NO 21
<211> LENGTH: 179
<212> TYPE: PRT
<213> ORGANISM: Artificial Sequence
<220> FEATURE:
<223> OTHER INFORMATION: M76 sequence

<400> SEQUENCE: 21

Arg Gly Asp Pro Ile Arg Leu Arg His Leu Tyr Thr Ser Gly Pro His
1               5                   10                  15

Gly Leu Ser Ser Cys Phe Leu Arg Ile Arg Ala Asp Gly Val Val Asp
            20                  25                  30

Cys Ala Arg Gly Gln Ser Ala His Ser Leu Leu Glu Ile Lys Ala Val
        35                  40                  45

Ala Leu Arg Thr Val Ala Ile Lys Gly Val His Ser Val Arg Tyr Leu
    50                  55                  60

Cys Met Gly Ala Asp Gly Lys Met Gln Gly Leu Leu Gln Tyr Ser Glu
65                  70                  75                  80

Glu Asp Cys Ala Phe Glu Glu Ile Arg Pro Asp Gly Tyr Asn Val
                85                  90                  95

Tyr Arg Ser Glu Lys His Arg Leu Pro Val Ser Leu Ser Ser Ala Lys
                100                 105                 110

Gln Arg Gln Leu Tyr Lys Asn Arg Gly Phe Leu Pro Leu Ser His Phe
            115                 120                 125

Leu Pro Met Leu Pro Met Val Pro Glu Glu Pro Glu Asp Leu Arg Gly
        130                 135                 140

His Leu Glu Ser Asp Met Phe Ser Ser Pro Leu Glu Thr Asp Ser Met
145                 150                 155                 160

Asp Pro Phe Gly Leu Val Thr Gly Leu Glu Ala Val Arg Ser Pro Ser
                165                 170                 175

Phe Glu Lys

<210> SEQ ID NO 22
<211> LENGTH: 175
<212> TYPE: PRT
<213> ORGANISM: Artificial Sequence
<220> FEATURE:
<223> OTHER INFORMATION: M77 sequence

<400> SEQUENCE: 22

Arg Arg Leu Arg His Leu Tyr Thr Ser Gly Pro His Gly Leu Ser Ser
1               5                   10                  15

Cys Phe Leu Arg Ile Arg Ala Asp Gly Val Val Asp Cys Ala Arg Gly
            20                  25                  30

Gln Ser Ala His Ser Leu Leu Glu Ile Lys Ala Val Ala Leu Arg Thr
        35                  40                  45

```
Val Ala Ile Lys Gly Val His Ser Val Arg Tyr Leu Cys Met Gly Ala
         50                  55                  60

Asp Gly Lys Met Gln Gly Leu Leu Gln Tyr Ser Glu Glu Asp Cys Ala
 65                  70                  75                  80

Phe Glu Glu Ile Arg Pro Asp Gly Tyr Asn Val Tyr Arg Ser Glu
                 85                  90                  95

Lys His Arg Leu Pro Val Ser Leu Ser Ser Ala Lys Gln Arg Gln Leu
             100                 105                 110

Tyr Lys Asn Arg Gly Phe Leu Pro Leu Ser His Phe Leu Pro Met Leu
             115                 120                 125

Pro Met Val Pro Glu Glu Pro Glu Asp Leu Arg Gly His Leu Glu Ser
             130                 135                 140

Asp Met Phe Ser Ser Pro Leu Glu Thr Asp Ser Met Asp Pro Phe Gly
145                 150                 155                 160

Leu Val Thr Gly Leu Glu Ala Val Arg Ser Pro Ser Phe Glu Lys
                 165                 170                 175

<210> SEQ ID NO 23
<211> LENGTH: 194
<212> TYPE: PRT
<213> ORGANISM: Artificial Sequence
<220> FEATURE:
<223> OTHER INFORMATION: M83 sequence

<400> SEQUENCE: 23

Arg Pro Leu Ala Phe Ser Asp Ala Ala Pro His Val His Tyr Gly Trp
 1               5                   10                  15

Gly Asp Pro Ile Arg Leu Arg His Leu Tyr Thr Ser Gly Pro His Gly
             20                  25                  30

Leu Ser Ser Cys Phe Leu Arg Ile Arg Ala Asp Gly Val Val Asp Cys
             35                  40                  45

Ala Arg Gly Gln Ser Ala His Ser Leu Leu Glu Ile Lys Ala Val Ala
         50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
             100                 105                 110

Arg Ser Glu Lys His Arg Leu Pro Val Ser Leu Ser Ser Ala Lys Gln
             115                 120                 125

Arg Gln Leu Tyr Lys Asn Arg Gly Phe Leu Pro Leu Ser His Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 24
<211> LENGTH: 194
<212> TYPE: PRT
<213> ORGANISM: Artificial Sequence
<220> FEATURE:
```

<223> OTHER INFORMATION: M84 sequence

<400> SEQUENCE: 24

Arg Pro Leu Ala Phe Ser Asp Ala Gly Ala His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 25
<211> LENGTH: 194
<212> TYPE: PRT
<213> ORGANISM: Artificial Sequence
<220> FEATURE:
<223> OTHER INFORMATION: M140 sequence

<400> SEQUENCE: 25

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Glu Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

```
Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
            165                 170                 175

Pro Phe Gly Leu Val Thr Gly Leu Glu Ala Val Arg Ser Pro Ser Phe
        180                 185                 190

Glu Lys
```

<210> SEQ ID NO 26
<211> LENGTH: 190
<212> TYPE: PRT
<213> ORGANISM: Artificial Sequence
<220> FEATURE:
<223> OTHER INFORMATION: M144 (M5-R) sequence

<400> SEQUENCE: 26

```
His Pro Ile Pro Asp Ser Ser Pro Leu Leu Gln Phe Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190
```

<210> SEQ ID NO 27
<211> LENGTH: 186
<212> TYPE: PRT
<213> ORGANISM: Artificial Sequence
<220> FEATURE:
<223> OTHER INFORMATION: M145 (M6-R) sequence

<400> SEQUENCE: 27

```
Asp Ser Ser Pro Leu Leu Gln Phe Gly Gly Gln Val Arg Leu Arg His
1               5                   10                  15

Leu Tyr Thr Ser Gly Pro His Gly Leu Ser Ser Cys Phe Leu Arg Ile
            20                  25                  30

Arg Ala Asp Gly Val Val Asp Cys Ala Arg Gly Gln Ser Ala His Ser
        35                  40                  45

Leu Leu Glu Ile Lys Ala Val Ala Leu Arg Thr Val Ala Ile Lys Gly
    50                  55                  60
```

```
Val His Ser Val Arg Tyr Leu Cys Met Gly Ala Asp Gly Lys Met Gln
 65                  70                  75                  80

Gly Leu Leu Gln Tyr Ser Glu Glu Asp Cys Ala Phe Glu Glu Glu Ile
                 85                  90                  95

Arg Pro Asp Gly Tyr Asn Val Tyr Arg Ser Glu Lys His Arg Leu Pro
                100                 105                 110

Val Ser Leu Ser Ser Ala Lys Gln Arg Gln Leu Tyr Lys Asn Arg Gly
            115                 120                 125

Phe Leu Pro Leu Ser His Phe Leu Pro Met Leu Pro Met Val Pro Glu
        130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
                180                 185

<210> SEQ ID NO 28
<211> LENGTH: 190
<212> TYPE: PRT
<213> ORGANISM: Artificial Sequence
<220> FEATURE:
<223> OTHER INFORMATION: M146 (M50-R) sequence

<400> SEQUENCE: 28

His Pro Ile Pro Asp Ser Ser Pro Leu Leu Gln Phe Gly Asp Gln Val
  1               5                  10                  15

Arg Leu Arg His Leu Tyr Thr Ser Gly Pro His Gly Leu Ser Ser Cys
                 20                  25                  30

Phe Leu Arg Ile Arg Ala Asp Gly Val Val Asp Cys Ala Arg Gly Gln
             35                  40                  45

Ser Ala His Ser Leu Leu Glu Ile Lys Ala Val Ala Leu Arg Thr Val
 50                  55                  60

Ala Ile Lys Gly Val His Ser Val Arg Tyr Leu Cys Met Gly Ala Asp
 65                  70                  75                  80

Gly Lys Met Gln Gly Leu Leu Gln Tyr Ser Glu Glu Asp Cys Ala Phe
                 85                  90                  95

Glu Glu Glu Ile Leu Glu Asp Gly Tyr Asn Val Tyr Arg Ser Glu Lys
                100                 105                 110

His Arg Leu Pro Val Ser Leu Ser Ser Ala Lys Gln Arg Gln Leu Tyr
            115                 120                 125

Lys Asn Arg Gly Phe Leu Pro Leu Ser His Phe Leu Pro Met Leu Pro
        130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
                180                 185                 190

<210> SEQ ID NO 29
<211> LENGTH: 194
<212> TYPE: PRT
<213> ORGANISM: Artificial Sequence
<220> FEATURE:
<223> OTHER INFORMATION: M160 sequence

<400> SEQUENCE: 29
```

-continued

```
Arg Pro Leu Ala Phe Ser Asp Ala Gly Pro His Val His Tyr Gly Trp
1               5                   10                  15

Gly Asp Pro Ile Arg Gln Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Ile Leu Glu Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
            130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 30
<211> LENGTH: 11
<212> TYPE: PRT
<213> ORGANISM: Artificial Sequence
<220> FEATURE:
<223> OTHER INFORMATION: residues 47-57 of HIV-1 TAT

<400> SEQUENCE: 30

Tyr Gly Arg Lys Lys Arg Arg Gln Arg Arg Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31

Arg Arg Gln Arg Arg Thr Ser Lys Leu Met Lys Arg
1               5                   10

<210> SEQ ID NO 32
<211> LENGTH: 27
<212> TYPE: PRT
<213> ORGANISM: Artificial Sequence
<220> FEATURE:
<223> OTHER INFORMATION: Synthetic peptide

<400> SEQUENCE: 32

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
```

20                  25

<210> SEQ ID NO 33
<211> LENGTH: 33
<212> TYPE: PRT
<213> ORGANISM: Artificial Sequence
<220> FEATURE:
<223> OTHER INFORMATION: Synthetic peptide

<400> SEQUENCE: 33

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 34
<211> LENGTH: 16
<212> TYPE: PRT
<213> ORGANISM: Artificial Sequence
<220> FEATURE:
<223> OTHER INFORMATION: Synthetic peptide

<400> SEQUENCE: 34

Arg Gln Ile Lys Ile Trp Phe Gln Asn Arg Arg Met Lys Trp Lys Lys
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Arg Lys Lys Arg Arg Gln Arg Arg Arg
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Arg Lys Lys Arg Arg Gln Arg Arg
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide

<400> SEQUENCE: 37

Tyr Ala Arg Ala Ala Ala Arg Gln Ala Arg Ala
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic peptide

```
<400> SEQUENCE: 38

Thr His Arg Leu Pro Arg Arg Arg Arg Arg
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic peptide

<400> SEQUENCE: 39

Gly Gly Arg Arg Ala Arg Arg Arg Arg Arg
1               5                   10

<210> SEQ ID NO 40
<211> LENGTH: 32
<212> TYPE: DNA
<213> ORGANISM: Artificial Sequence
<220> FEATURE:
<223> OTHER INFORMATION: Forward primer

<400> SEQUENCE: 40
ccgactagtc accatgcgga gcgggtgtgt gg                              32

<210> SEQ ID NO 41
<211> LENGTH: 41
<212> TYPE: DNA
<213> ORGANISM: Artificial Sequence
<220> FEATURE:
<223> OTHER INFORMATION: Reverse primer

<400> SEQUENCE: 41
ataagaatgc ggccgcttac ttctcaaagc tgggactcct c                    41

<210> SEQ ID NO 42
<211> LENGTH: 202
<212> TYPE: PRT
<213> ORGANISM: Artificial Sequence
<220> FEATURE:
<223> OTHER INFORMATION: synthetic peptide

<400> SEQUENCE: 42

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140
```

-continued

```
Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
            165                 170                 175

Pro Phe Gly Leu Val Thr Gly Leu Glu Ala Val Arg Ser Pro Ser Phe
            180                 185                 190

Glu Lys Asp Tyr Lys Asp Asp Asp Lys
        195             200
```